(12) United States Patent
Rolfs et al.

(10) Patent No.: US 11,231,412 B2
(45) Date of Patent: *Jan. 25, 2022

(54) METHOD FOR THE DIAGNOSIS OF NIEMANN-PICK DISEASE

(71) Applicant: Centogene GmbH, Rostock (DE)

(72) Inventors: Arndt Rolfs, Berlin (DE); Hermann Mascher, Traiskirchen (AT)

(73) Assignee: Centogene GmbH, Rostock (DE)

( * ) Notice: Subject to any disclaimer, the term of this patent is extended or adjusted under 35 U.S.C. 154(b) by 67 days.

This patent is subject to a terminal disclaimer.

(21) Appl. No.: 16/541,716

(22) Filed: Aug. 15, 2019

(65) Prior Publication Data
US 2020/0072819 A1 Mar. 5, 2020

Related U.S. Application Data

(63) Continuation of application No. 15/700,949, filed on Sep. 11, 2017, now Pat. No. 10,422,789, which is a continuation of application No. 14/358,669, filed as application No. PCT/EP2012/004756 on Nov. 15, 2012, now Pat. No. 9,910,033.

(30) Foreign Application Priority Data

Nov. 15, 2011 (EP) .................................. 11009062

(51) Int. Cl.
G01N 33/53 (2006.01)
G01N 33/92 (2006.01)
C12Q 1/6883 (2018.01)
G01N 30/72 (2006.01)

(52) U.S. Cl.
CPC .......... *G01N 33/53* (2013.01); *C12Q 1/6883* (2013.01); *G01N 30/7233* (2013.01); *G01N 33/92* (2013.01); *G01N 2800/04* (2013.01); *G01N 2800/52* (2013.01)

(58) Field of Classification Search
None
See application file for complete search history.

(56) References Cited

U.S. PATENT DOCUMENTS

2009/0286272 A1  11/2009  Ory .................... G01N 33/6893
                                                                      435/29
2011/0052559 A1   3/2011  Schuchman et al.

FOREIGN PATENT DOCUMENTS

WO   2010/120330 A2   10/2010

OTHER PUBLICATIONS

Rodriguez-Lafrasse et al., Neurochem. Res. 24(2): 199-205 (1999).*
Dannielle te Vruchte et al., Relative acidic compartment volume as a lysosomal storage disorder-associated biomarker, The Journal of Clinical Investigation, vol. 124 No. 3 Mar. 2014, 1320-1328.

(Continued)

*Primary Examiner* — Erin M. Bowers
(74) *Attorney, Agent, or Firm* — Stanek Lemon Crouse & Meeks, PA

(57) ABSTRACT

The present invention is related to a method for diagnosing Niemann-Pick disease in a subject comprising
a step a), wherein the step a) comprises detecting a biomarker in a sample from the subject.

7 Claims, 30 Drawing Sheets

(56) References Cited

OTHER PUBLICATIONS

Anne-Katrin Giese et al., A novel, highly sensitive and specific biomarkers for Niemann-Pick type C1 disease, Giese et al. Orphanet Jounral of Rare Diseases, 2015, 10:78.
Tomas Blom et al., Tracking Sphingosine Metablolism and Transport in Sphingollpldoses: NPC1 Deficiency as a Test Case, Traffic 2012; 13: 1234-1243.
Wei-Lien Chuang., Lyso-sphingomyelin is elevated in dried blood spots of Niemann-Pick B patients, Molecular Genetics and Metabolism 111, 2014, 209-211.
Japanese Office Action dated Oct. 12, 2016 for a corresponding Japanese Patent Application No. 2014-541566.
Nixon, et al., "The multi-functional role of sphingosylphosphorylcholine", Progress in Lipid Research 47(1): 62-75 (2007).
Rodriguez-Lafrasse, et al., "Sphingosylphosphorycholine in Niemann-Pick Disease Brain: Accumulation in Type A But Not in Type B", Neurochemical Research 24(2): 199-205 (1999).
International Search Report for International Application PCT/EP2012/004756, dated Jun. 7, 2013.
Scherer et al., J. Lipid Res. 51: 2001-2011 (2010).
McDade et al., Demography 44(4): 899-925 (2007).
Giese et al., Orphanet Journal of Rare Diseases 10: 78 (2015).

\* cited by examiner

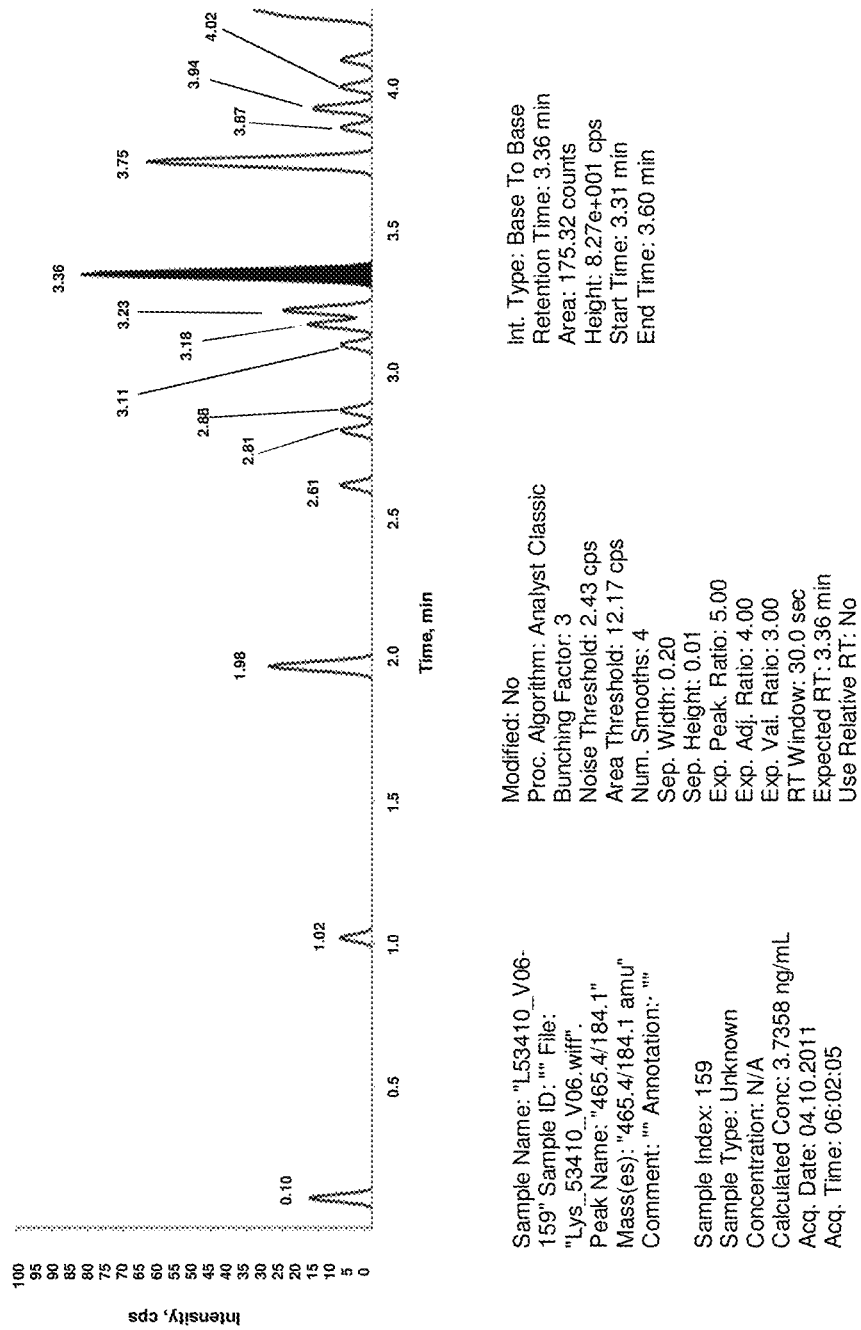
Fig. 8A (1)

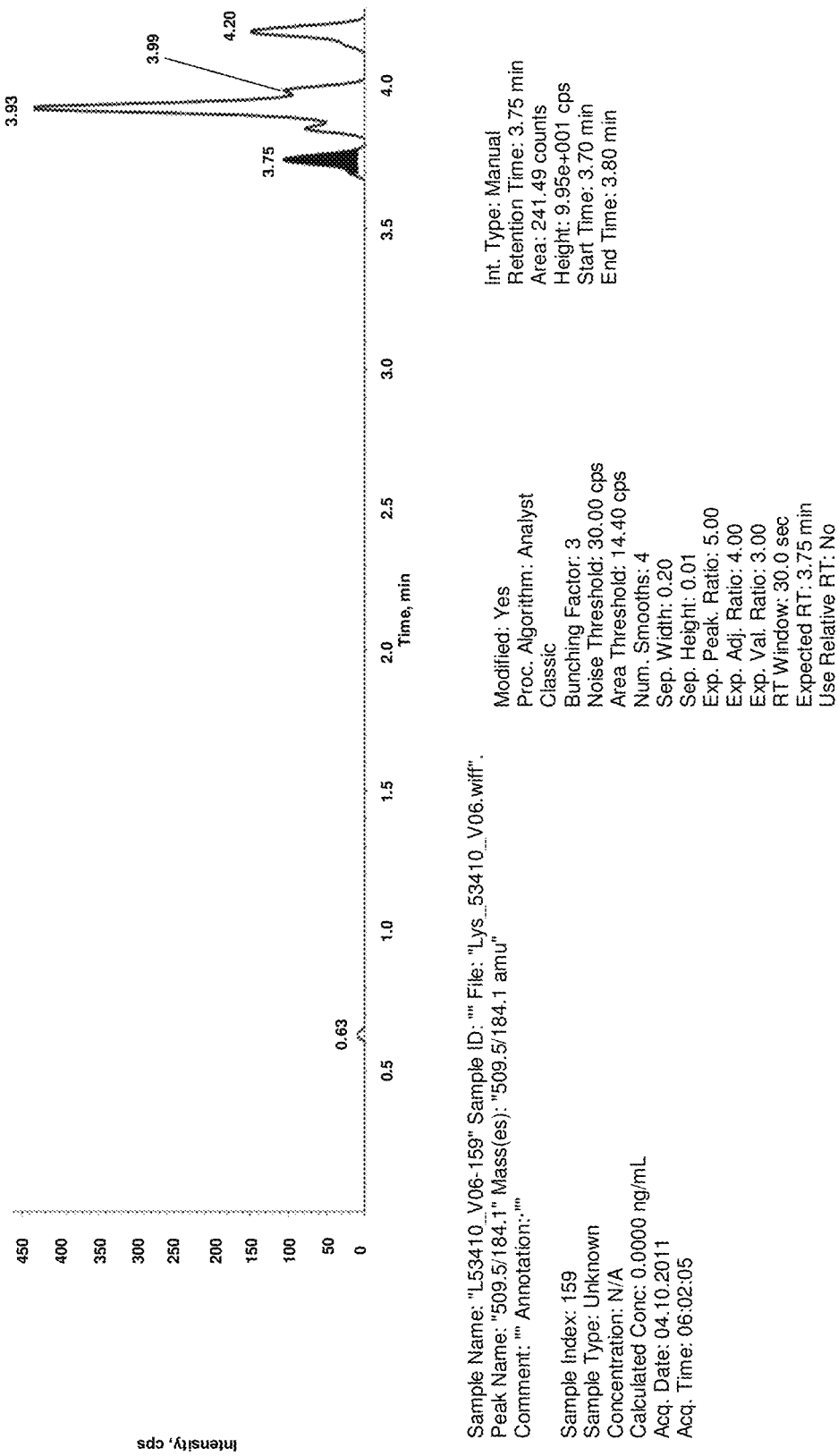
Fig. 8A (2)

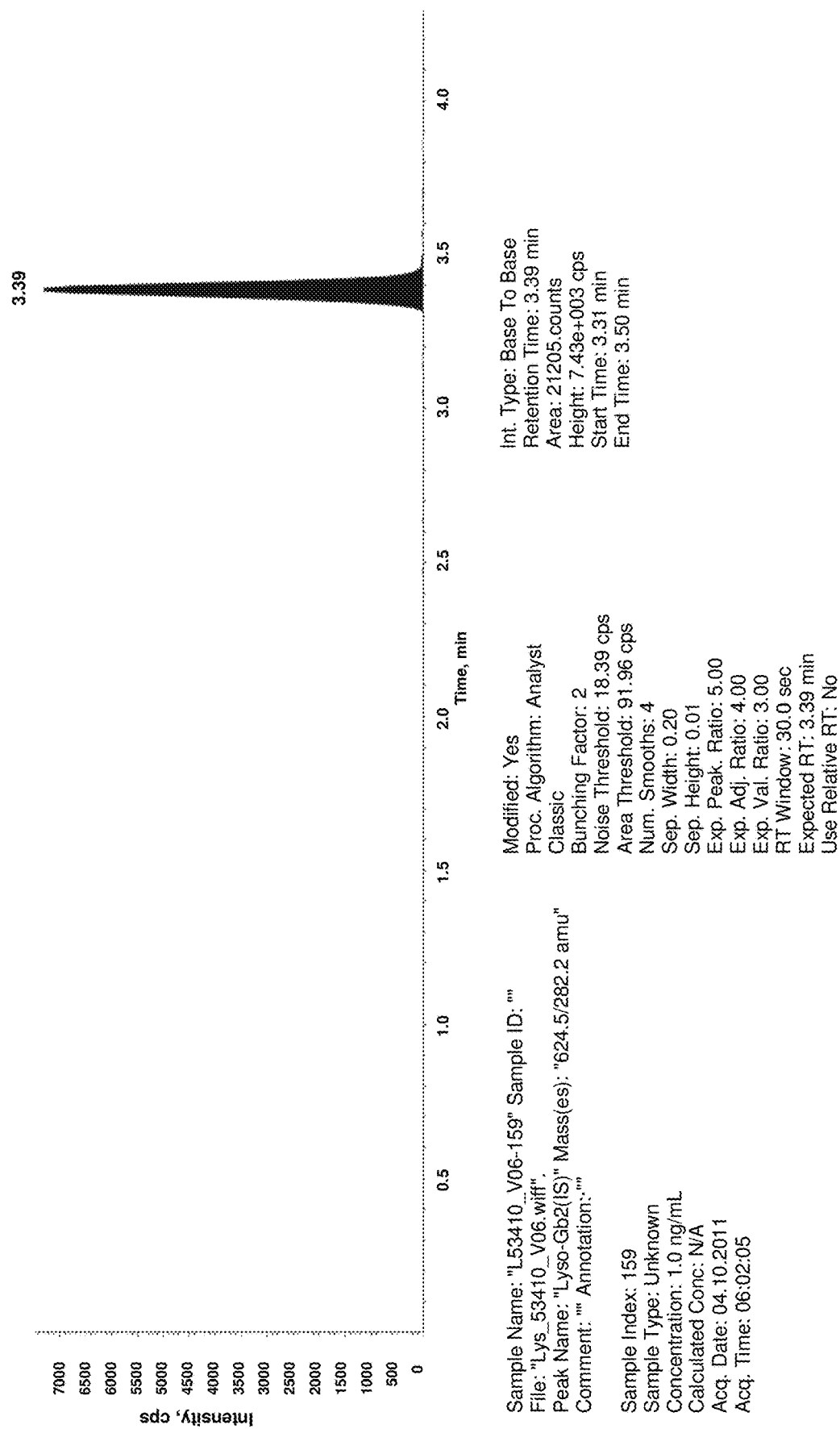
Fig. 8A (3)

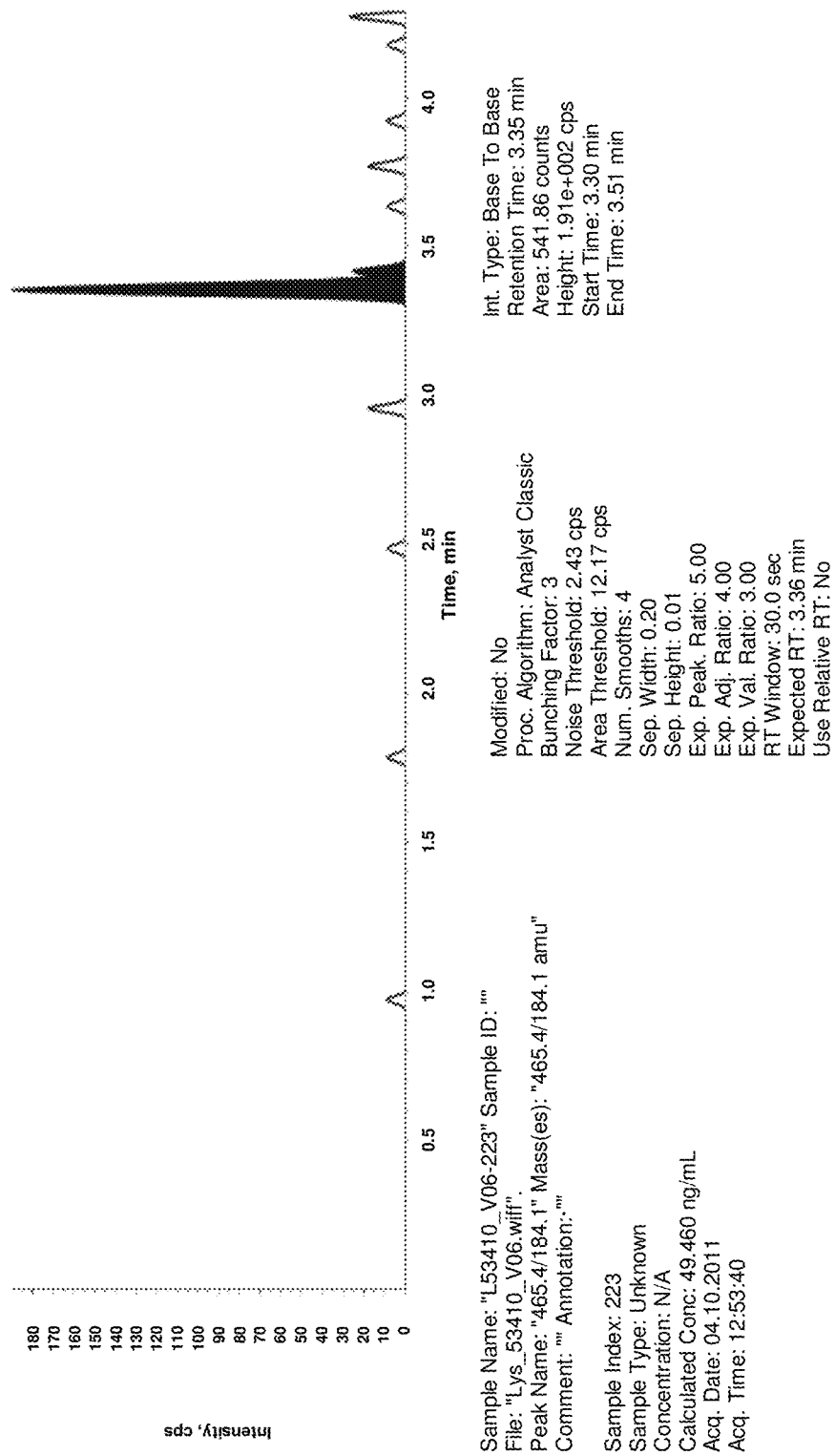
Fig. 8B (1)

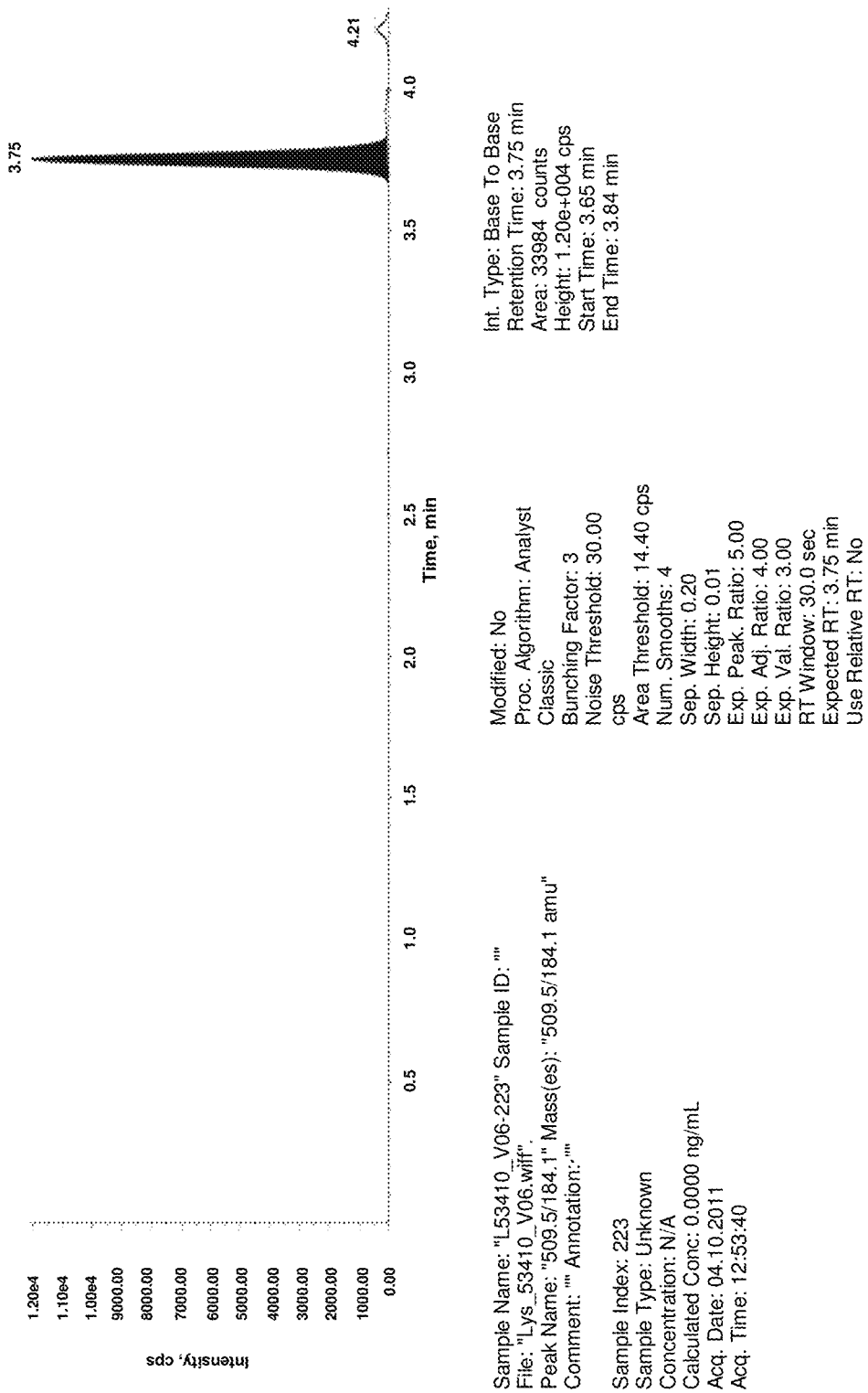
Fig. 8B (2)

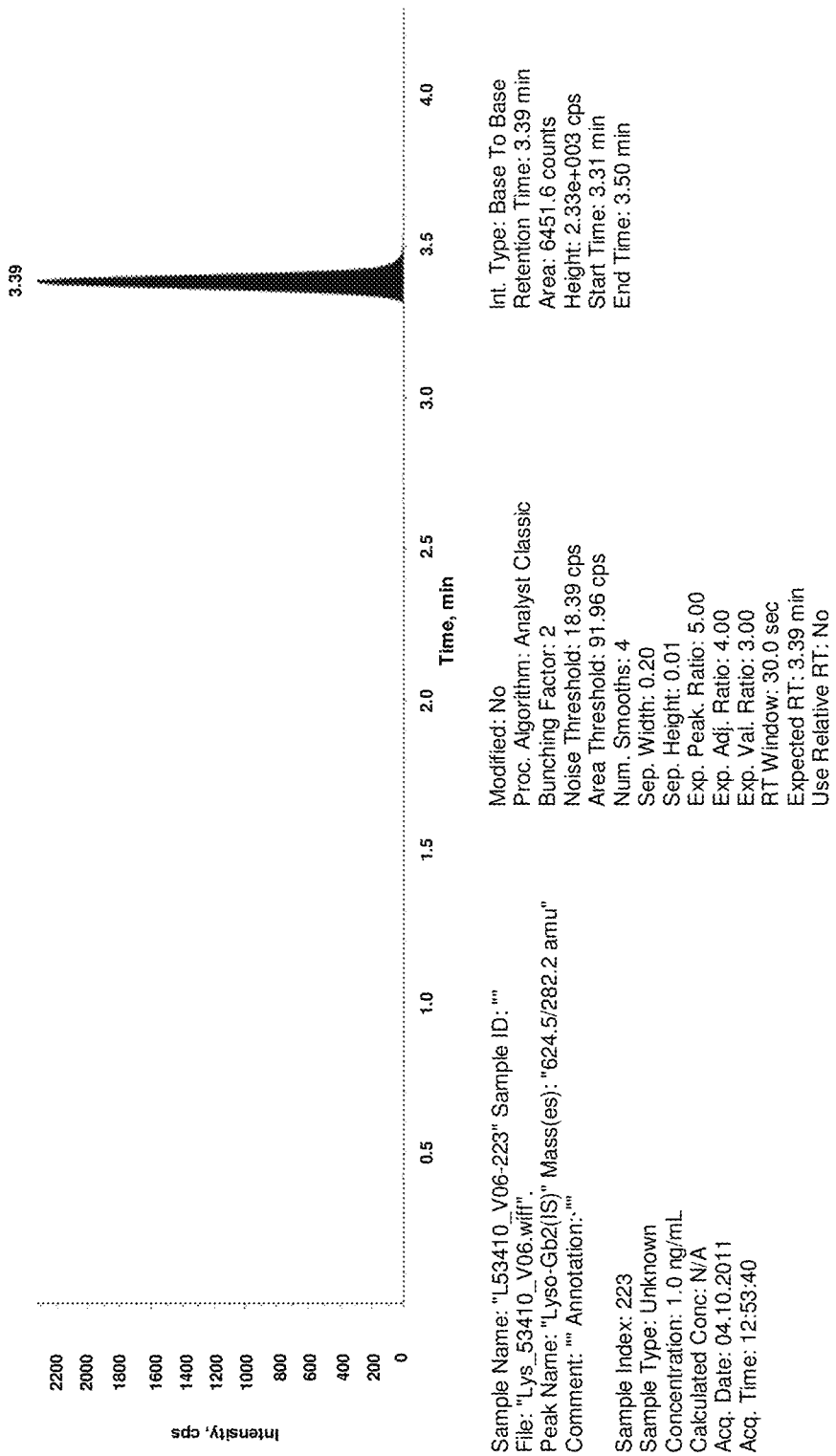
Fig. 8B (3)

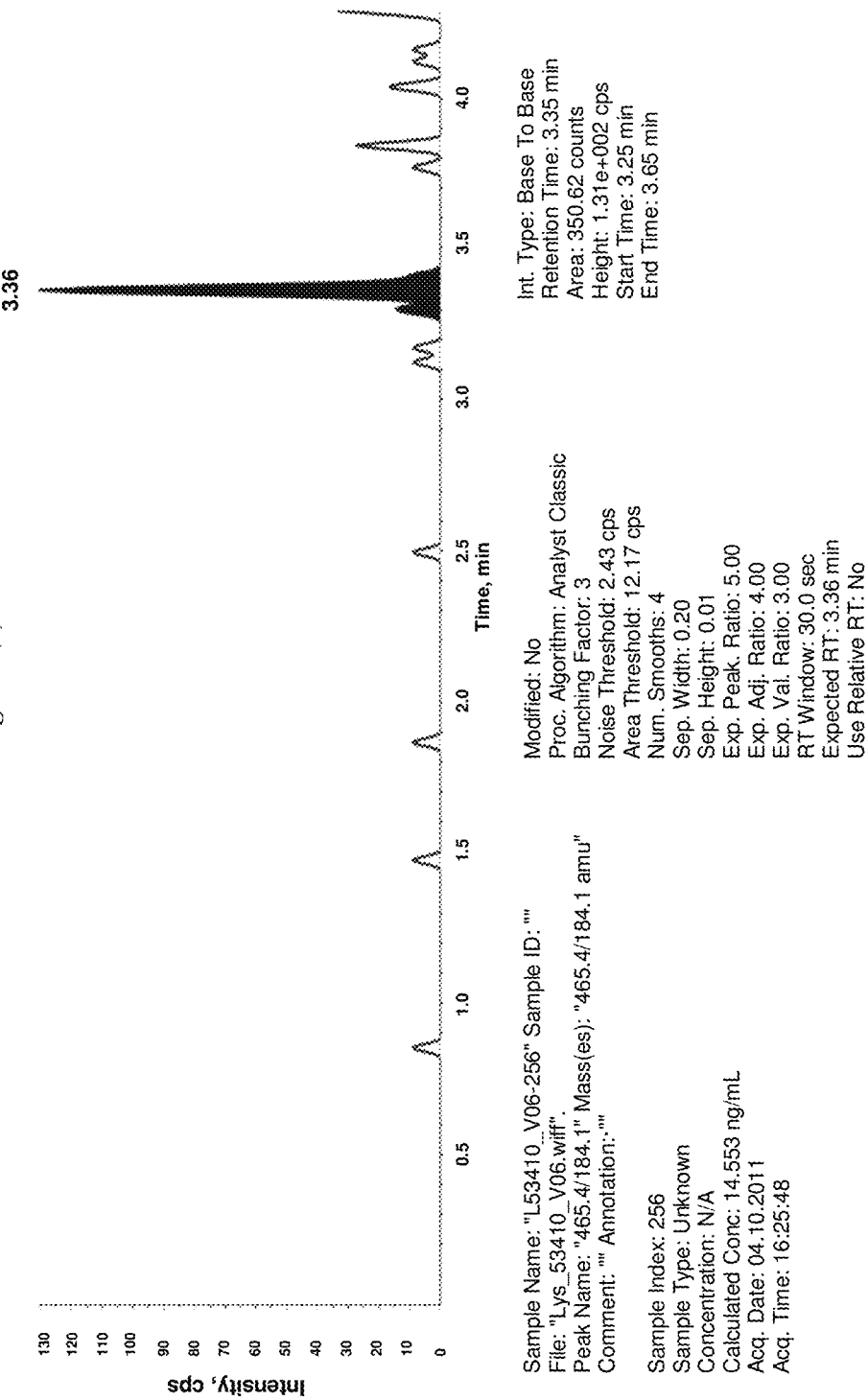
Fig. 8C (1)

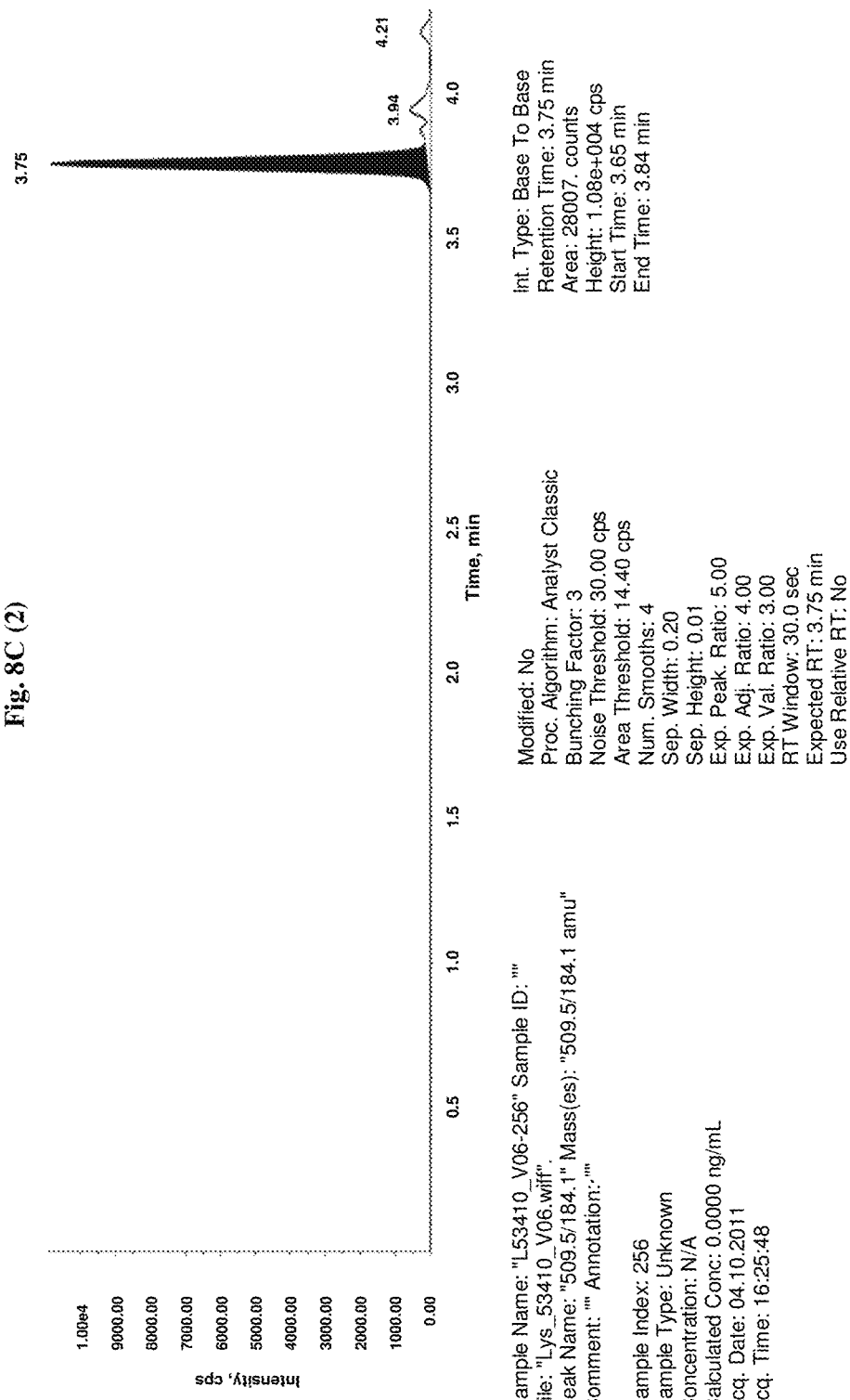
Fig. 8C (2)

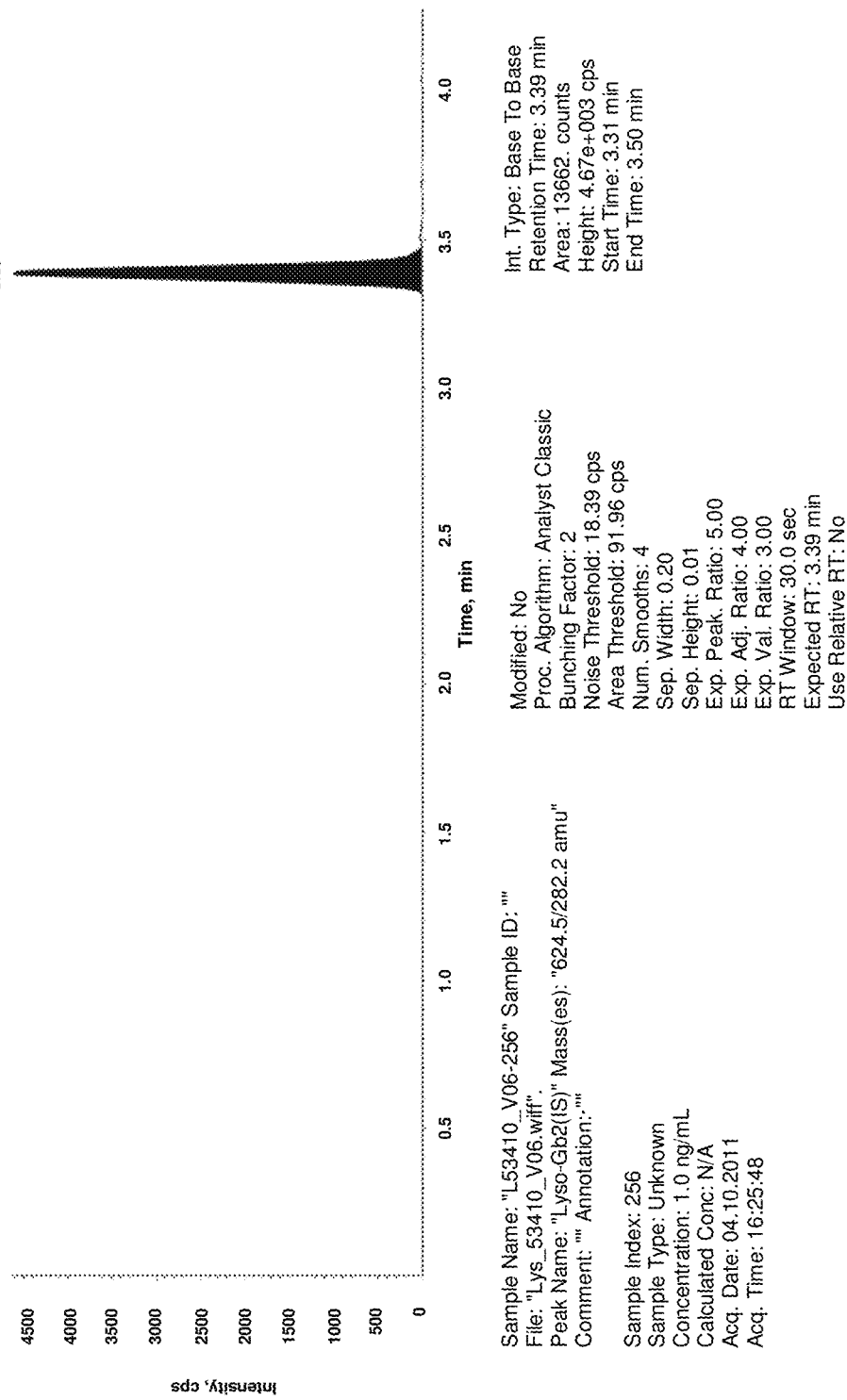
Fig. 8C (3)

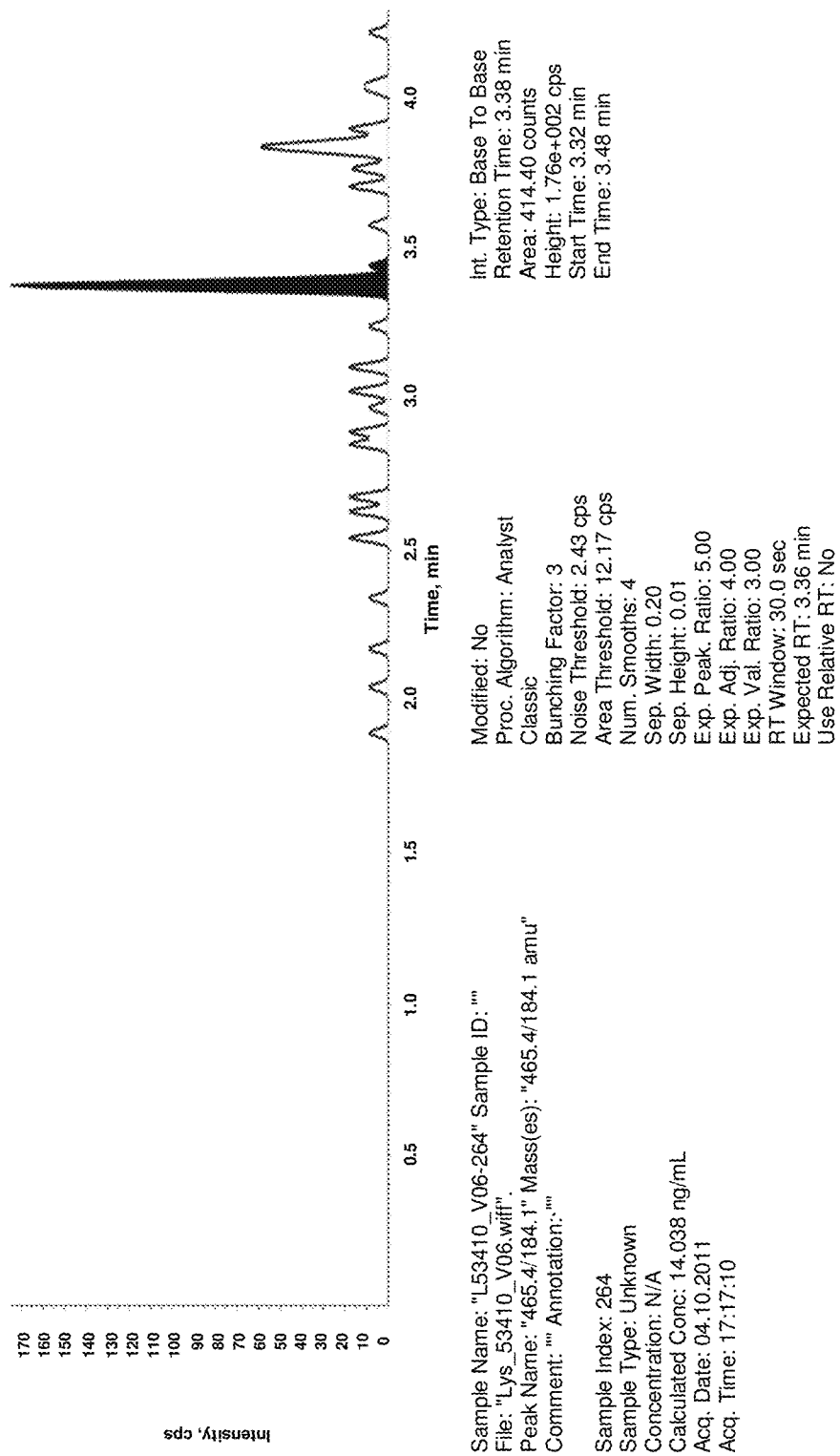
Fig. 8D (1)

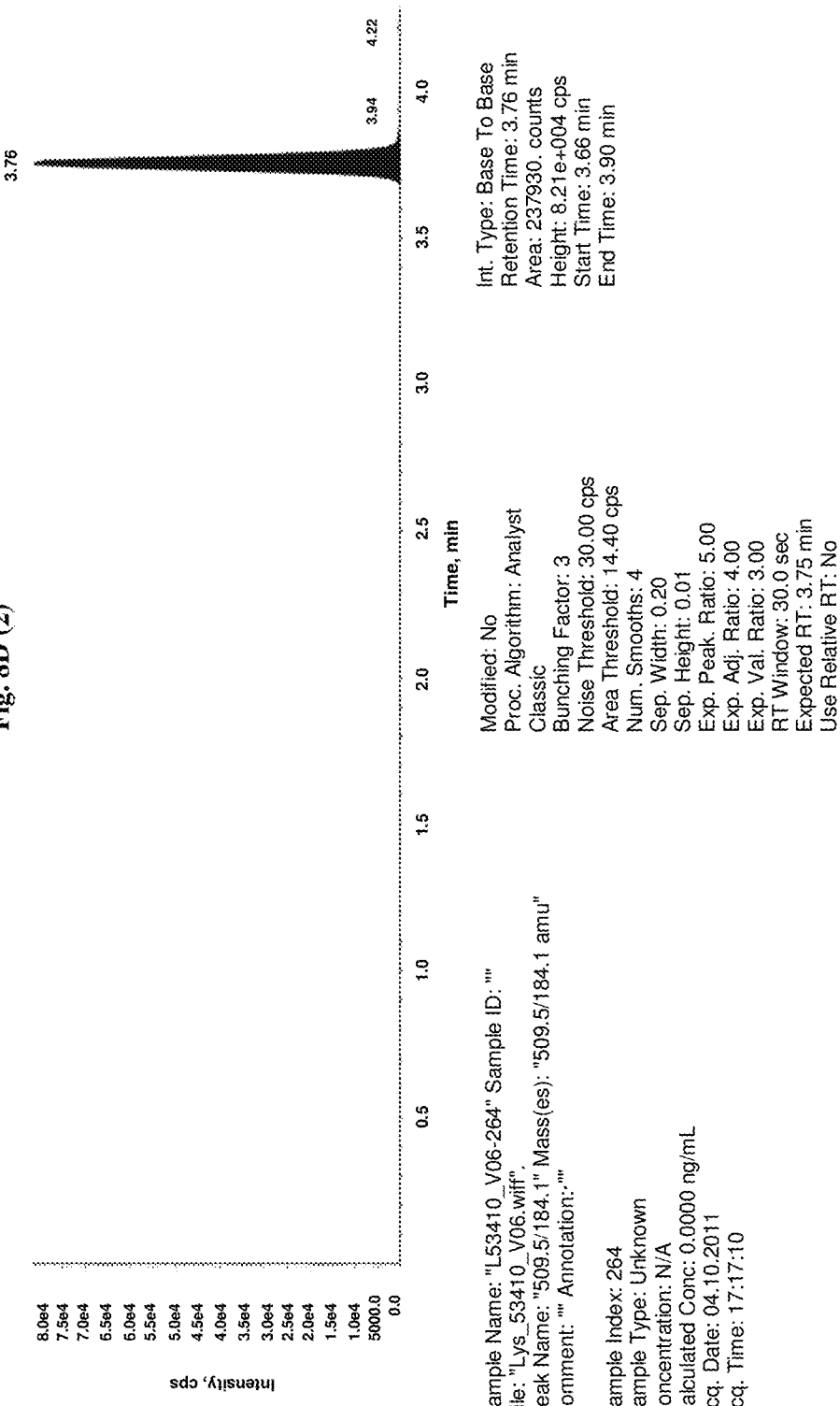
Fig. 8D (2)

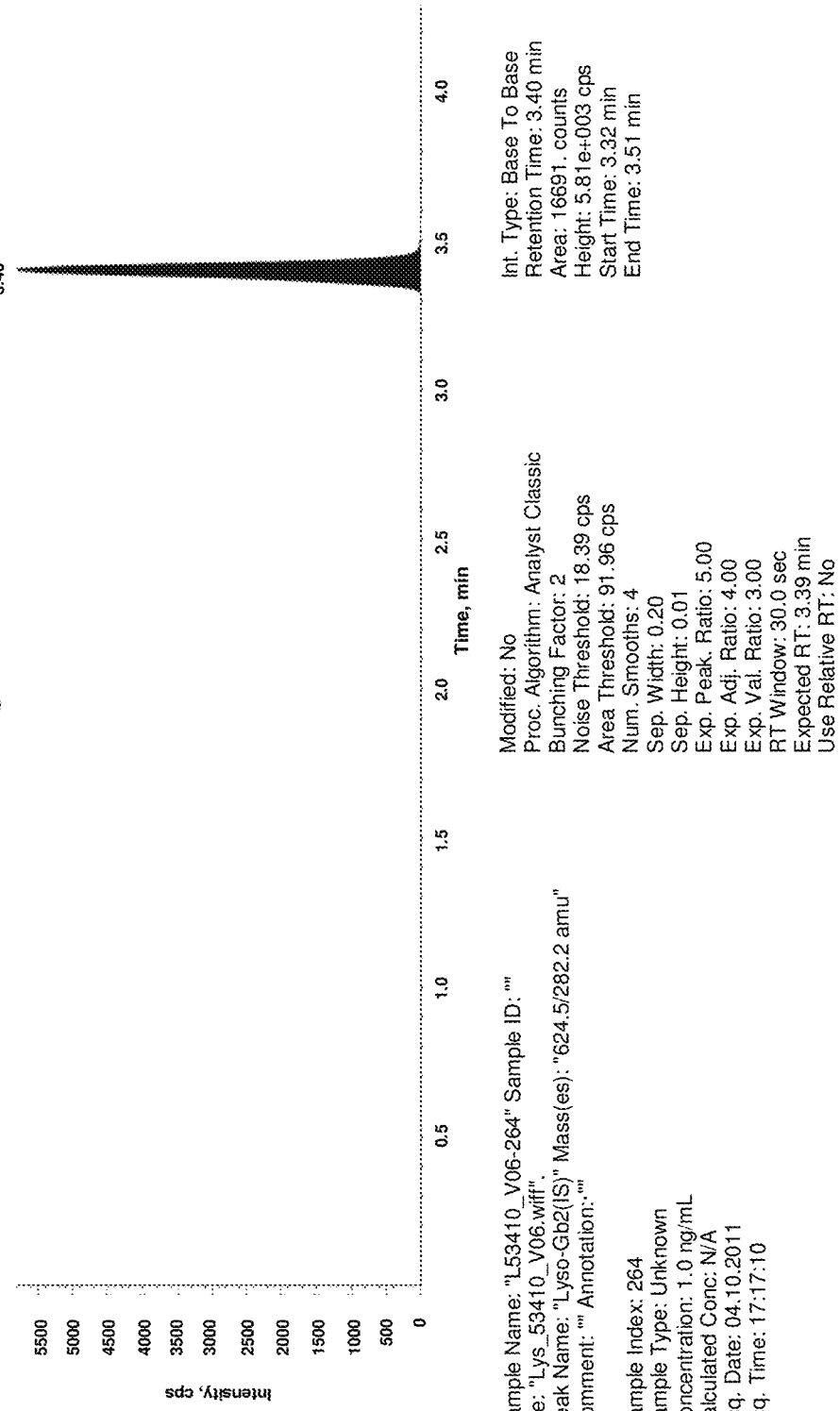
Fig. 8D (3)

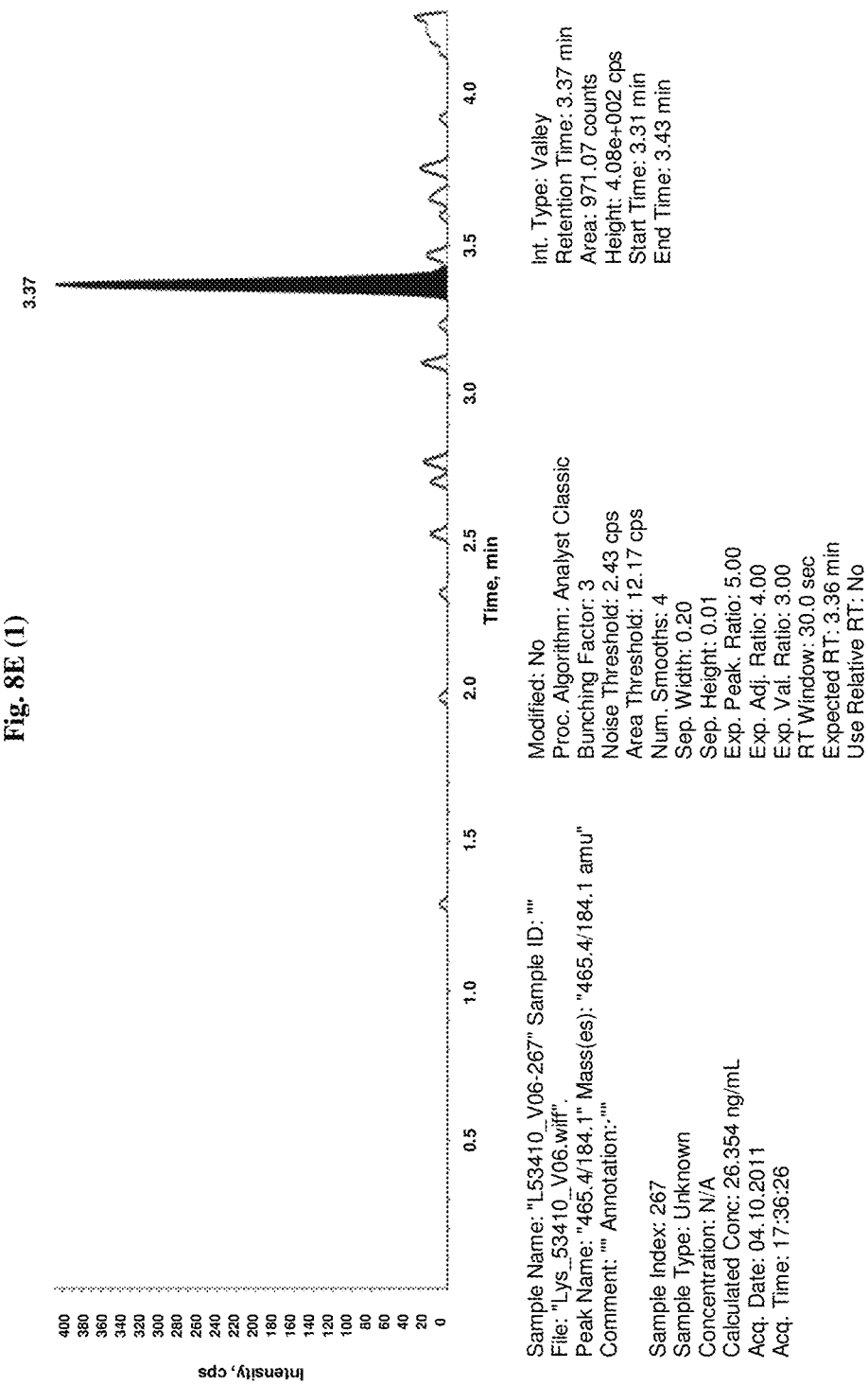
Fig. 8E (1)

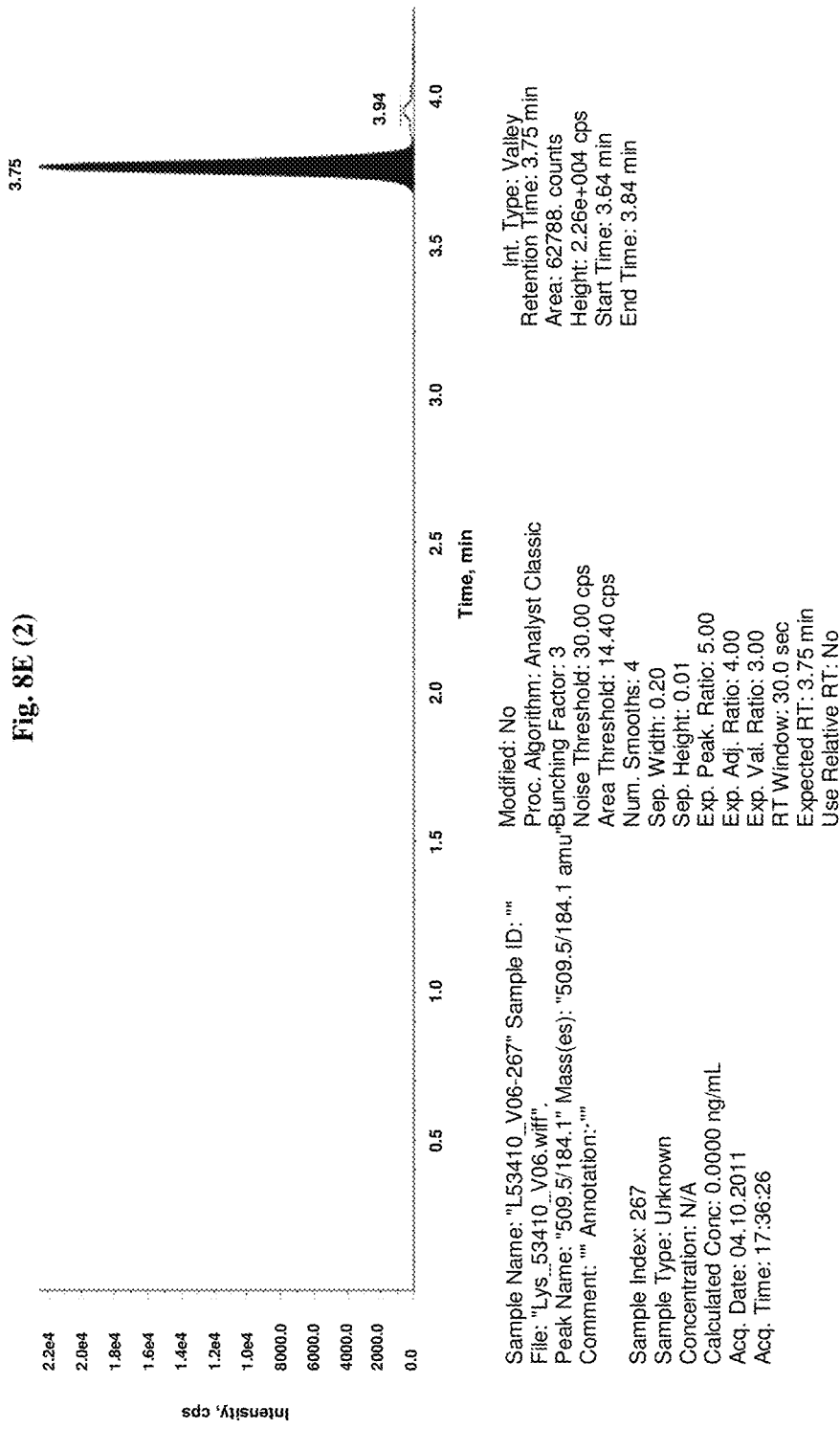
Fig. 8E (2)

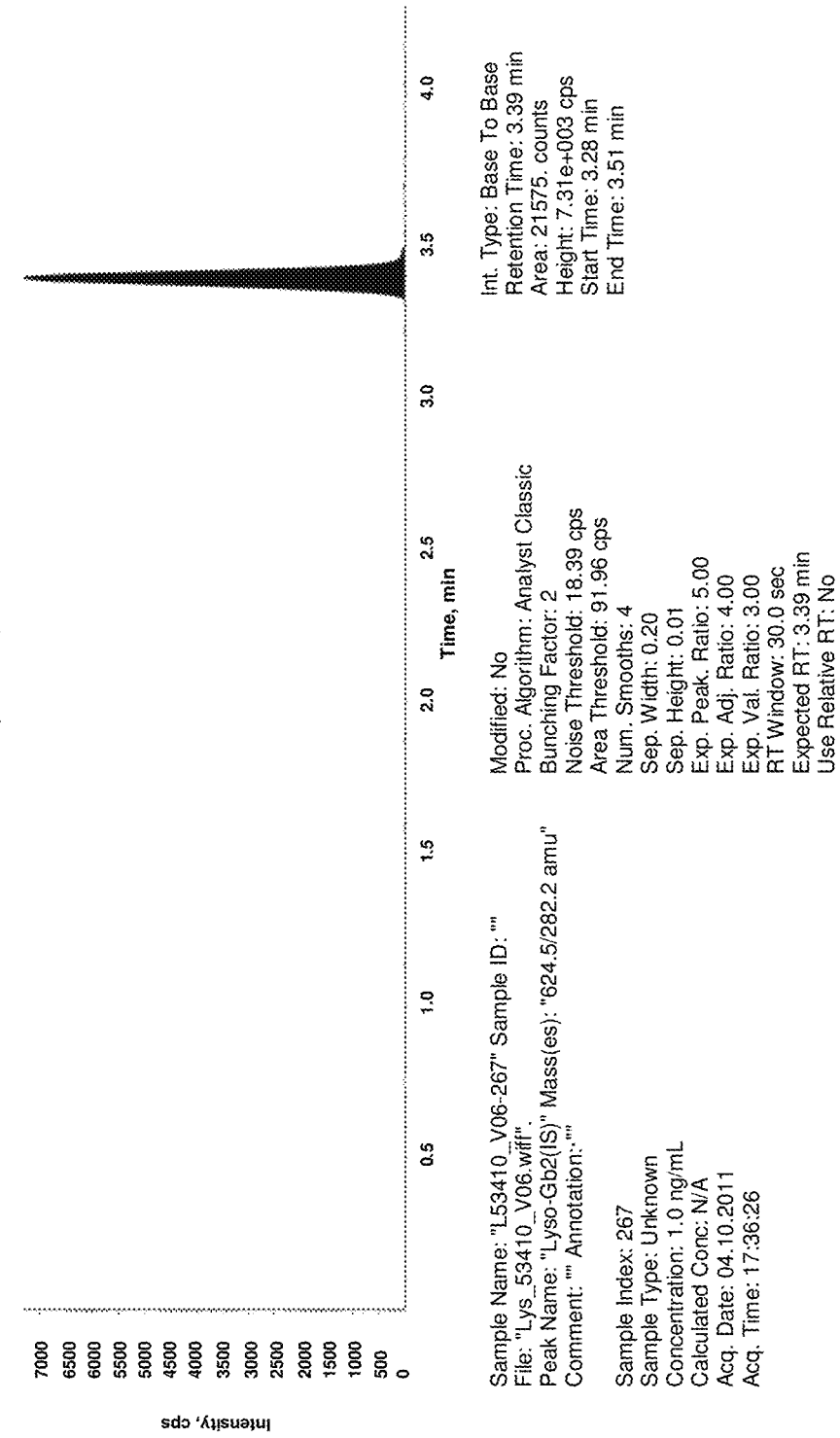
Fig. 8E (3)

METHOD FOR THE DIAGNOSIS OF NIEMANN-PICK DISEASE

The present invention is a continuation of U.S. patent application Ser. No. 15/700,949, filed Sep. 11, 2017, which is a continuation of U.S. patent application Ser. No. 14/358,669, filed May 15, 2014, which is a 371 application of International Application No. PCT/EP2012/004756, filed Nov. 15, 2012, which claims priority to European Patent Application No. 11009062.8, filed Nov. 15, 2011, which are related to a method for diagnosing Niemann-Pick disease in a subject, a method for diagnosing Niemann-Pick disease, Niemann-Pick disease type A and B or Niemann-Pick disease type C in a subject, a method for determining the course of Niemann-Pick disease in a subject, a method of determining the effectiveness of a compound for the treatment of Niemann-Pick disease, use of mass spectrometric analysis for the detection of a biomarker, use of a biomarker for the diagnosis of Niemann-Pick disease, Use of a ratio of a level of a biomarker present in a sample from the subject to a level of an at least one additional biomarker present in a sample from the subject for use in a method of diagnosis of Niemann-Pick disease, and a kit for determining the presence of a biomarker in a sample from a subject.

Lysosomal storage diseases, also referred to herein as lysosomal storage disorders or LSDs, are a group of rare inherited metabolic disorders that result from defects in lysosomal function. LSDs result when a specific organelle in the body's cells—the lysosome—malfunctions. Some of the more prominent lysosomal storage diseases are Gaucher's disease and Fabry disease.

LSDs are caused by lysosomal dysfunction usually as a consequence of deficiency of a single enzyme required for the metabolism of lipids, glycoproteins or so-called mucopolysaccharides. Individually, LSDs occur with frequencies of about 1:10,000 to 1:250,000, however, as a group the incidence is about 1:5,000. Most of these disorders are autosomal recessively inherited; however, a few are X-linked inherited, such as Fabry disease and Hunter syndrome (MPS II).

Like other genetic diseases, individuals typically inherit lysosomal storage diseases from their parents. Although each disorder results from different gene mutations that translate into a deficiency in enzyme activity, they all share a common biochemical characteristic—nearly all lysosomal disorders originate from an abnormal accumulation of substances inside the lysosome. Lysosomal storage diseases affect mostly children and they often die at a young and unpredictable age, many within a few months or years of birth. Many other children die of this disease following years of suffering from various symptoms of their particular disorder.

The symptoms of lysosomal storage disease vary, depending on the particular disorder and other variables like the age of onset, and can be mild to severe. They can include developmental delay, movement disorders, seizures, dementia, deafness and/or blindness. Some people with Lysosomal storage disease have enlarged livers (hepatomegaly) and enlarged spleens (splenomegaly), pulmonary and cardiac problems, and bones that develop abnormally.

There are no causative cures for lysosomal storage diseases and treatment is mostly symptomatic, although bone marrow transplantation and enzyme replacement therapy (ERT) have been used for some indications with good success. In addition, umbilical cord blood transplantation is being performed at specialized centers for a number of these diseases. In addition, substrate reduction therapy (SRT), a method used to decrease the accumulation of storage material, is currently being evaluated for some of these diseases. Furthermore, chaperone therapy, a technique used to stabilize the defective enzymes produced by patients, is being examined for certain of these disorders. Gene therapy constitutes a further option for the treatment of these diseases.

Niemann-Pick disease is a disease of a subgroup of LSDs, called sphingolipidoses or lipid storage disorders in which harmful quantities of fatty substances, or lipids, accumulate in the spleen, liver, lungs, bone marrow, and brain.

Niemann-Pick disease is inherited in an autosomal recessive pattern, which means both copies, or alleles, of the gene must be mutated (altered in such a way that function is impaired, in contrast to a polymorphism, in which the nucleotide sequence is altered but causes no functional disruption) for a person to be affected by the disorder. Most often, the parents of a child with an autosomal recessive disorder are not affected but are carriers of one copy of the altered gene.

In 1961, the following classification was introduced:
Niemann-Pick disease type A: classic infantile;
Niemann-Pick disease type B: visceral;
Niemann-Pick disease, type C: subacute/juvenile; and
Niemann-Pick disease type D: Nova Scotian.

Now that the genetics are better understood, the condition can be classified as follows:
Niemann-Pick disease, SMPD1-associated, which includes types A and B; and
Niemann-Pick disease, type C, which includes types C1 and C2 and Niemann-Pick disease, type D, which is caused by the same gene as type C1.

Mutations in the SMPD1 gene cause Niemann-Pick disease types A and B, and mutations in NPC1 and NPC2 cause Niemann-Pick disease, type C, which is also referred to herein preferably as NPC.

Type D was originally separated from Type C to delineate a group of patients with otherwise identical disorders who shared a common Nova Scotian ancestry. Patients in this group are now known to share a specific mutation in the NPC 1 gene, and NPC is now used to embrace both groups.

In the classic infantile type A variant, a missense mutation causes complete deficiency of sphingomyelinase. Sphingomyelin is a component of cell membrane including the organellar membrane and so the enzyme deficiency blocks degradation of lipid, resulting in the accumulation of sphingomyelin within lysosomes in the macrophage-monocyte phagocyte lineage. Affected cells become enlarged, sometimes up to 90 micrometres in diameter, secondary to the distention of lysosomes with sphingomyelin and cholesterol. Histology demonstrates lipid laden macrophages in the marrow, as well as "sea-blue histiocytes" on pathology. Numerous small vacuoles of relatively uniform size are created, imparting a foamy appearance to the cytoplasm.

Niemann-Pick type C is a lysosomal storage disease associated with mutations in NPC1 and NPC2 genes. Niemann-Pick Type C strikes an estimated 1:150,000 people. Approximately 50% of cases present before 10 years of age, but manifestations may first be recognized as late as the sixth decade.

To date a definitive diagnosis of Niemann-Pick disease type C can only be made by assaying cultured fibroblasts for cholesterol esterification and staining for unesterified cholesterol with filipin. The fibroblasts are grown from a small skin biopsy taken from a patient with suspected Niemann-Pick disease type C together with genetic confirmation. Since numerous different mutations may be the cause of a particular lysosomal storage disease the sequencing of the NPC1 or NPC2 genes is applied in Niemann-Pick disease type C in order to confirm the diagnosis.

Although there are attempts to apply diagnosis methods based on associated biochemical abnormalities there is an unmet need for a simple biochemical test exhibiting highly specific and highly sensitive detection of said lysosomal storage disease at an early stage, monitoring progression of the disease and early monitoring the efficacy of applied therapies.

Therefore, the identification of biomarkers for the early detection and diagnosis of Niemann-Pick disease, Niemann-Pick disease type A/B and/or Niemann-Pick disease type C holds great promise to improve the clinical outcome of patients. It is especially important for patients with vague or no symptoms or to detect patients which fail to respond to a therapy.

A biomarker should be technically feasible in many hands, easy to measure; useful, with a consistent, relative magnitude between affected and controls, or treated and untreated; reliable, and accurate clinically, and classifiable as strongly predictive or prognostic.

Today, no biomarker for diagnosing Niemann-Pick disease, more particularly to differentially diagnose Niemann-Pick disease type A and B, and Niemann-Pick disease type C is available.

In Gaucher's disease, another LSD, some lysosomal enzymes, used as indirect biomarkers, were found to be elevated, including tartrate-resistant acid phosphatase, hexosaminidase, and a human chitinase, chitotriosidase. Thus there are attempts to monitor the reduction of storage cells in tissues by measurement of such surrogate markers of Gaucher cells like chitotriosidase and CCL18 (C. E. Hollak et al. Marked elevation of plasma chitotriosidase activity. A novel hallmark of Gaucher disease, J. Clin. Invest. 93 (1994) 1288-1292; R. G. Boot et al. Marked elevation of the chemokine CCL18/PARC in Gaucher disease: a novel surrogate marker for assessing therapeutic intervention, Blood 103 (2004) 33-39). However, beside other disadvantages in the use of chitotriosidase as a biomarker for Gaucher's disease, said enzyme accumulates independent of a direct link to the pathology of Gaucher's disease. Furthermore, up to 35% of given ethnicities demonstrate a defect of the gene coding for chitotriosidase resulting in an artificially reduced or unmeasurable chitotriosidase activity.

The use of primary storage molecules as biomarker was assessed for glucosyl ceramide (Gb1) in plasma of Gaucher's disease patients and compared to the level of Gb1 in healthy individuals (Groener et al. Biochim Biophys Acta. 2008 January-February; 1781(1-2):72-8. Epub 2007 Dec. 5.; Plasma glucosylceramide and ceramide in type 1 Gaucher disease patients: correlations with disease severity and response to therapeutic intervention; Groener J E et al.). Nevertheless, although Gb1 measured in said study was increased in plasma of said patients, said increase of Gb1 was not prominent and thus the specificity and the sensitivity of the method were low showing that Gb1 is not applicable as a biomarker for Gaucher's disease.

Already in 1989 Rosengren et al. (Lysosulfatide (galactosylsphingosine-3-O-sulfate) from metachromatic leukodystrophy and normal human brain, Rosengren B, Fredman P, Mansson J E, Svennerholm L.; J Neurochem. 1989 April; 52(4):1035-41.) showed that in lipidoses not only the catabolism of the major sphingolipid but also its lyso-compound is affected. Nevertheless, said study concluded that the lyso-compounds do not play a key role in the pathogenetic mechanisms in the sphingolipidoses. Thus, said lyso-compounds might not be suitable biomarkers for diagnosis of sphingolipidoses such as Gaucher's disease.

It is important to note that until today no use of a highly specific and highly sensitive biomarker and no method for the diagnosis of Niemann-Pick disease, particularly for the differential diagnosis of Niemann-Pick disease type A and B, Niemann-Pick disease type C, and Niemann-Pick disease type C carrier, is available beside the methods described above that exhibit an unsatisfactory limit of detection, sensitivity and/or specificity and thus proved to be unsuitable for clinical application and which methods do not allow for differential diagnosis of different types of Niemann-Pick disease, such as Niemann-Pick disease type A and B, and Niemann-Pick disease type C.

Accordingly, there is need for a fast, simple and more importantly reliable method for the diagnosis of Niemann-Pick disease, particularly the differential diagnosis of Niemann-Pick disease type A and B, and Niemann-Pick disease type C and Niemann-Pick disease type C carrier.

In the light of the above, the problem underlying the present invention is to provide a method for the diagnosis of Niemann-Pick disease, particularly the diagnosis of Niemann-Pick disease type A and B, and Niemann-Pick disease type C and Niemann-Pick disease type C carrier.

It is a further problem underlying the present invention to provide a method for the differential diagnosis of a first group of Niemann-Pick disease consisting of Niemann-Pick disease type A and B, a second group of Niemann-Pick disease consisting of Niemann-Pick disease type C and a third group of Niemann-Pick disease consisting of Niemann-Pick disease type C carrier.

It is a still further problem underlying the present invention to provide a method which allows to determine whether or not the subject is suffering from Niemann-Pick disease type C, Niemann-Pick disease type A and B and/or from Niemann-Pick disease type C carrier or whether or not the subject is at risk of suffering from Niemann-Pick disease type C, Niemann-Pick disease type A and B and/or from Niemann-Pick disease type C carrier.

A further problem underlying the present invention is to provide a method for determining the course and prognosis of Niemann-Pick disease, particularly the diagnosis of Niemann-Pick disease type A and B, and Niemann-Pick disease type C and Niemann-Pick disease type C carrier.

A still further problem underlying the present invention is to provide a method for determining rather quickly the effectiveness of at least one treatment applied to a subject being positively tested for suffering from or being at risk of developing Niemann-Pick disease, particularly Niemann-Pick disease type A and B or Niemann-Pick disease type C and Niemann-Pick disease type C carrier.

A further problem underlying the present invention is to provide a method for determining the effectiveness of a compound for the treatment of Niemann-Pick disease, particularly Niemann-Pick disease type A and B and/or Niemann-Pick disease type C and Niemann-Pick disease type C carrier.

Another problem underlying the present invention is to provide a biomarker which allows the specific and sensitive diagnosis of Niemann-Pick disease, particularly specific and sensitive diagnosis of Niemann-Pick disease type A and B, and Niemann-Pick disease type C and Niemann-Pick disease type C carrier.

A still further problem underlying the present invention is a kit which comprises a compound which interacts with a biomarker which is specific and sensitive for Niemann-Pick disease, particularly for Niemann-Pick disease type A and B and/or Niemann-Pick disease type C and Niemann-Pick disease type C carrier.

These and other problems are solved by the subject matter of the attached independent claims. Preferred embodiments may be taken from the attached dependent claims.

These claims are recited in the following as embodiments. It will be acknowledged that further embodiments may result from the disclosure of the instant specification which is insofar not limited to the embodiments being a recitation of the claims.

Embodiment 1

A method for diagnosing Niemann-Pick disease in a subject comprising a step a), wherein the step a) comprises detecting a biomarker in a sample from the subject.

Embodiment 2

The method according to embodiment 1, wherein the method comprises a step b) wherein the step b) comprises determining a level of the biomarker present in the sample.

Embodiment 3

The method according to any one of embodiments 1 or 2, wherein the level of the biomarker is indicative whether or not the subject is suffering from Niemann-Pick disease or whether or not the subject is at risk of suffering from Niemann-Pick disease.

Embodiment 4

The method according to any one of embodiments 1 to 3, wherein the sample from the subject is a sample from a subject who has previously been treated for Niemann-Pick disease or a sample from a subject who has previously been diagnosed for Niemann-Pick disease.

Embodiment 5

The method according to any one of embodiments 1 to 3, wherein the sample from the subject is a sample from a subject who has not previously been treated for Niemann-Pick disease or a sample from a subject who has not been previously diagnosed for Niemann-Pick disease.

Embodiment 6

The method according to any one of embodiments 1 to 5, wherein the method comprises
a step c), wherein the step c) comprises applying, maintaining, reducing, elevating or not applying a therapy based on whether the subject is suffering from Niemann-Pick disease or is at risk of suffering from Niemann-Pick disease.

Embodiment 7

The method according to any one of embodiments 1 to 6, wherein the method comprises
a step d), wherein the step d) comprises detecting the biomarker in a sample from the subject after a therapy has been applied, maintained, reduced, elevated or not applied in step c).

Embodiment 8

The method according to any one of embodiments 1 to 7, wherein the method comprises
a step e), wherein the step e) comprises determining a level of the biomarker in the sample from the subject after a therapy has been applied, maintained, reduced, elevated or not applied in step c).

Embodiment 9

The method according to embodiment 8, wherein the method comprises
a step f), wherein the step f) comprises determining whether the level of the biomarker determined in step b) is lower than the level of the biomarker determined in step e).

Embodiment 10

The method according to embodiment 9, wherein the method comprises
a step g), wherein the step g) comprises applying, maintaining, reducing, elevating or not applying a therapy based on step f).

Embodiment 11

The method according to any one of embodiments 1 to 10, wherein the biomarker is selected from the group comprising free lyso-sphingomyelin and compound 509.

Embodiment 12

The method according to any one of embodiments 1 to 11, wherein the biomarker is free lyso-sphingomyelin.

Embodiment 13

The method according to any one of embodiments 1 to 11, wherein the biomarker is compound 509.

Embodiment 14

The method according to any one of embodiments 1 to 13, wherein the method comprises detecting at least one additional biomarker in a or in the sample from the subject.

Embodiment 15

The method according to embodiment 14, wherein the method comprises determining the level of the at least one additional biomarker in a or in the sample from the subject.

Embodiment 16

The method according to any one of embodiments 14 to 15, wherein the at least one additional biomarker is selected from the group comprising free lyso-sphingomyelin and compound 509, and wherein the at least one additional biomarker is different from the bio marker.

Embodiment 17

The method according to any one of embodiments 14 to 16, wherein the biomarker is compound 509 and wherein the at least one additional biomarker is free lyso-sphingomyelin.

Embodiment 18

The method according to any one of embodiments 14 to 16, wherein the biomarker is free lyso-sphingomyelin and wherein the at least one additional biomarker is compound 509.

Embodiment 19

The method according to any one of embodiments 1 to 18, wherein the method comprises determining the level of free lyso-sphingomyelin and compound 509 in a or in the sample.

Embodiment 20

The method according to any one of embodiments 14 to 19, preferably 17 to 19, wherein the method comprises
a step h), wherein the step h) comprises determining the ratio of the level of the biomarker in a or in the sample to the level of the at least one additional biomarker in a or in the sample.

Embodiment 21

The method according to embodiment 20, wherein the ratio of the level of the biomarker to the level of the at least one additional biomarker, preferably as determined in step h), is indicative whether or not the subject is suffering from Niemann-Pick disease or whether or not the subject is at risk of suffering from Niemann-Pick disease.

Embodiment 22

The method according to any one of embodiments 1 to 21, wherein the method comprises detecting free lyso-sphingomyelin and compound 509 in a or in the sample.

Embodiment 23

The method according to any one of embodiments 1 to 22, wherein the biomarker and/or the at least one additional biomarker is detected by means of immunoassay, mass spectrometric analysis, biochip array, functional nucleic acids and/or a fluorescent derivative of the biomarker and/or a fluorescent derivative of the at least one additional biomarker.

Embodiment 24

The method according to embodiment 23, wherein the biomarker is detected by means of mass spectrometric analysis.

Embodiment 25

The method according to embodiment 24, wherein mass spectrometric analysis is selected from the group comprising SELDI, MALDI, MALDI-Q TOF, MS/MS, TOF-TOF and ESI-O-TOF.

Embodiment 26

The method according to embodiment 25, wherein the mass spectrometric analysis comprises or uses MS/MS.

Embodiment 27

The method according to any one of embodiments 1 to 26, wherein the method comprises protein precipitation and/or HPLC.

Embodiment 28

The method according to any one of embodiments 1 to 27, wherein the method comprises protein precipitation, HPLC and MS/MS.

Embodiment 29

The method according to any one of embodiments 1 to 28, wherein the subject is a human.

Embodiment 30

The method according to any one of embodiments 1 to 29, wherein Niemann-Pick disease is selected from the group comprising Niemann-Pick disease type A and B, Niemann-Pick disease type C, and Niemann-Pick disease type C carrier.

Embodiment 31

The method according to any one of embodiments 1 to 30, wherein step d) comprises detecting the biomarker in a sample comprises subjecting the sample to a protein precipitation step, precipitating protein from the sample, providing a supernatant of the sample, subjecting the supernatant of the sample to HPLC and MS/MS and determining the level of the biomarker and/or the at least one additional biomarker that is/are present in the supernatant of the sample.

Embodiment 32

A method for diagnosing Niemann-Pick disease in a subject, wherein the method comprises the following steps:
i) adding an internal standard to a sample from the subject, wherein the sample from the subject is selected from the group comprising plasma, serum and blood;
ii) optionally mixing the sample containing the internal standard;
iii) subjecting the sample to a protein precipitation step, whereby protein from the sample is precipitated and a first supernatant of the sample is provided;
iv) optionally subjecting the first supernatant of the sample or at least a part thereof to a first separation step which provides a second supernatant, whereby preferably the first separation step is a step of centrifugation;
v) subjecting the first supernatant and/or the second supernatant, or at least a part thereof, to a second separation step, wherein the second separation step comprises injecting at least a part of the first supernatant and/or at least a part of the second supernatant into an HPLC-MS/MS system and using an HPLC column with a gradient from acidic water to acetonitrile/acetone; wherein the HPLC column is preferably an HPLC column selected from the group comprising a C8 HPLC column and a C18 HPLC column, and wherein the second separation step provides a separated sample;
vi) subjecting the separated sample to MS/MS, wherein MS/MS comprises electrospray ionization and Multiple Reacting Monitoring;

and comprising
a step a), wherein the step a) comprises detecting a biomarker in a sample from the subject,
and optionally
a step b), wherein the step b) comprises determining a level of the biomarker present in the sample,
wherein the biomarker is free lyso-sphingomyelin, and
wherein the method is preferably a method according to any one of embodiments 1 to 31;

Embodiment 33

A method for diagnosing Niemann-Pick disease in a subject, wherein the method comprises the following steps:
i) adding an internal standard to a sample from the subject, wherein the sample from the subject is selected from the group comprising plasma, serum and blood;
ii) optionally mixing the sample containing the internal standard;
iii) subjecting the sample to a protein precipitation step, whereby protein from the sample is precipitated and a first supernatant of the sample is provided;
iv) optionally subjecting the first supernatant of the sample or at least a part thereof to a first separation step which provides a second supernatant, whereby preferably the first separation step is a step of centrifugation;
v) subjecting the first supernatant and/or the second supernatant, or at least a part hereof, to a second separation step, wherein the second separation step comprises injecting at least a part of the first supernatant and/or at least a part of the second supernatant into an HPLC-MS/MS system and using an HPLC column with a gradient from acidic water to acetonitrile/acetone; wherein the HPLC column is preferably an HPLC column selected from the group comprising a C8 HPLC column and a C18 HPLC column, and wherein the second separation step provides a separated sample;
vi) subjecting the separated sample to MS/MS, wherein MS/MS comprises electrospray ionization and Multiple Reacting Monitoring;
and comprising
a step a), wherein the step a) comprises detecting a biomarker in a sample from the subject,
and optionally
a step b), wherein the step b) comprises determining a level of the biomarker present in the sample,
wherein the biomarker is compound 509, and
wherein the method is preferably a method according to any one of embodiments 1 to 31.

Embodiment 34

A method for diagnosing Niemann-Pick disease in a subject, wherein the method comprises the following steps:
i) adding an internal standard to a sample from the subject, wherein the sample from the subject is selected from the group comprising plasma, serum and blood;
ii) optionally mixing the sample containing the internal standard;
iii) subjecting the sample to a protein precipitation step, whereby protein from the sample is precipitated and a first supernatant of the sample is provided;
iv) optionally subjecting the first supernatant of the sample or at least a part thereof to a first separation step which provides a second supernatant, whereby preferably the first separation step is a step of centrifugation;
v) subjecting the first supernatant and/or the second supernatant, or at least a thereof, to a second separation step, wherein the second separation step comprises injecting at least a part of the first supernatant and/or at least a part of the second supernatant into an HPLC-MS/MS system and using an HPLC column with a gradient from acidic water to acetonitrile/acetone; wherein the HPLC column is preferably an HPLC column selected from the group comprising a C8 HPLC column and a C18 HPLC column, and wherein the second separation step provides a separated sample;
vi) subjecting the separated sample to MS/MS, wherein MS/MS comprises electrospray ionization and Multiple Reacting Monitoring;
and comprising
a step a), wherein the step a) comprises detecting a biomarker in a sample from the subject, and detecting at least one additional biomarker in a sample from the subject
and optionally
a step b), wherein the step b) comprises determining a level of the biomarker present in the sample
and a level of the at least one additional biomarker present in the sample
wherein the biomarker is free lyso-sphingomyelin,
wherein the at least one additional biomarker is compound 509, and
wherein the method is preferably a method according to any one of embodiments 1 to 31.

Embodiment 35

The method according to embodiment 34, wherein the method comprises
a step c), wherein the step c) comprises determining the ratio of the level of compound 509 to the level of free lyso-sphingomyelin as determined in step b).

Embodiment 36

The method according to embodiment 35, wherein the ratio of the level of compound 509 to the level of free lyso-sphingomyelin is indicative of whether or not the subject is suffering from Niemann-Pick disease or of whether or not the subject is at risk of suffering from Niemann-Pick disease.

Embodiment 37

A method for diagnosing Niemann-Pick disease, Niemann-Pick disease type A and B or Niemann-Pick disease type C in a subject, wherein the method comprises the following steps:
i) adding an internal standard to a sample from the subject, wherein the sample form the subject is selected from the group comprising plasma, serum and blood;
ii) optionally mixing the sample containing the internal standard;
iii) subjecting the sample to a protein precipitation step, whereby protein from the sample is precipitated and a first supernatant of the sample is provided;
iv) optionally subjecting the first supernatant of the sample or at least a part thereof to a first separation step which provides a second supernatant, whereby preferably the first separation step is a step of centrifugation;
v) subjecting the first supernatant and/or the second supernatant, or a part thereof, to a second separation step, wherein the second separation step comprises injecting at least a part of the first supernatant and/or at least a part of the second supernatant into an HPLC-MS/MS system and using an HPLC column with a gradient form acidic water to acetonitrile/acetone; wherein the HPLC column is preferably an HPLC column selected from the group comprising a C8 HPLC column and a C18 HPLC column, and wherein the second separation step provides a separated sample;

vi) subjecting the separated sample to MS/MS, wherein MS/MS comprises electrospray ionization and Multiple Reacting Monitoring;

and comprising a step a), wherein the step a) comprises detecting a biomarker in a sample from the subject, and detecting at least one additional biomarker in a sample from the subject; and a step b), wherein the step b) comprises determining a level of the biomarker present in the sample and a level of the at least one additional biomarker present in the sample; and a step c), wherein the step c) comprises determining the ratio of the level of the at least one additional biomarker to the level of the biomarker as determined in step b);

wherein if the level of the at least one additional biomarker is lower than or as high as 0.031 ng/ml this is indicative that the subject is not suffering from Niemann-Pick disease;

wherein if the level of the at least one additional biomarker is higher than 0.031 ng/ml this is indicative that the subject is suffering from Niemann-Pick disease;

wherein if the level of the at least one additional biomarker is higher than 0.031 ng/ml and is lower than or as high as 1.7 ng/ml this is indicative that the subject is suffering from Niemann-Pick disease type C carrier; and wherein if the level of the at least one additional biomarker is higher than 1.7 ng/ml this is indicative that the subject is suffering from Niemann-Pick disease selected from the group consisting of Niemann-Pick disease type A or B and Niemann-Pick disease type C; and wherein if the level of the at least one additional biomarker is higher than 1.7 ng/ml and the ratio of the level of the at least one additional biomarker to the level of the biomarker is higher than 0.045 this is indicative that the subject is suffering from Niemann-Pick disease type A and B; and wherein if the level of the at least one additional biomarker is higher than 1.7 ng/ml and the ratio of the level of the at least one additional biomarker to the level of the biomarker is lower than or as high as 0.045 this is indicative that the subject is suffering from Niemann-Pick disease type C; and wherein the biomarker is free lyso-sphingomyelin;

wherein the at least one additional biomarker is compound 509; and wherein the method is preferably a method according to any one of embodiments 1 to 31;

Embodiment 38

The method according to any one of embodiments 31 to 37, wherein the internal standard comprises D5-fluticasone proprionate and/or lyso-Gb2.

Embodiment 39

The method according to any one of embodiments 1 to 38, wherein step b), step c) and/or step e) comprises comparing the level of the biomarker in the sample and/or the level of the at least one additional biomarker in the sample and/or the ratio of the level of the biomarker to the level of the at least one additional biomarker in the sample from the subject with a cut-off value.

Embodiment 40

The method according to any one of embodiments 1 to 39, preferably 39, wherein if the level of the biomarker in the sample from the subject is higher than the cut-off value this is indicative that the subject is suffering from Niemann-Pick disease or is at risk of suffering from Niemann-Pick disease.

Embodiment 41

The method according to any one of embodiments 1 to 39, preferably 39, wherein if the ratio of the level of the biomarker in the sample from the subject to the level of the at least one additional biomarker in the sample from the subject is higher than the cut-off value this is indicative that the subject is suffering from Niemann-Pick disease or is at risk of suffering from Niemann-Pick disease.

Embodiment 42

The method according to any one of embodiments 1 to 39, preferably 39, wherein if the level of the biomarker in the sample from the subject is lower than the cut-off value this is indicative that the subject is not suffering from or is not at risk of suffering from Niemann-Pick disease.

Embodiment 43

The method according to any one of embodiments 1 to 39, preferably 39, wherein if the ratio of the level of the biomarker to the level of the at least one additional biomarker in the sample from the subject is lower than the cut-off value this is indicative that the subject is not suffering from or is not at risk of suffering from Niemann-Pick disease.

Embodiment 44

The method according to any one of embodiments 1 to 43, wherein the cut-off value is selected such that a or the sensitivity for diagnosing Niemann-Pick disease in a subject is preferably from about 98.5% to 100%, more preferably 99.5% to 100%, and/or such that a or the specificity for diagnosing Niemann-Pick disease type C in a subject is from 99.4% to 100%, preferably 100%.

Embodiment 45

The method according to any one of embodiments 1 to 44, wherein step b) and/or step c) and/or step e) comprise(s) that
a level of the biomarker in said subject and/or
a level of the at least one additional biomarker
is/are compared
to a level of the biomarker and/or
to the level of the at least one additional biomarker detected in a sample from a control sample;
and/or that
the ratio of the level of the at least one additional biomarker to the level of the biomarker
is compared
to the ratio of the level of the at least one additional biomarker to the level of the biomarker detected in a sample from a control.

Embodiment 46

The method according to embodiment 45, wherein the control sample is a sample from a subject not having Niemann-Pick disease.

Embodiment 47

The method according to any one of embodiments 45 to 46, wherein if the level of the biomarker in the sample from the subject is higher than the level of the biomarker in the control sample this is indicative that the subject is suffering from and/or is at risk of suffering from Niemann-Pick disease.

Embodiment 48

The method according to any one of embodiments 1 to 46, wherein if the ratio of the level of the at least one additional biomarker in the sample from the subject to the level of the biomarker in the sample from the subject is higher than the ratio of the level of the at least one additional biomarker in the control sample to the level of the biomarker in the control sample, this is indicative that the subject is suffering from and/or is at risk of suffering from Niemann-Pick disease.

Embodiment 49

The method according to any one of embodiments 1 to 48, wherein Niemann-Pick disease is selected from the group comprising Niemann-Pick type A or B, Niemann-Pick type C, and Niemann-Pick type C carrier.

Embodiment 50

The method according to embodiment 49, wherein Niemann-Pick disease type C is selected from the group comprising Niemann-Pick disease type C1, Niemann-Pick disease type C2 and Niemann-Pick disease type D.

Embodiment 51

The method according to any one of embodiments 1 to 50, preferably to embodiment 50, wherein the sample from the subject is selected from the group comprising blood, a blood product, urine, saliva, cerebrospinal fluid, stool, tissue sample and lymph.

Embodiment 52

The method according to embodiment 51, wherein the sample from the sample from the subject is selected from the group comprising blood and a blood product.

Embodiment 53

The method according to any one of embodiments 51 to 52, wherein the blood product is selected from the group comprising serum and plasma.

Embodiment 54

The method according to any one of embodiments 1 to 53, preferably 53, wherein the method has a limit of detection for free lyso-sphingomyelin of 0.04 ng/ml.

Embodiment 55

The method according to any one of embodiments 1 to 54, wherein the method is for the diagnosis of Niemann-Pick disease type C carrier and wherein the biomarker is free lyso-sphingomyelin and the cut-off value is 6.5 ng/ml, and wherein the sample from the subject is preferably serum or plasma.

Embodiment 56

The method according to any one of embodiments 1 to 54, wherein the method is for the diagnosis of Niemann-Pick disease type C and wherein the biomarker is free lyso-sphingomyelin and the cut-off value is 9.23 ng/ml, and wherein the sample from the subject is preferably serum or plasma.

Embodiment 57

The method according to any one of embodiments 1 to 54, wherein the method is for the diagnosis of Niemann-Pick disease type A or B and wherein the biomarker is free lyso-sphingomyelin and the cut-off value is 59 ng/ml, and wherein the sample from the subject is preferably serum or plasma.

Embodiment 58

The method according to any one of embodiments 1 to 54, wherein the method is for the diagnosis of Niemann-Pick disease type C carrier and wherein the biomarker is compound 509 and the cut-off value is 0.031 ng/ml, and wherein the sample from the subject is preferably serum or plasma.

Embodiment 59

The method according to any one of embodiments 1 to 54, wherein the method is for the diagnosis of Niemann-Pick disease type C and wherein the biomarker is compound 509 and the cut-off value is 1.7 ng/ml, and wherein the sample from the subject is preferably serum or plasma.

Embodiment 60

The method according to any one of embodiments 1 to 54, wherein the method is for the diagnosis of Niemann-Pick disease type A or B and wherein the biomarker is compound 509 and the cut-off value is 5.0 ng/ml, and wherein the sample from the subject is preferably serum or plasma.

Embodiment 61

The method according to any one of embodiments 1 to 54, wherein the method is for the diagnosis of Niemann-Pick disease type C and wherein the ratio of the level of compound 509 in the sample from the subject to the level of free lyso-sphingomyelin biomarker in the sample from the subject is compared to a cut-off value, and wherein the cut-off value is 0.087, and wherein the sample from the subject is preferably serum or plasma.

Embodiment 62

The method according to any one of embodiments 1 to 54, wherein the method is for the diagnosis of Niemann-Pick disease type A or B and wherein the ratio of the level of compound 509 in the sample from the subject to the level of free lyso-sphingomyelin biomarker in the sample from the subject is compared to a cut-off value, and wherein the cut-off value is 0.045, and wherein the sample from the subject is preferably serum or plasma.

Embodiment 63

The method according to any one of embodiments 51 to 52, wherein the blood is whole blood.

Embodiment 64

The method according to embodiment 63, wherein the whole blood is collected on a dry blood filter card.

Embodiment 65

A method for determining the course of Niemann-Pick disease in a subject, wherein the method comprises a step a), wherein the a) comprises determining at several points in time a level of a biomarker present in a sample from the subject.

Embodiment 66

The method according to embodiment 65, wherein the biomarker is selected from the group comprising free lyso-sphingomyelin and compound 509.

Embodiment 67

The method according to any one of embodiments 65 to 66, wherein the biomarker is selected from the group consisting of free lyso-sphingomyelin and compound 509.

Embodiment 68

The method according to any one of embodiments 65 to 67, wherein the subject has been previously treated for Niemann-Pick disease and/or wherein the subject has been previously diagnosed for Niemann-Pick disease.

Embodiment 69

The method according to embodiment 68, wherein the subject has not been previously treated for Niemann-Pick disease and/or wherein the subject has not been previously diagnosed for Niemann-Pick disease.

Embodiment 70

The method according to any one of embodiments 65 to 69, wherein the method comprises
 a step b), wherein the step b) comprises applying, maintaining, reducing, elevating or not applying a therapy based on whether the subject is suffering from Niemann-Pick disease or is at risk of suffering from Niemann-Pick disease.

Embodiment 71

The method according to any one of embodiments 65 to 70, wherein the method comprises
 a step c), wherein the step c) comprises detecting the biomarker in a sample from the subject after a therapy has been applied, maintained, reduced, elevated or not applied in step b).

Embodiment 72

The method according to any one of embodiments 65 to 71, wherein the method comprises
 a step d), wherein the step d) comprises determining a level of the biomarker in the sample from the subject after a therapy has been applied, maintained, reduced, elevated or not applied in step b).

Embodiment 73

The method according to any one of embodiments 65 to 71, wherein the method comprises
 a step e), wherein the step e) comprises determining whether the level of the biomarker determined in step a) is lower than the level of the biomarker determined in step d).

Embodiment 74

The method according to any embodiment 73, wherein the method comprises
 a step f), wherein the step f) comprises applying, maintaining, reducing, elevating or not applying a therapy based on step e).

Embodiment 75

The method according to any one of embodiments 65 to 74, wherein the biomarker is free lyso-sphingomyelin.

Embodiment 76

The method according to any one of embodiments 65 to 74, wherein the biomarker is compound 509.

Embodiment 77

The method according to any one of embodiments 65 to 76, wherein the method comprises detecting at least one additional biomarker in the sample from the subject.

Embodiment 78

The method according to embodiment 77, wherein the method comprises determining the level of the at least one additional biomarker in the sample from the subject.

Embodiment 79

The method according to any one of embodiments 77 to 79, wherein the at least one additional biomarker is selected from the group comprising free lyso-sphingomyelin and compound 509, and wherein the at least one additional biomarker is different from the biomarker.

Embodiment 80

The method according to any one of embodiments 77 to 79, wherein the biomarker is compound 509 and wherein the at least one additional biomarker is free lyso-sphingomyelin.

Embodiment 81

The method according to any one of embodiments 65 to 80, wherein the method comprises determining the level of free lyso-sphingomyelin and compound 509.

Embodiment 82

The method according to any one of embodiments 77 to 81, preferably 80 to 81, wherein the method comprises
- a step h), wherein the step h) comprises determining the ratio of the level of the biomarker in the sample from the subject to the level of the at least one additional biomarker in the sample form the subject

Embodiment 83

The method according to embodiment 82, wherein the ratio of the level of the biomarker to the level of the at least one additional biomarker as determined in step h) is indicative whether or not the subject is suffering from Niemann-Pick disease or whether or not the subject is at risk of suffering from Niemann-Pick disease.

Embodiment 84

The method according to any one of embodiments 65 to 83, wherein the method comprises detecting free lyso-sphingomyelin and compound 509 in the sample from the subject.

Embodiment 85

The method according to any one of embodiments 65 to 84, wherein the biomarker and/or the at least one additional biomarker is detected by means of immunoassay, mass spectrometric analysis, biochip array, functional nucleic acids and/or a fluorescent derivative of free lyso-sphingomyelin.

Embodiment 86

The method according to embodiment 85, wherein the biomarker is detected by means of mass spectrometric analysis.

Embodiment 87

The method according to embodiment 86, wherein mass spectrometric analysis is selected from the group consisting of SELDI, MALDI, MALDI-Q TOF, MS/MS, TOF-TOF and ESI-O-TOF

Embodiment 88

The method according to embodiment 87, wherein the mass spectrometric analysis comprises or uses MS/MS MS/MS.

Embodiment 89

The method according to any one of embodiments 65 to 88, wherein the method comprises protein precipitation and/or HPLC.

Embodiment 90

The method according to any one of embodiments 65 to 89, wherein the method comprises protein precipitation, HPLC and MS/MS.

Embodiment 91

The method according to any one of embodiments 65 to 90, wherein the subject is a human.

Embodiment 92

The method according to any one of embodiments 65 to 91, wherein Niemann-Pick disease is selected from the group comprising Niemann-Pick disease type A and B, Niemann-Pick disease type C, and Niemann-Pick disease type C carrier.

Embodiment 93

The method according to any one of embodiments 65 to 92, wherein step d) comprises detecting the biomarker in a sample comprises subjecting the sample to a protein precipitation step, precipitating protein from the sample, providing a supernatant of the sample, subjecting the supernatant of the sample to HPLC and MS/MS and determining the level of the biomarker and/or the at least one additional biomarker that is/are present in the supernatant of the sample.

Embodiment 94

The method according to any one of embodiments 65 to 93, wherein Niemann-Pick disease type C is selected from the group comprising Niemann-Pick disease type C1, Niemann-Pick disease type C2 and Niemann-Pick disease type D.

Embodiment 95

A method for determining the effectiveness of at least one treatment applied to a subject being positively tested for suffering from or being at risk of suffering from Niemann-Pick disease comprising
- a step a), wherein the step a) comprises detecting at several points in time a level of a biomarker and/or of a at least one additional biomarker present in a sample from the subject.

Embodiment 96

The method according to embodiment 95, wherein the method comprises
- a step b), wherein the step b) comprises determining at several points in time a level of a biomarker and/or of a at least one additional biomarker present in a sample from the subject.

Embodiment 97

The method according to embodiment 96, wherein the method comprises
- a step c), wherein the step c) comprises determining the ratio of the level of the biomarker to the level of the at least one additional biomarker as determined in step b).

Embodiment 98

The method according to any one of embodiments 95 or 97, wherein the biomarker is selected from the group comprising free lyso-sphingomyelin and compound 509.

Embodiment 99

The method according to any one of embodiments 95 to 98, wherein the at least one additional biomarker is selected from the group comprising free lyso-sphingomyelin and compound 509, and wherein the at least one additional biomarker is different from the bio marker.

Embodiment 100

The method according to any one of embodiments 95 to 99, wherein the biomarker is compound 509 and wherein the at least one additional biomarker is free lyso-sphingomyelin.

Embodiment 101

The method according to any one of embodiments 95 to 100, wherein the subject has been previously treated for Niemann-Pick disease or diagnosed for Niemann-Pick disease.

Embodiment 102

The method according to any one of embodiments 95 to 100, wherein the subject has not been previously treated for Niemann-Pick disease or wherein the subject has not been previously diagnosed for Niemann-Pick disease.

Embodiment 103

The method according to any one of embodiments 95 to 102, wherein the method comprises
  a step d), wherein the step d) comprises applying, maintaining, reducing, elevating or not applying at least one treatment applied to the subject based on the decrease in the level of the biomarker and/or the at least one additional biomarker as determined in step b) and/or the ratio of the level of the biomarker to the level of the at least one additional biomarker as determined in step c).

Embodiment 104

The method according to any one of embodiments 95 to 102, wherein the method comprises
  a step e), wherein the step e) comprises detecting the biomarker and/or the at least one additional biomarker in the sample from the subject, wherein the sample has been taken prior to the beginning of the treatment after applying, maintaining, reducing, elevating or not applying at least one treatment in step d) and, optionally determining a level of a biomarker and/or of a at least one additional biomarker present in a sample from the subject, and optionally determining the ratio of the level of the biomarker to the level of the at least one additional biomarker.

Embodiment 105

The method according to any one of embodiments 95 to 104, wherein the treatment is selected from the group comprising enzyme replacement therapy, substrate reduction therapy, chaperone therapy, gene therapy, stem cell transplantation of DNA/RNA skipping.

Embodiment 106

The method according to any one of embodiments 95 to 105, wherein the method comprises
  a step f), wherein the step f) comprises determining whether the level of the biomarker determined in step b) is lower than the level of the biomarker determined in step e); and/or
  determining whether the level of the at least one additional biomarker determined in step b) is lower than the level of the at least one additional biomarker determined in step e); and/or determining whether the ratio of the level of the biomarker to the level of the at least one additional biomarker as determined in step c) is lower than the ratio of the level of the biomarker to the level of the at least one additional biomarker as determined in step e).

Embodiment 107

The method according to embodiment 106, wherein the method comprises
  a step g). wherein step g) comprises applying, maintaining, reducing, elevating or not applying at least one treatment applied to the subject based on step f).

Embodiment 108

The method according to any one of embodiments 95 to 107, wherein the biomarker and/or the at least one additional biomarker is detected by means of immunoassay, mass spectrometric analysis, biochip array, functional nucleic acids and/or a fluorescent derivative of the biomarker.

Embodiment 109

The method according to embodiment 108, wherein the biomarker and/or the at least one additional biomarker is detected by means of mass spectrometric analysis.

Embodiment 110

The method according to embodiment 109, wherein mass spectrometric analysis is selected from the group consisting of SELDI, MALDI, MALDI-Q TOF, MS/MS, TOF-TOF and ESI-O-TOF.

Embodiment 111

The method according to embodiment 110, wherein the mass spectrometric analysis comprises or uses MS/MS.

Embodiment 112

The method according to any one of embodiments 95 to 111, wherein the method comprises protein precipitation and/or HPLC.

Embodiment 113

The method according to any one of embodiments 96 to 112, wherein the method comprises protein precipitation, HPLC and MS/MS.

Embodiment 114

The method according to any one of embodiments 95 to 113, wherein the subject is a human.

Embodiment 115

The method according to any one of embodiments 95 to 114, wherein Niemann-Pick disease is selected from the group comprising Niemann-Pick disease type A and B, Niemann-Pick disease type C, and Niemann-Pick disease type C carrier.

Embodiment 116

The method according to any one of embodiments 95 to 115, wherein the step of detecting the biomarker in the sample from the subject comprises precipitating protein from the sample from the subject, wherein precipitating protein from the sample provides a supernatant of the sample; subjecting a volume of the supernatant to HPLC and MS/MS and determining the level of the biomarker and/or the at least one additional biomarker that is/are present in the sample from the subject.

Embodiment 117

The method according to any one of embodiments 115 to 116, wherein Niemann-Pick disease type C is selected from the group comprising Niemann-Pick disease type C1, Niemann-Pick disease type C2 and Niemann-Pick disease type D.

Embodiment 118

A method of determining the effectiveness of a compound for the treatment of Niemann-Pick disease, wherein the method comprises the following steps:
a) determining a level of a biomarker in a sample form a subject having Niemann-Pick disease;
b) administering to said subject said compound;
c) determining again the level of the biomarker in a sample from the subject after the compound has been administered to the subject; and
d) determining whether the level of the biomarker determined in step c) is lower than the level of the biomarker determined in step a);
wherein if a level of the biomarker determined in step c) is lower than the level of the biomarker determined in step a) this indicates the effectiveness of said compound.

Embodiment 119

The method according to embodiment 118, wherein
step a) and c) each additionally comprise
determining a level of at least one additional biomarker present in the sample, and wherein
step d) additionally comprises
determining whether the level of the at least one additional biomarker determined in step c) is lower than the level of the at least one additional biomarker determined in step a), and wherein
a level of the at least one biomarker determined in step c) which is lower than the level of the at least one biomarker determined in step a) indicates the effectiveness of said compound.

Embodiment 120

The method according to embodiment 119, wherein
step a) additionally comprises determining the ratio of the level of the biomarker to the level of the at least one additional bio marker;
step c) additionally comprises determining the ratio of the level of the biomarker to the level of the at least one additional biomarker and wherein
step d) comprises
determining whether the ratio of the level of the biomarker to the level of the at least one additional biomarker determined in step c), is lower than the ratio of the level of the biomarker to the level of the at least one additional biomarker determined in step a), and wherein
a ratio of the level of the biomarker to the level of the at least one additional biomarker determined in step c) which is lower than the ratio of the level of the biomarker to the level of the at least one additional biomarker determined in step a) indicates the effectiveness of said compound.

Embodiment 121

The method according to any one of embodiments 118 to 120, wherein any/the biomarker is selected from the group comprising free lyso-sphingomyelin and compound 509, and wherein the biomarker is different from the at least one additional biomarker.

Embodiment 122

The method according to embodiment 121, wherein the method comprises determining a level of the biomarker in a control sample.

Embodiment 123

The method according to any one of embodiments 118 to 121, wherein Niemann-Pick disease is selected from the group comprising Niemann-Pick type A or B, Niemann-Pick type C, and Niemann-Pick type C carrier.

Embodiment 124

The method according to embodiment 123, wherein Niemann-Pick disease type C is selected from the group comprising Niemann-Pick disease type C1, Niemann-Pick disease type C2 and Niemann-Pick disease type D.

Embodiment 125

Use of mass spectrometric analysis for the detection of a biomarker, wherein the biomarker is selected from the group comprising free lyso-sphingomyelin and compound 509.

Embodiment 126

Use according to embodiment 125, wherein the detection comprises the use of HPLC.

Embodiment 127

Use according to any one of embodiments 125 to 126, wherein the mass spectrometric analysis comprises or uses MS/MS.

Embodiment 128

Use of a biomarker for the diagnosis of Niemann-Pick disease, preferably in a method according to any one of embodiments 1 to 127, wherein the biomarker is selected from the group comprising free lyso-sphingomyelin and compound 509.

Embodiment 129

Use of a biomarker for the diagnosis of Niemann-Pick disease, preferably in a method according to any one of embodiments 1 to 124, wherein the biomarker is free lyso-sphingomyelin.

Embodiment 130

Use of a biomarker for the diagnosis of Niemann-Pick disease, preferably in a method according to any one of embodiments 1 to 124, wherein the biomarker is compound 509.

Embodiment 131

Use according to any one of embodiments 125 to 130, wherein Niemann-Pick disease is selected from the group comprising Niemann-Pick type A or B, Niemann-Pick type C, and Niemann-Pick type C carrier.

Embodiment 132

Use according to embodiment 130, wherein Niemann-Pick disease type C is selected from the group comprising Niemann-Pick disease type C1, Niemann-Pick disease type C2 and Niemann-Pick disease type D.

Embodiment 133

Use of a ratio of a level of a biomarker present in a sample from the subject to a level of an at least one additional biomarker present in a sample from the subject for use in a method of diagnosis of Niemann-Pick disease, preferably in a method according to any one of embodiments 1 to 124, wherein the biomarker is selected from the group comprising free lyso-sphingomyelin and compound 509.

Embodiment 134

A kit for determining the presence of a biomarker in a sample from a subject, wherein the kit comprises
a) an interaction partner of the biomarker;
b) optionally a solid support comprising at least one capture reagent attached thereto, wherein the capture reagent binds the biomarker; and
c) instructions for using the solid support to detect the biomarker,
wherein the biomarker is selected from the group comprising free lyso-sphingomyelin and compound 509.

Embodiment 135

The kit according to embodiment 132, wherein the kit is for
a) use in a method for diagnosing Niemann-Pick disease;
b) use in a method for determining the course of Niemann-Pick disease in a subject; and/or
c) use in a method for determining the effectiveness of at least one treatment applied to a subject,
wherein preferably the method of a), b) and/or c) is a method according to any one of embodiments 1 to 124.

Embodiment 136

The kit according to any one of embodiments 134 to 135, wherein Niemann-Pick disease is selected from the group comprising Niemann-Pick type A or B, Niemann-Pick type C, and Niemann-Pick type C carrier.

Embodiment 137

The kit according to embodiment 136, wherein Niemann-Pick disease type C is selected from the group comprising Niemann-Pick disease type C1, Niemann-Pick disease type C2 and Niemann-Pick disease type D.

Embodiment 138

The method according to any one of embodiments 1 to 124, preferably embodiments 1 to 64, wherein the biomarker is compound 509,
wherein if the level of the biomarker in the sample from the subject is higher than 0.031 ng/ml this is indicative that the subject is suffering from Niemann-Pick disease;
wherein Niemann-Pick disease is selected from the group consisting of Niemann-Pick disease type A and/or B, Niemann-Pick disease type C and Niemann-Pick disease type C carrier.

Embodiment 139

The method according to any one of embodiments 1 to 124, preferably embodiment 138, wherein the biomarker is compound 509,
wherein if the level of the biomarker in the sample from the subject is higher than 0.031 ng/ml and is lower than or as high as 1.7 ng/ml this is indicative that the subject is suffering from Niemann-Pick disease
wherein Niemann-Pick disease is selected from the group consisting of Niemann-Pick disease type C carrier.

Embodiment 140

The method according to any one of embodiments 1 to 124, preferably any one of embodiments 138 and 139, wherein the biomarker is compound 509,
wherein if the level of the biomarker in the sample from the subject is higher than 1.7 ng/ml this is indicative that the subject is suffering from Niemann-Pick disease;
wherein Niemann-Pick disease is selected from the group consisting of Niemann-Pick disease type A and/or B and Niemann-Pick disease type C.

Embodiment 141

The method according to any one of embodiments 1 to 124, preferably any one of embodiments 138 to 140, wherein the biomarker is compound 509,
wherein if the level of the biomarker in the sample from the subject is higher than 1.7 ng/ml and is lower than or as high as 5.0 ng/ml this is indicative that the subject is suffering from Niemann-Pick disease
wherein Niemann-Pick disease is selected from the group consisting of Niemann-Pick disease type C.

Embodiment 142

The method according to any one of embodiments 1 to 124, preferably any one of embodiments 138 to 141, wherein the biomarker is compound 509, wherein if the level of the biomarker in the sample from the subject is higher than 5.0 ng/ml this is indicative that the subject is suffering from Niemann-Pick disease;
wherein Niemann-Pick disease is selected from the group consisting of Niemann-Pick disease type A and/or B.

Embodiment 143

The method according to any one of embodiments 1 to 124, preferably any one of embodiments 138 to 142, wherein the biomarker is free lyso-sphingomyelin,
wherein if the level of the biomarker in the sample from the subject is higher than 6.5 ng/ml this is indicative that the subject is suffering from Niemann-Pick disease;
wherein Niemann-Pick disease is selected from the group consisting of Niemann-Pick disease type A and/or B, Niemann-Pick disease type C and Niemann-Pick disease type C carrier.

Embodiment 144

The method according to any one of embodiments 1 to 124, preferably any one of embodiments 138 to 143, wherein the biomarker is free lyso-sphingomyelin,
wherein if the level of the biomarker in the sample from the subject is higher than 6.5 ng/ml and is lower than or as high as 9.23 ng/ml this is indicative that the subject is suffering from Niemann-Pick disease
wherein Niemann-Pick disease is selected from the group consisting of Niemann-Pick disease type C carrier.

Embodiment 145

The method according to any one of embodiments 1 to 124, preferably any one of embodiments 138 to 144, wherein the biomarker is free lyso-sphingomyelin;
wherein if the level of the biomarker in the sample from the subject is higher than 9.23 ng/ml this is indicative that the subject is suffering from Niemann-Pick disease;
wherein Niemann-Pick disease is selected from the group consisting of Niemann-Pick disease type A and/or B and Niemann-Pick disease type C.

Embodiment 146

The method according to any one of embodiments 1 to 124, preferably any one of embodiments 138 to 145, wherein the biomarker is free lyso-sphingomyelin,
wherein if the level of the biomarker in the sample from the subject is higher than 9.23 ng/ml and is lower than or as high as 59 ng/ml this is indicative that the subject is suffering from Niemann-Pick disease
wherein Niemann-Pick disease is selected from the group consisting of Niemann-Pick disease type C.

Embodiment 147

The method according to any one of embodiments 1 to 124, preferably any one of embodiments 138 to 146, wherein the biomarker is free lyso-sphingomyelin,
wherein if the level of the biomarker in the sample from the subject is higher than 59 ng/ml this is indicative that the subject is suffering from Niemann-Pick disease;
wherein Niemann-Pick disease is selected from the group consisting of Niemann-Pick disease type A and/or B.

Embodiment 148

The method according to any one of embodiments 1 to 124, preferably any one of embodiments 138 to 147,
wherein if the ratio of the level of compound 509 in the sample from the subject to the level of free lyso-sphingomyelin is higher than 0.087 this is indicative that the subject is suffering from Niemann-Pick disease;
wherein Niemann-Pick disease is selected from the group consisting of Niemann-Pick disease type C.

Embodiment 149

The method according to any one of embodiments 1 to 124, preferably any one of embodiments 138 to 148,
wherein if the ratio of the level of compound 509 in the sample from the subject to the level of free lyso-sphingomyelin is higher than 0.045 this is indicative that the subject is suffering from Niemann-Pick disease;
wherein Niemann-Pick disease is selected from the group consisting of Niemann-Pick disease type A and/or B and Niemann-Pick disease type C.

Embodiment 150

The method according to any one of embodiments 1 to 124, preferably any one of embodiments 138 to 149,
wherein if the ratio of the level of compound 509 in the sample from the subject to the level of free lyso-sphingomyelin is higher than 0.045 and is lower than or as high as 0.087 this is indicative that the subject is suffering from Niemann-Pick disease
wherein Niemann-Pick disease is selected from the group consisting of Niemann-Pick disease type A and/or B.

The present inventors have surprisingly found that compound 465, also referred to herein preferably as free lyso-sphingomyelin, constitutes a biomarker which allows for a method for diagnosing Niemann-Pick disease in a subject, more specifically diagnosing Niemann-Pick disease in a subject with high specificity and sensitivity using said free lyso-sphingomyelin as the biomarker.

The present inventors have also surprisingly found that compound 509 constitutes a biomarker which allows for a method for diagnosing Niemann-Pick disease in a subject, more specifically diagnosing Niemann-Pick disease in a subject with high specificity and sensitivity using said compound 509 as the biomarker.

Furthermore, the present inventors have also surprisingly found that the ratio of the level of compound 509 in a sample from a subject to the level of compound 465 in a, preferably the sample from the subject both preferably determined by the methods of the present invention, are suitable for the diagnosis of Niemann-Pick disease type C in a subject, more specifically diagnosing Niemann-Pick disease type C in a subject with high specificity and sensitivity.

In other words compound 465 and compound 509, respectively, constitute biomarkers which allow for a method for the differential diagnosis of a first group of Niemann-Pick disease consisting of Niemann-Pick disease type A and B, a second group of Niemann-Pick disease consisting of Niemann-Pick disease type C and a third group of Niemann-Pick disease consisting of Niemann-Pick disease type C carrier. In accordance therewith it is possible to discriminate a subject belonging to or assumed to belong to the first group of Niemann-Pick disease from a subject belonging to or assumed to belong to the second group of Niemann-Pick disease and/or the third group of Niemann-Pick disease. In accordance therewith it is also possible to discriminate a subject belonging to or assumed to belong to the second group of Niemann-Pick disease from a subject belonging to or assumed to belong to the first group of Niemann-Pick disease and/or the third group of Niemann-Pick disease. In accordance therewith it is also possible to discriminate a subject belonging to or assumed to belong to the third group of Niemann-Pick disease from a subject belonging to or assumed to belong to the first group of Niemann-Pick disease and/or the second group of Niemann-Pick disease.

The ratio of the level of compound 509 in a sample from a subject to the level of compound 465 in a or in the sample from the subject allows discriminating Niemann-Pick disease type C from Niemann-Pick disease type A and B. Accordingly, it is possible to discriminate a subject suffering from Niemann-Pick disease type C from a subject suffering from either Niemann-Pick disease type A or B. It is also within the present invention that the ratio of the level of compound 509 in a sample from a subject to the level of compound 465 in a or in the sample from the subject allows to determine whether or not a subject is suffering from or is at risk of suffering from Niemann-Pick disease type C.

The present inventors have also surprisingly found that free lyso-sphingomyelin, which can be detected by the methods of the present invention, is circulating in the blood of a subject in a concentration of approximately 1/1000 of total sphingomyelin. Moreover, the present inventors have surprisingly found that, unlike total sphingomyelin, free lyso-sphingomyelin which is present in the blood of a subject is useful in a method for diagnosing Niemann-Pick disease in a subject comprising a step of detecting a biomarker in a sample from the subject, wherein the biomarker is free lyso-sphingomyelin. The present inventors have also surprisingly found that the level of free lyso-sphingomyelin determined in the sample from a subject by the methods of the present invention allows for diagnosing Niemann-Pick disease with high sensitivity and high specificity.

In so far the present invention turns away from the teaching of the prior art in that the method of the present invention comprises determining the level of a lyso-compound and using said lyso-compound as a biomarker for diagnosis of a sphingolipidoses. More specifically, the present inventors have surprisingly found that determining the level of free lyso-sphingomyelin in a sample from a subject allows for diagnosing Niemann-Pick disease with high sensitivity and high specificity.

It is also the merit of the present inventors of having recognized that a fraction of total sphingomyelin which is accumulated in Niemann-Pick disease, is present as a molecule in a free lyso form thereof, i.e. free lyso-sphingomyelin, and is circulating in the blood of a subject in said free lyso form besides sphingomyelin.

Furthermore, the present inventors have also surprisingly found that compound 509, which can be detected by the methods of the present invention, is circulating in the blood of a subject. Moreover, the present inventors have surprisingly found that compound 509 which is present in the blood of a subject is useful in a method for diagnosing Niemann-Pick disease in a subject comprising a step of detecting a biomarker in a sample from the subject, wherein the biomarker is compound 509. The present inventors have also surprisingly found that the level of compound 509 determined in the sample from a subject by the methods of the present invention allows for diagnosing Niemann-Pick disease with high sensitivity and high specificity.

In connection with the instant invention it is referred to the concentration or level of compound 509. Such concentration or level of compound 509 is preferably determined as follows. In the analytical set-up as described in the example part in more detail an internal standard is added to the sample to be analyzed. In the course of such analysis a chromatogram is obtained indicating as individual peaks the various compounds detected in the sample. The various compounds include, among others, compound 509 and the internal standard. In order to determine from such chromatogram and the peaks indicated therein the concentration or level of compound 509 the peak area of the peak corresponding to compound 509 and the peak area of the peak corresponding to the internal standard is determined. The ratio of the peak area of the peak corresponding to compound 509 and the peak area of the peak corresponding to the internal standard is subsequently determined and normalized to the concentration of the internal standard added to the sample to be analyzed. The thus obtained concentration of compound 509 is also referred to herein as the normalized concentration of compound 509.

In those embodiments of the methods of the present invention where the concentration or level of compound 509 is used, either as such or when calculating a ratio involving said concentration or level of compound 509 such as the ratio of the concentration of compound 509 in the sample from the subject to the concentration of free lyso-sphingomyelin in the sample from the subject, the concentration of compound 509 is preferably the normalized concentration of compound 509.

The term "lysosomal storage disorder", also referred to herein as "lysosomal storage disease" or "LSD", as used herein, preferably refers to genetic diseases and metabolic disorders that result from defects in lysosomal function. Lysosomal storage disorders are caused by lysosomal dysfunction usually as a consequence of deficiency of a single enzyme required for the metabolism of lipids, glycoproteins or so-called mucopolysaccharides. Like other genetic diseases, individuals inherit lysosomal storage diseases from their parents. Although each disorder results from different gene mutations that translate into a deficiency in enzyme activity, they all share a common biochemical characteristic—all lysosomal disorders originate from an abnormal accumulation of substances inside the lysosome.

Niemann-Pick disease, also referred to herein preferably as NP, are autosomal recessively inherited genetic diseases which are classified in a subgroup of LSD called sphingolipidoses or lipid storage disorders in which harmful quantities of fatty substances, or lipids, accumulate in the spleen, liver, lungs, bone marrow, and brain. Depending on the mutation of the affected protein Niemann-Pick disease is usually divided into four subgroups, namely Niemann-Pick disease type A, B, C and D, also referred to herein preferably as NPA in case of Niemann-Pick disease type A, NPB in case of Niemann-Pick disease type B, NPC in case of Niemann-Pick disease type C and NPD NPD in case of Niemann-Pick disease type D, respectively. Thus Niemann-Pick disease as used herein preferably comprises Niemann-Pick disease type A, Niemann-Pick disease type B, Niemann-Pick disease type C and Niemann-Pick disease type D.

That Niemann-Pick disease is inherited in an autosomal recessive pattern means that both copies, or alleles, of the gene must be mutated or altered in such a way that function is impaired, in contrast to a polymorphism, in which the nucleotide sequence is altered but causes no functional disruption, for a person to be affected by the disorder. Most often, the parents of a child with an autosomal recessive disorder are not affected but are carriers of one copy of the altered gene. Such carrier is referred to herein as Niemann- Pick disease carrier, e.g. Niemann-Pick disease type C carrier. If both parents are carriers, there is a 25% chance with each pregnancy for an affected child. Genetic counseling and genetic testing is recommended for families who may be carriers of Niemann-Pick.

NPA has an extremely poor prognosis with most cases being fatal by the age of 18 months. NPB and NPC normally possess a better prognosis, with many patients with these disorders living into their teens or adulthood.

Niemann-Pick disease Type C is biochemically, genetically and clinically distinct from Niemann Pick disease types A or B.

Mutations in the SMPD1 gene cause complete or partial deficiency of an enzyme called acid sphingomyelinase resulting in accumulation of sphingomyelin and leading to NPA and NPB, respectively.

Approximately 95% of Niemann-Pick disease Type C cases, referred to herein preferably as type C1 or NPC1, are caused by genetic mutations in the NPC1 gene, whereas 5%, referred to herein preferably as type C2 or NPC2, are caused by mutations in the NPC2 gene (Mellon S H et al., March 2008. Brain research reviews 57 (2): 410-20).

In NPC the protein product of the major mutated gene NPC1 is not an enzyme but appears to function as a trans-membrane transporter protein in the endosomal-lysosomal system, which moves large water-insoluble molecules through the cell. The protein coded by the NPC2 gene is a soluble non-enzymatic protein which seems to act in cooperation with the NPC1 protein in transporting molecules in the cell. The disruption of this transport system results in the accumulation of cholesterol and glycolipids in lysosomes.

The clinical manifestations of NPC1 and NPC2 are similar because the respective genes are both involved in egress of lipids, particularly cholesterol, from late endosomes or lysosomes. The NPC1 gene is located on chromosome 18 (18q11-q12) (Zhang J R et al., June 2008, The Journal of clinical investigation 118 (6): 2281-90).

NPD was originally separated from NPC to delineate a group of patients with otherwise identical disorders who shared a common Nova Scotian ancestry. Patients in this group are now known to share a specific mutation in the NPC1 gene. In an embodiment of Niemann-Pick disease type C, NPC comprises NPD. In a further embodiment of Niemann-Pick disease type C, NPC comprises NPC1 and NPC2.

Individuals affected by NPC may show symptoms comprising splenomegaly, hepatomegaly or hepatosplenomegaly, but this finding may be absent in later onset cases. Prolonged jaundice or elevated bilirubin can present at birth. In some cases, however, enlargement of the spleen and/or liver does not occur for months or years—or not at all. Enlargement of the spleen and/or liver frequently becomes less apparent with time, in contrast to the progression of other LSD such as NPA and NPB or Gaucher's disease. Organ enlargement does not usually cause major complications.

Progressive neurological disease is the hallmark of NPC and is responsible for disability and premature death in all cases beyond early childhood. Children with NPC may initially present with delays in reaching normal developmental milestones skills before manifesting cognitive decline, i.e. dementia for example.

Neurological signs and symptoms include cerebellar ataxia, dysarthria, dysphagia, tremor, both partial and generalized epilepsy, vertical supranuclear palsy comprising upgaze palsy, downgaze palsy, saccadic palsy or paralysis, sleep inversion, gelastic cataplexy, dystonia, most commonly begins with in turning of one foot when walking (action dystonia) and may spread to become generalized, spasticity, hypotonia, ptosis, microcephaly, psychosis, progressive dementia, progressive hearing loss, bipolar disorder, major and psychotic depression that can include hallucinations, delusions, mutism, or stupor. In the terminal stages of NPC, the patient is bedridden, with complete ophthalmoplegia, loss of volitional movement and has severe dementia.

The accumulated substances, cholesterol and glycolipids, have varied roles in the cell. Cholesterol is a major component of cell plasma membranes, which define the cell as a whole and its organelles. It is also the basic building block of steroid hormones, including neurosteroids. In NPC, large amounts of free or unesterified cholesterol accumulates in lysosomes, and leads to relative deficiency of this molecule in multiple membranes and for steroid synthesis. The accumulation of glycosphingolipids in the nervous system has been linked to structural changes, namely ectopic dendritogenesis and meganeurite formation.

NPC is diagnosed by assaying cultured fibroblasts for cholesterol esterification and staining for unesterified cholesterol with filipin. The fibroblasts are grown from a small skin biopsy taken from a patient with suspected NPC. The diagnosis can be confirmed by identifying mutations in the NPC1 or NPC2 genes.

The prognosis for patients having NPC usually relates to the age of onset. Children with antenatal or infantile onset usually succumb in the first few months or years of life, whereas adolescent and adult onset forms of NPC have a more insidious onset and slower progression, and affected individuals may survive to the seventh decade. Adult cases of NPC are being recognized with increasing frequency. It is suspected that many patients affected by NPC are undiagnosed, owing to lack of awareness of the disease and the absence of readily available screening or diagnostic tests. For the same reasons the diagnosis is often delayed by many years.

Currently there are no causative cures for NP and treatment is mostly symptomatic and limited with care being mostly supportive. Organ transplantation has been attempted with limited success. Bone marrow transplant has been attempted for NPB. Future prospects include enzyme replacement therapy, also referred to herein preferably as ERT, and gene therapy. Several other treatment strategies are under investigation in cell culture and animal models of NPC. These include cyclodextrin, cholesterol mobilization, neurosteroid and Curcumin as an anti-inflammatory and calcium modulatory agent (Loyd-Evans E et al., October 2008, Nature medicine 14 (11): 1247-55).

The drug Zavesca comprising Miglustat as an active ingredient has been approved at least in the European Union for the treatment of progressive neurological manifestations in adult patients and pediatric patients with Niemann-Pick disease type C disease. Miglustat is a glucosylceramide synthase inhibitor, which inhibits the synthesis of glycosphingolipids in cells. It has been shown to delay the onset of disease in the NPC mouse, and published data from a multi-center clinical trial of Miglustat in the United States and England and from case reports suggests that it may ameliorate the course of human NPC.

Sphingomyelin is a sphingolipid found in cellular membranes of animal cells, especially in the membranous myelin sheath that surrounds some nerve cell axons.

In humans, sphingomyelin is believed to be the only cell membrane phospholipid not derived from glycerol.

Like all sphingolipids, sphingomyelin consists of a ceramide core, i.e. sphingosine bound to a fatty acid via an amide linkage. In addition, it contains one polar head group, which is either phosphocholine, phosphochorylcholine or phosphoethanolamine. A typical sphingomyelin has the formula:

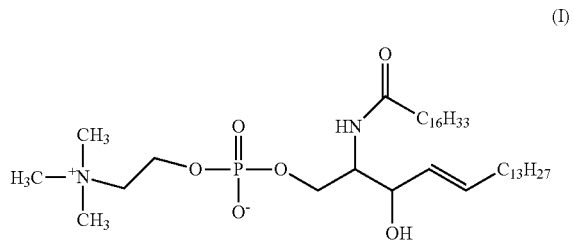

(I)

In NPA and NPB the enzyme deficiency results in a block of lipid degradation, resulting in the accumulation of sphingomyelin within lysosomes in the macrophage-monocyte phagocyte lineage. Affected cells become enlarged, sometimes up to 90 microns in diameter, secondary to the distention of lysosomes with sphingomyelin and cholesterol.

It will be understood by a person skilled in the art that the term "lyso-sphingomyelin" as used herein, preferably in connection with the various methods of the invention, preferably means that the molecule is present in its free amino form. More precisely, lyso-sphingomyelin as used herein, preferably differs from sphingomyelin in that no fatty acid moiety is linked to the—primary—amino group of the sphingosine moiety of the molecule. Furthermore, lyso-sphingomyelin is also referred to herein as compound 465, Sphingosylphosphorylcholine or Sphingosine phosphorylcholine. A typical lyso-sphingomyelin has the formula:

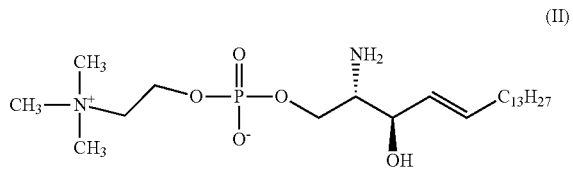

(II)

It will be understood by a person skilled in the art that the term "free lyso-sphingomyelin" as used herein preferably refers to lyso-sphingomyelin which is as such present in a sample from a or the subject, such as blood, and, preferably, is not the result of a manipulation of the sample of said subject. Such manipulation of a sample can be the one described by Groener et al. (Groener et al., Biochimica et Biophysica Acta 1781(2908)72-78, 2007). In accordance therewith, free lyso-sphingomyelin which is present as such in the blood of a subject from whom the sample is taken, is more particularly not a lyso-sphingomyelin which is generated by chemical, biochemical or physical treatment of the sample contained in the blood and sample, respectively, preferably outside of the body of the patient. It will be also understood by a person skilled in the art that free lyso-sphingomyelin as used herein, preferably is present in addition to sphingomyelin and is a compound produced by the subject's metabolic activities. Accordingly, sphingomyelin, which is the molecule that is accumulated in connection with Niemann-Pick disease, such as Niemann-Pick disease type A and type B, is present in the sample from the subject and has compared to the molecule in a free lyso form, i.e. free-lyso-sphingomyelin, present in the blood of the subject at least one fatty acid moiety linked to the—primary—amino group of the sphingosine moiety of lyso-sphingomyelin.

In an embodiment of the biomarker according to the present invention the biomarker is detected by means of immunoassay, mass spectrometric analysis, biochip array, functional nucleic acids and/or a fluorescent derivative of the biomarker. In connection therewith it is important to note that such detection allows for the selective detection of the biomarker as present in the blood of a subject as such and particularly is not the result of a manipulation of the sample of said subject resulting in a change of the concentration of the biomarker, such as the derivatization of Gb1 into lyso-Gb1 according to the method of the prior art as described above. Such manipulation may result in the inability to distinguish the biomarker of the present invention, such as free-lyso-shpingomyelin, and thus the biomarker of the present invention cannot be detected as such and the level of said biomarker cannot be determined as such, respectively, without detecting the manipulated further substance, e.g. Gb1 derivatized into lyso-Gb1 according to the method of the prior art. In the light thereof it will be immediately understood that the biomarker present in the blood of the subject such as free-lysosphingomyelin present as such in the blood of the subject, is also present in the sample of the subject as such and may, nevertheless, be selectively labeled with and/or linked to a means such as a fluorescent dye or a nucleic acid molecule specifically binding the biomarker. Such selective labeling or linking allows detecting and/or determining the level of the labeled or linked biomarker, without labeling of, linking to or converting a further substance, such as the converted lyso-Gb1 of the prior art, which cannot be distinguished from the biomarker, more precisely the labeled or linked biomarker. In connection therewith, e.g. a fluorescent derivative of the biomarker of the present invention concerns a biomarker which is labeled with and/or bound to a fluorescence dye or molecule, i.e. resulting in a fluorescent derivative of the biomarker, which allows for detecting the fluorescent derivative and/or determining the level of the fluorescent derivative of the biomarker of the invention.

The substance herein referred to as compound 509, which can be detected by the methods of the present invention and which is useful in the method according to the present invention as a biomarker is a substance having a molecular weight of 508, detected as MRM transition in positive mode 509 m/z to 184 m/z in a sample of plasma from a subject according to the method of the present invention, more particularly in Example 1 and Example 2 as described herein.

The term "sample" as used herein means preferably a limited quantity of a subject's material, wherein said subject's material is part of or has been taken from a subject and/or a subject's body. Preferably, said material is selected from the group comprising body fluids such as blood, a blood product, urine, saliva, cerebrospinal fluid and lymph, as well as stool or any kind of tissue and or cell material being part of a subject and/or a subject's body. It will be acknowledged by a person skilled in the art, that the presence of and/or a level of a biomarker of the invention in said sample is intended to be similar to and represent the presence and/or the level of the biomarker in a larger amount of that subject's material. More precisely and as an illustrative, non-limiting example, a level of a biomarker of the invention determined in a sample of, e.g., some ml of blood from a subject also represents a level of said biomarker in the blood of the subject's body. Furthermore, in an embodiment of the method of the invention for diagnosing Niemann-Pick disease in a subject, a sample from the subject comprises said subject's material in a form, for example processed, fixed and/or preserved such that said sample is suitable for use in the method of the invention, whereby such processing, fixing and/or preserving preferably does not generate lyso-sphingomyelin and/or compound 509 which was not as such present in the blood of the patient. The subject's material in the sample may thus be diluted, for example with a solvent suitable for the method of the invention such as methanol and/or water, may be dried, for example on a filter card, may be resolved after having been dried such, for example with a solvent suitable for the method of the invention such as methanol and/or water, or a substance may be added, wherein said substance prevents blood from coagulation such as for example EDTA or heparin. It will be further understood by a person skilled in the art that the method of the invention comprises that said subject's material is separated into single components of said subject's material and/or single components of said subject's material are extracted from said subject's material, for example blood is separated into plasma or serum and cellular blood components or protein is precipitated from the sample. Accordingly, in an embodiment of the method according to the present invention wherein the method comprises protein precipitation and/or HPLC, precipitation of protein preferably results in a) a precipitation of cellular blood components and/or protein, more preferably forming a pellet after a step of centrifugation, and b) the biomarker being preferably not precipitated and being present in the supernatant after a step of centrifugation. A person skilled in the art will immediately understand that in an embodiment of the method according to the present invention wherein the method comprises HPLC a supernatant containing the biomarker(s) of the present invention or a part thereof is subjected to HPLC. In connection therewith it is important to understand that the supernatant or a part thereof which is subjected to HPLC comprises the biomarker to be detected as well as, preferably, an internal standard. In an embodiment of the method of the invention wherein an internal standard is added to the sample, the internal standard may be added to the sample before or after a precipitation step, i.e. the internal standard may be added into the sample immediately after the sample is taken from the subject, or may be added to the supernatant which is subjected to HPLC, as well as in between these time points. A person skilled in the art will know, how and when an internal standard is preferably added to the sample in order to achieve an accurate detection and determination of a level of the biomarker.

It will be immediately understood that after such processing, fixing and/or preserving the sample is subjected to the methods of the invention for detecting and/or determining the level of a biomarker contained in said sample whereby such processing, fixing and/or preserving preferably does not generate lyso-sphingomyelin and/or compound 509 which was not present in the sample from the patient as such.

In an embodiment of the method of the present invention wherein whole blood is collected on a dry blood filter card preferably approximately 3 µl of full blood are collected on a spot of said dry blood filter card having a diameter of 3 mm. A person skilled in the art will acknowledge that the exact volume thus collected may vary depending on the hematocrit of the specific patient.

The levels of glucosylceramide and its precursor ceramide were used in the prior art to correlate their presence in plasma with the severity of Gaucher's disease type I and the response to the application of therapy (Groener et al., Biochimica et Biophysica Acta 1781(2908)72-78, 2007). Thereby, the level of Gb1 was found to be different although ceramide levels were not significantly different in the plasma of treated and untreated Gaucher's disease type I patients.

In the study reported by Groener et al. (Groener et al., supra) the ratio of Gb1/ceramide was used to discriminate between Gaucher's disease patients and healthy patients. Gb1 and ceramide were measured with high performance liquid chromatography (HPLC) essentially as described in Groener et al. (J. E. M. Groener et al., Clin. Chem. 53 (2007) 742-747). In connection therewith it is important to understand that Gb1 present in the plasma mainly consists of a sugar moiety and a ceramide moiety. The ceramide moiety comprises a sphingosine and a fatty acid moiety. According to the method of the prior art lipids are extracted and ceramide and glucosylceramide are deacetylated by alkaline hydrolysis thus forming the lyso form, i.e. lyso-Gb1 (T. Taketomi et al., J. Biochem. (Tokyo) 120 (1996) 573-579). Subsequently, the thus produced lyso-Gb1 is labeled with a fluorescence dye by derivatization with O-phthaldialdehyde (OPA) at the primary amine group. Afterwards the derivatized sphingoid bases were separated by reverse phase HPLC and detected with a fluorescence detector. Thus said method of the prior art is able to detect total Gb1 consisting of free lyso-Gb1 and Gb1 and is not able to distinguish a level of free lyso-Gb1 from a level of Gb1 in a sample from a subject. The level of said total Gb1 after cleavage of the various fatty acid moieties from the NH2 group of the Gb1 is usually in a range of from 5 to 30 µg per mL plasma or serum. From this it is evident that in the method of Groener et al. (Groener et al., supra) the total-Gb1 which can be prepared and obtained, respectively, from a sample, preferably a blood sample, from a subject is used as a biomarker rather than the free lyso-Gb1 contained in the blood and accordingly also in the sample without performing a cleavage of the fatty acid moiety/moieties, preferably a cleavage performed by an operator handling the sample. Insofar, the present invention is related to the detection of free lyso-sphingomyelin rather than total-sphingomyelin.

Although total Gb1 measured as lyso-Gb1 in said study of the prior art was increased in plasma of said patients, said increase in total Gb1 was not prominent and thus the specificity and the sensitivity of the method were low showing that Gb1 is not suitable as a biomarker for Gaucher's disease.

It is an embodiment of the methods of the present invention comprising detecting and/or determining the level of free lyso-sphingomyelin in a sample from a subject that free lyso-sphingomyelin and/or the level of free lyso-sphingomyelin is determined separate from and/or apart from sphingomyelin or a level of sphingomyelin which may be present in the blood of a subject. In a further embodiment sphingomyelin and/or a level of sphingomyelin is detected/determined in addition to the detection of and/or the determining of a level of free lyso-sphingomyelin.

Importantly, each primary amine circulating in the plasma and being sufficiently lipophilic to be extracted concomitantly with sphingomyelin using an organic solvent according to said method of the art is labeled accordingly and thus is able to disturb the detection of cleaved lyso-sphingomyelin.

In an embodiment of the biomarker according to the present invention what has been outlined above with regard to free lyso-sphingomyelin also applies to any biomarker of the present invention being present as in a free-lyso form.

Insofar, the biomarker of the present invention and uses thereof clearly exceed the performance of methods for diagnosing Niemann-Pick disease, preferably Niemann-Pick disease type A and B, Niemann-Pick disease type C and/or Niemann-Pick disease type C carrier, known the prior art, more specifically, attempts of such methods using biomarkers. It will be immediately understood that a method for diagnosing Niemann-Pick disease analogous to the method applied by Groener et al. for diagnosing Gaucher's disease (Groener et al., supra) is prejudicial compared to the methods of the present invention in that diagnosing of Niemann-Pick disease based on such method of the prior art using total sphingomyelin rather than free lyso-sphingomyelin as the method of the prior art using total Gb1 rather than free lyso-Gb1 is not suitable for reliable clinical application thereof, i.e. the method has no sensitivity and specificity sufficient to diagnose Gaucher's disease by a reliable statistically secured prediction.

In clear contrast thereto the present invention provides methods for the diagnosis of Niemann-Pick disease and biomarkers used in said methods which allow the diagnosis of Niemann-Pick disease with high sensitivity and high specificity. More importantly, the methods of the present invention using the biomarker/biomarkers of the present invention allows for differentially diagnosing Niemann-Pick disease type A and B; and Niemann-Pick disease type C; and Niemann-Pick disease type C carrier in a subject. To the best of their knowledge the present inventors believe that the methods of the present invention allow for the first time to delineate Niemann-Pick disease type C from Niemann-Pick disease type A and B using a biomarker/biomarkers according to the present invention in a rapid, and more importantly, highly sensitive and highly specific assay suitable of clinical application.

The term "Niemann-Pick disease status" as used herein, preferably refers to the status of the disease in the subject. Examples of types of Niemann-Pick disease statuses include, but are not limited to, the subject's risk of suffering or developing Niemann-Pick disease, the stage of the disease in a subject and the effectiveness of treatment of the disease. Other statuses and degrees of each status are known in the art. In an embodiment of the present invention the Niemann-Pick disease status comprises a severe, mild, or healthy Niemann-Pick disease status.

The term "diagnosing" as used herein, preferably means determining the presence or the absence of a disease or disorder in a subject and/or determining whether a subject is at risk for developing a disease, a disorder or symptoms related to a disease or disorder as well as predicting a status of a disease. "Diagnosis" or "diagnosing" as used herein also preferably means that a cause of symptoms of a disease which are present or will be present is identified.

In connection therewith it is important to note that a person skilled in the art, such as a skilled clinician consulted by a subject suffering from symptoms or suspected to be ill, applies the methods of the present invention and thus determines whether a subject is at risk for developing a disease, particularly Niemann-Pick disease and more particularly Niemann-Pick disease type A/B, Niemann-Pick disease type C and/or Niemann-Pick disease type C carrier, whether a subject suffers from such disease or predicts the status of such disease, preferably based on the result obtained by the practicing of the methods of the present invention.

Based on said diagnosis the person skilled in the art will recommend to apply, maintain, reduce, elevate or not apply a therapy or to perform further diagnostic tests.

It is thus an embodiment of the method of the present invention for diagnosing Niemann-Pick disease that the method comprises giving a recommendation whether a therapy should be applied, maintained, reduced, elevated or not applied.

The term "differentially diagnosing" as used herein in connection with the method of the present invention preferably means that the method allows determining the presence or the absence of a disease or disorder in a subject and/or determining whether a subject is at risk for developing a disease, a disorder or symptoms related to a disease or disorder as well as predicting a status of a disease, wherein the disease is each and any of Niemann-Pick disease type A and B; Niemann-Pick disease type C; and Niemann-Pick disease type C carrier.

The term "detecting" in the context of the present invention means methods which include detecting the presence or absence of a substance in a sample and/or qualifying the type of said substance. Detecting can be accomplished by methods known in the art and those further described herein, including, but not limited to, the direct measurement of the affected protein(s) e.g. the sequencing of genes SMPD1, NPC1 and/or NPC2. Any suitable method can be used to detect one or more of the biomarkers described herein. These methods include, without limitation, mass spectrometry (e.g. HPLC-MS/MS), fluorescence (e.g. sandwich immunoassay), HPLC-fluorescence or HPLC-UV preferably after derivatization of free lyso-sphingomyelin and/or compound 509.

A biomarker as used herein, preferably is any biological compound, such as a protein and a fragment thereof, a peptide, a polypeptide, a proteoglycan, a glycoprotein, a lipoprotein, a carbohydrate, a lipid, a nucleic acid, an organic or inorganic chemical, a natural polymer, and a small molecule, which is differentially present in a sample from a subject of one phenotypic status (e.g. having a disease) as compared with another phenotypic status (e.g. not having the disease) and which may be isolated from, or measured in the sample from the subject. Furthermore, the biomarker can be the entire intact molecule, or it can be a portion thereof which is preferably detected by mass spectrometric analysis, an antibody, another protein specifically binding the biomarker, functional nucleic acids specifically binding the biomarker and/or a fluorescent label. A biomarker is furthermore considered to be informative if a measurable aspect of the biomarker is associated with a given status of the patient, such as a particular status of Niemann-Pick disease type C. Such a measurable aspect may include, for example, the presence, absence, or the level of the biomarker in the sample from the subject and/or its presence as part of a profile of biomarkers. A measurable aspect may also be a ratio of two or more measurable aspects of biomarkers, which biomarkers may or may not be of known identity, for example. A profile of biomarkers comprises at least two such measurable aspects, where the measurable aspects can correspond to the same or different classes of biomarkers such as, for example, a nucleic acid and a carbohydrate. A biomarker profile may also comprise at least three, four, five, 10, 20, 30 or more measurable aspects. In one embodiment, a biomarker profile comprises hundreds, or even thousands, of measurable aspects. In another embodiment, the biomarker profile comprises at least one measurable aspect of at least one biomarker and at least one measurable aspect of at least one internal standard.

In an embodiment of the method according to the present invention an internal standard is added to a sample from a subject. It will be acknowledged that by said addition of internal standard, also referred to herein as IS, to the sample, i.e. spiking of the sample, to be subjected to the method according to the present invention, the concentration of IS in the sample is known and, e.g., by determining the area under the peak, i.e. the peak area, of the internal standard in, e.g., an HPLC-mass spectrometric chromatogram the relation between a peak area and a concentration of a substance, e.g. of IS and/or the biomarker of the present invention, e.g. free lyso-sphingomyelin and/or compound 509, can thus be calculated, e.g., by calculating the ratio of the peak area of free lyso-sphingomyelin and/or compound 509 and the peak area of IS. A person skilled in the art will further acknowledge that various molecules may be used as an IS. Nevertheless an IS having a similar chemical structure compared to the molecule such as the biomarker, e.g. free lyso-sphingomyelin and/or compound 509, is preferable. In accordance therewith, the present inventors have in an embodiment chosen lyso-Gb2 which is not present as such in nature. In a preferred embodiment the molecule being the IS can be distinguished from the biomarker or the biomarkers of the present invention, e.g. free lyso-sphingomyelin and/or compound 509, in the method of the present invention. In a further preferred embodiment the IS is selected such that a molecule which is ideally not present or rare in nature. In an embodiment of the present invention where the internal standard is added to a sample from a subject, it is preferred that the IS is added such that it is dissolved in a solvent, e.g. ethanol, prior to said addition to the sample. In a further preferred embodiment that the solvent is selected such that said solvent is capable of causing protein precipitation, preferably is capable of causing the protein precipitation step as subject to the method of the present invention.

In some embodiments of the present invention a protein precipitation and/or protein precipitation step is part of the method of the present invention. It will be understood that precipitation as used herein, preferably means the formation of a solid in a solution, i.e. for example the formation of a protein precipitate in a sample, e.g. serum, from a subject. When precipitation, e.g. protein precipitation, occurs in a sample, the solid formed is called the precipitate, or when compacted by a centrifuge, a pellet. The liquid remaining above the solid is in either case called the supernatant. The present invention contemplates different methods of precipitation and/or separating said supernatant and said precipitate or pellet, comprising, among others, settling or sedimentation and centrifugation. A person skilled in the art will know further methods for protein precipitation and/or for separating a supernatant and a protein precipitate, nevertheless said skilled person will acknowledge that if a method, preferably a method of the invention, is applied were precipitated protein will disable a device such as a column or HPLC-column used in connection with the present invention the precipitated protein is preferably separated from the solvent and/or the sample.

In some embodiments of the present invention a level of a biomarker of the present invention, e.g. free lyso-sphingomyelin and/or compound 509, determined by a method of the present invention in a sample is compared to a level of the same or another biomarker of the present invention determined by a method of the present invention in another sample, e.g. from the same patient, from another patient, from a control and/or from the same or different time points, and/or a cut-off value, and/or a level of a control and/or a level of an IS. In connection therewith "comparing" or "compared to" as used herein, preferably means the mathematical comparison of the two or more values of the levels of the biomarker(s). It will thus be immediately evident whether one of said values is higher, lower or identical if at least two of such values are compared with each other.

In some embodiments of the present invention the method of the present invention comprises a step of determining the ratio of the level of two biomarkers determined by the method of the present invention. In a more preferred embodiment the ratio is determined by dividing the level of a first biomarker, i.e. a biomarker of the present invention, by the level of a second biomarker, i.e. at least one additional biomarker of the present invention, wherein the level of both biomarkers was determined by the present invention. In an even more preferred embodiment the ratio is determined by dividing the level of the biomarker and the level of the at least one additional biomarker, wherein most preferably the biomarker is compound 509 and the at least one additional biomarker is free lyso-sphingomyelin. It is the merit of the present inventors having found that said ratio of the levels of two biomarkers is indicative that the subject is suffering from or is at risk of suffering from Niemann-Pick disease, more particularly for suffering from any one of Niemann-Pick disease type A and B; Niemann-Pick disease type C; and Niemann-Pick disease type C carrier. In a more preferred embodiment the ratio of the level of compound 509 to the level of free lyso-sphingomyelin being higher than the cut-off value is indicative that the subject is suffering from or is at risk of suffering from Niemann-Pick disease type C. It is important to understand in connection therewith that a cut-off value to which said ratio is compared to is the value which allows to diagnose with the highest selectivity and sensitivity.

In an embodiment of the method according to the present invention in which a ratio of two biomarkers determined by the method of the present invention is determined and which is indicative that the subject is suffering from a particular disease, e.g. by comparing said ratio to a cut-off value, it is considered to combine the diagnosis based on said ratio with a diagnosis based on a level of one or more single biomarkers present in the sample which is indicative that the subject is suffering from a particular disease, e.g. by comparing said level(s) to the respective cut-off value(s). In other words, it is considered to first detect a biomarker in a sample from the subject, determine a level said biomarker present in the sample and compare said level of said biomarker to a first cut-off value, wherein said first cut-off value allows for diagnosing a disease, preferably differentially diagnosing said disease; second detect an additional biomarker in a sample from the subject, determine a level of said additional biomarker present in the sample and compare said level of said biomarker to a second cut-off value, wherein said second cut-off value allows for further diagnosing the disease or confirming the result of diagnosing with the biomarker used first, and/or preferably differentially diagnosing said disease; and third determining the ratio of the level of the biomarker to the level of the additional biomarker and compare said ratio to a third cut-off value, wherein said third cut-off value allows for further diagnosing the disease or confirming the result of diagnosing with the biomarker used first and the additional biomarker, and/or preferably differentially diagnosing said disease.

The term "cut-off value" as used herein preferably refers to a level, concentration and/or a titer of a biomarker of the present invention. In some embodiments where a ratio of two levels, concentrations and/or titers of the biomarkers of the present invention is considered said cut-off value is referred to a value of a ratio to which the ratio of two levels, concentrations and/or titers of the biomarkers is compared, and wherein if said ratio of two levels, concentrations and/or titers of the biomarkers of the present invention determined by the methods of the present invention is elevated, increased or higher compared to the cut-off value to which the ratio of two levels, concentrations and/or titers of the biomarkers is compared, this is indicative that the subject is suffering from or is at risk for developing Niemann-Pick disease, and/or preferably Niemann-Pick disease type A and B, Niemann-Pick disease type C, and/or Niemann-Pick disease type C carrier; and/or wherein if said ratio of two levels, concentrations and/or titers of the biomarkers of the present invention is decreased or lower compared to o the cut-off value to which the ratio of two levels, concentrations and/or titers of the biomarkers is compared, this is indicative that the subject is not suffering from or is not at risk for developing Niemann-Pick disease.

In one particular embodiment thereof
using compound 509 as the biomarker allows for
diagnosing NP type A and B using a cut-off value for compound 509 of 5 ng/ml with a sensitivity of 94.4% and a specificity of 96.1%; and/or
diagnosing NP type C using a cut-off value for compound 509 of 1.7 ng/ml with a sensitivity of 97.2% and a specificity of 93.3%; and/or
diagnosing NP type C carrier using a cut-off value for compound 509 of 0.031 ng/ml with a sensitivity of 100% and a specificity of 22.5%;
using free lyso-sphingomyelin as the additional biomarker allows for
diagnosing NP type A and B using a cut-off value for free lyso-sphingomyelin of 59 ng/ml with a sensitivity of 94.4% and a specificity of 99.3%; and/or
diagnosing NP type C using a cut-off value for free lyso-sphingomyelin of 9.23 ng/ml with a sensitivity of 94.4% and a specificity of 81.3%; and/or
diagnosing NP type C carrier using a cut-off value for free lyso-sphingomyelin of 6.5 ng/ml with a sensitivity of 100% and a specificity of 61.2%; and
using the ratio of the level of compound 509 to the level of free lyso-sphingomyelin allows for
diagnosing NP type A and B using a cut-off value for the ratio of the level of compound 509 to the level of free lyso-sphingomyelin of 0.045 with a sensitivity of 94.4% and a specificity of 82.1%; and/or
diagnosing NP type C using a cut-off value for the ratio of the level of compound 509 to the level of free lyso-sphingomyelin of 0.087 with a sensitivity of 94.4% and a specificity of 95.5%.

The term "ratio" as used herein preferably means that between two numbers of the same kind, such as the levels of two biomarkers of the present invention, such as the levels of compound 509 and compound 465, a relationship exists which is usually expressed as "a to b", "a:b" or "the ratio of a to b", for example "the ratio of the levels of compound 509 to compound 465". More preferably "ratio" indicates how many times the first number, i.e. "a" contains the second, i.e. "b", wherein said ratio is not necessarily an integer. In other words if for example "the ratio of the level of compound 509 to compound 465" is concerned the value representing the level of compound 509 is divided by the value representing the level of 465.

In connection therewith it has to be noted that it is the merit of the present inventors having recognized that the relationship of two biomarkers is of diagnostic value, the comparison of which to a respective cut-off value allows for the diagnosis of Niemann-Pick disease, more particularly, Niemann-Pick disease type C. It will be thus immediately understood that said relationship between the levels of two biomarkers according to the present invention may be expressed and/or processed by various mathematical operations and/or various mathematical models may be applied to one level or both levels of the two biomarkers. Accordingly, it is within the present invention that mathematical operations and/or various mathematical models are applied to one or more level(s) of biomarkers determined according to the present invention. As an example the reciprocal value of a ratio of the level of two biomarkers may be used instead of the ratio itself.

In some embodiments of the present invention the level of the biomarker is also determined in a control. As used herein, a control is preferably a sample from a subject wherein the Niemann-Pick disease status of said subject is known. In an embodiment a control is a sample of a healthy patient. In a further embodiment an amount of said biomarker is added to said sample of a healthy patient prior to determining the level of said biomarker in said sample of a healthy patient comprising said added biomarker with a method of the present invention. In a further embodiment the control is a sample from at least one subject having a known Niemann-Pick disease status, such known Niemann-Pick disease status comprising severe, mild, or healthy Niemann-Pick disease status, e.g. a control patient. In a further preferred embodiment the Niemann-Pick disease status also comprises the type of Niemann-Pick disease, more preferably comprising Niemann-Pick disease type A, B, C, and in a still further preferred embodiment also comprises the genetic status with regard to mutations of the genes, affected ins said diseases, comprising SMPD1, NPC1 and NPC2, i.e. comprising the subject having homozygous and/or compound heterozygous mutations, the subject being a carrier of a mutation.

In a further preferred embodiment the control is a sample from a subject not being treated for Niemann-Pick disease. In a still further preferred embodiment the control is a sample from a single subject or a pool of samples from different subjects and/or samples taken from the subject(s) at different time points.

The term "level" or "level of a biomarker" as used herein, preferably means the concentration of a substance and/or titer of a substance, preferably of a biomarker of the invention and more preferably of free lyso-sphingomyelin and/or compound 509, within a sample of a subject. It will be understood by a skilled person that in certain embodiments said sample is not necessarily subjected to a method of the invention as a non-processed sample, the method comprising determining a level of said biomarker, i.e. said sample may be subjected, e.g. to a step of protein precipitation, separation, e.g. centrifugation and/or HPLC and subsequently subjected to a step of determining the level of the biomarker, e.g. using mass spectrometric analysis. It should be further noted that whenever the term "a" level of a biomarker is used in connection with a level of the biomarker of the invention which is to be determined according to the present invention, "the" level of the biomarker of the present invention which is to be determined by the methods of to the present invention and which is contained in the sample subjected to the method(s) of the invention is meant.

The level of a biomarker is different between different statuses of Niemann-Pick disease, if the mean or median level of the biomarker in the different groups is calculated to be statistically significant. Common tests for statistical significance include, among others, t-test, ANOVA, Wilcoxon, Mann-Whitney, odds ratio and Kruskal-Wallis. Biomarkers, alone or in combination, provide measures of relative risk that a subject belongs to one phenotypic status or another.

Therefore, biomarkers of the present invention are useful in an embodiment of the present invention as markers for disease, therapeutic effectiveness of a drug or a treatment.

The term "determining the level" of a biomarker as used herein, preferably means methods which include quantifying an amount of at least one substance in a sample from a subject and/or quantifying an amount of said substance contained in a part of the body of the subject, such as saliva, blood, lymph, serum, plasma or liquor and/or quantifying an amount of said substance in the subject, the substance being selected from the group comprising a biomarker.

It will be understood by a person skilled in the art that detecting and/or determining the level of free lyso-sphingomyelin and/or compound 509 in a sample from the subject, thus preferably comprises that sphingomyelin present in the blood of a subject is not chemically converted, transformed or derivatized such that free lyso-sphingomyelin and/or compound 509 cannot be detected and/or the level thereof cannot be determined separate from and/or apart from sphingomyelin. The person skilled in the art will acknowledge that sphingomyelin present in a sample from a subject which is subjected to a step of deacetylation, e.g. by hydrolysis in methanolic sodium hydroxide, will result in cleavage of the fatty acid moiety from the sphingomyelin and thus will undesirably result in a chemically converted, transformed or derivatized form of sphingomyelin which cannot be differentiated from free lyso-sphingmyelin. It is thus the merit of the present inventors to recognize that free lyso-sphingomyelin and/or compound 509 apart from sphingomyelin is useful in a method for diagnosing Niemann-Pick disease.

In a preferred embodiment of the methods of the present invention the method is for detecting and/or determining the level of free lyso-sphingomyelin and/or compound 509 in a sample from a subject, wherein sphingomyelin present in the sample from the subject is not subjected to a step resulting in deacetylation of sphingomyelin, preferably is not subjected to a step resulting in cleavage off of a fatty acid moiety from the sphingomyelin contained in the sample. In a further preferred embodiment of the method of the present invention sphingomyelin present in the sample from the subject is not chemically converted, transformed or derivatized. In a still further preferred embodiment of the method of the present invention free lyso-sphingomyelin and/or compound 509 present in the sample from the subject is separated from sphingomyelin present in the sample from the subject prior to a step that would result in cleavage of a fatty acid moiety from the sphingomyelin and/or prior to a step in which sphingomyelin is chemically converted, transformed or derivatized. In a still further preferred embodiment a step of detecting and/or determining the level of a biomarker in a sample from the subject, wherein the biomarker is free lyso-sphingomyelin and/or compound 509, is performed subsequent to separation using HPLC by application of mass spectrometric analysis.

In an embodiment of the methods of the invention a subject will be considered to be healthy regarding Niemann-Pick disease type A or B, if it has no mutation of the functional parts of the SMPD1 gene and/or no mutation of the SMPD1 gene resulting in a reduction of or deficiency of the respective protein or the activity thereof, resulting in symptoms associated with Niemann-Pick disease type A or B.

A subject is considered to be a healthy subject with regard to Niemann-Pick disease, if the subject does not suffer from symptoms associated with Niemann-Pick disease. Moreover in an embodiment of the methods of the invention a subject will be considered to be healthy regarding Niemann-Pick disease type C, if it has no mutation of the functional parts of the NPC1 and NPC2 genes and/or no mutation of the NPC1 and NPC2 genes resulting in a reduction of or deficiency of the respective proteins or the activity thereof, resulting in symptoms associated with Niemann-Pick disease type C. In certain embodiments of the methods of the present invention, the diagnosis of Niemann-Pick disease type C carrier is concerned. In connection therewith it is important to understand that such patient being a carrier of a mutation as outlined above is not considered to be a healthy subject within the meaning of the present invention although said carrier may not suffer from symptoms associated with Niemann-Pick disease. In certain embodiments of the methods of the present invention Niemann-Pick disease also comprises Niemann-Pick disease type C carrier. It is important to note that the methods of the invention are equally suitable to identify a Niemann-Pick disease type C carrier. The method of the present invention is suitable to diagnose whether or whether not a subject is a Niemann-Pick disease type C carrier. The method of the present invention is further suitable for differentiating, diagnosing and/or differentially diagnosing whether a subject is healthy, is a Niemann-Pick disease type C carrier or is a Niemann-Pick disease patient, more particularly preferably a Niemann-Pick disease type A/B patient and/or a Niemann-Pick disease type C patient.

Said mutations, i.e. mutations of SMPD1, NPC1 or NPC2, will be detected if a sample from the subject is subjected to a genetic testing for such mutations as described herein. In a further embodiment of the present invention a sample from a healthy subject is used as a control sample or as a blank matrix in the methods of the present invention. A blank matrix as used herein is preferably a sample from a healthy subject. Nevertheless it will be understood that such a blank matrix may contain a native level of free lyso-sphingomyelin and compound 509.

In an embodiment of the present invention the level of a biomarker is indicative for the subject for suffering from or for being at risk for developing a disease or disorder. The level of the biomarker determined by the method according to the present invention is compared to a control level of the biomarker, wherein the result of said comparison allows for diagnosing a disease.

More specifically, comparing the level of the biomarker in the sample from the subject to the control level of the biomarker comprises comparing the level of the biomarker in the sample from the subject to a cut-off value, wherein if a level of the biomarker in the sample from the subject is elevated, increased or higher compared to the cut-off value, this is indicative that the subject is suffering from or is at risk for developing Niemann-Pick disease, and/or preferably Niemann-Pick disease type A and B, Niemann-Pick disease type C, and/or Niemann-Pick disease type C carrier; and/or wherein if a level of the biomarker in the sample from the subject is decreased or lower compared to the cut-off value this is indicative that the subject is not suffering from or is not at risk for developing Niemann-Pick disease.

The same applies if a ratio of two biomarkers according to the present invention is compared to a cut-off value, wherein if a level of the biomarker in the sample from the subject is elevated, increased or higher compared to the cut-off value, this is indicative that the subject is suffering from or is at risk for developing Niemann-Pick disease, and/or preferably Niemann-Pick disease type A and B, Niemann-Pick disease type C, and/or Niemann-Pick disease type C carrier, most preferably Niemann-Pick disease type C.

The term "being at risk for developing a disease" as used herein preferably means that it is likely that a subject suffer from said disease and/or will develop said disease or symptoms associated with said disease, particularly if no treatment is applied. In connection therewith it has to be acknowledged that LSDs are genetic disorders and thus the occurrence of relatives, particularly parents having said disease or having a mutation known to be the cause of said disease are indicative for a subject, e.g. the child of two Niemann-Pick-disease type C patients, to be at risk for developing said disease. It will be furthermore acknowledged that the progression of a disease is linked to the occurrence of symptoms as well as the severity of said symptoms. Accordingly, a person not suffering from symptoms at present, however, may be at risk for developing the disease, for example, because although genetically mutations of a gene, known to cause a disease are present, no symptoms or no severe symptoms occur. Nevertheless, it will be immediately understood that the methods and biomarkers of the present invention, particularly if the level(s) of said biomarker(s) according to the present invention are elevated, allow for diagnosing that such subject is at risk for developing the disease independent from the presence or absence of symptoms. Accordingly, the methods according to the present invention allows for determining whether a subject is at risk of suffering from Niemann-Pick disease. It is also within the present invention that a therapy is applied, maintained, reduced, elevated or not applied based on whether the subject is at risk of suffering from Niemann-Pick disease or not.

It is also within the present invention that comparing the level of the biomarker in the sample from the subject to a control level allows for determining the severity of Niemann-Pick disease, wherein if a level of the biomarker in the sample from the subject is elevated, increased or higher compared to the control level that is indicative that the subject is suffering from or is at risk for developing Niemann-Pick disease of a more severe status or progression; and wherein if a level of the biomarker in the sample from the subject is decreased or lower compared to the control level that is indicative that the subject is suffering from or is at risk for developing Niemann-Pick disease of a less severe status or progression. In a further embodiment of the present invention that comparing the level of the biomarker in the sample from the subject to the control level comprises comparing a level of the biomarker in said subject to a level of the biomarker detected in a sample from a control, wherein if a level of the biomarker in the sample from the subject is elevated, increased or higher compared to the control sample this is indicative that the subject is suffering from and/or is at risk for developing Niemann-Pick disease; and/or a level of the biomarker in the sample from the subject is elevated, increased or higher compared to the control sample this is indicative that the subject is suffering from or is at risk for developing Niemann-Pick disease of a more severe status or progression. Said control preferably is selected from the group comprising healthy subjects, subjects suffering from Niemann-Pick disease or being at risk of suffering from Niemann-Pick disease symptoms, subjects being positively tested for a mutation or a combination of mutations of the genes SMPD1, NPC1 and NPC2, wherein the mutation or the combination of mutations of the genes SMPD1, NPC1 and NPC2 are indicative for a perspective of the subject to develop Niemann-Pick disease type C of a more severe or less severe status or progression. In a further embodiment of the present invention that a control level is determined in a sample from a control, wherein optionally free lyso-sphingomyelin and/or compound 509 is added to the sample from the control in a specific quantity prior to determining the level of free lyso-sphingomyelin and/or compound 509 in the sample from the control.

It is the merit of the present inventors that a method for diagnosing Niemann-Pick disease in a subject could be established wherein the method comprises detecting a biomarker in a sample from a subject, wherein the biomarker is free lyso-sphingomyelin and/or compound 509, preferably further comprising determining a level of the biomarker in the sample from the subject, and more preferably further comprising comparing the level of the biomarker in the sample from the subject to a cut-off value, which shows high sensitivity, i.e. a sensitivity of at least 99.0%, 99.1%, 99.2%, 99.3%, 99.4%, 99.5%, 99.6%, 99.7%, 99.8%, 99.9% or 100%. In other words the sensitivity, which means the proportion of actual positives which are correctly identified as such is high, which means that the percentage of Niemann-Pick disease patients correctly identified as having the disease is as high as has been outlined above. In contrast, in a statistic test as described herein specificity means the proportion of negatives which are correctly identified as negatives, in other words the percentage of healthy patients correctly identified as not having Niemann-Pick disease. A person skilled in the art will acknowledge that thus an optimal prediction of a diagnostic test such as in some embodiments of the methods according to the present invention in general aims to achieve 100% sensitivity, i.e. predict all patients having a disease, such as Niemann-Pick disease or being at risk of suffering from said disease, as having the disease or being at risk from suffering from said disease, respectively.

In an embodiment of the methods according to the present invention a specificity of at least 80.0%, 85.0%, 90.0%, 95.0%, 97.5%, 99.0%, 99.1%, 99.2%, 99.3%, 99.4%, 99.5%, 99.6%, 99.7%, 99.8%, 99.9% or 100% is preferred. In a further embodiment of the present invention of the methods according to the present invention the methods allow for diagnosing Niemann-Pick disease in a subject independent from a progression status of Niemann-Pick disease in the subject. More specifically, the methods of the present invention allow for diagnosing Niemann-Pick disease in a subject having an early status of Niemann-Pick disease as well as in a subject having an advanced or progressed status of Niemann-Pick disease.

The power of a method to correctly diagnose Niemann-Pick disease, more particularly Niemann-Pick disease type A and B or Niemann-Pick disease type C or Niemann-Pick disease type C carrier, is commonly measured as the sensitivity of the method, the specificity of the method or the area under a receiver operated characteristic curve (also referred to herein as "ROC curve"). An ROC curve is a plot of the true positive rate against the false positive rate for the different possible cut-off values of a diagnostic method. An ROC curve shows the relationship between sensitivity and specificity. Sensitivity is the percentage of true positives that are predicted by a test to be positive, while specificity is the percentage of true negatives that are predicted by a test to be negative. An ROC-curve provides the sensitivity of a test as a function of 1-specificity. The greater the area under the ROC-curve the more powerful the predictive value of the test. Accordingly, an increase in sensitivity will be accompanied by a decrease in specificity. The closer the curve follows the left axis and then the top edge of the ROC space, the more accurate the test. Conversely, the closer the curve comes to the 45-degree diagonal of the ROC graph, the less accurate the test. Therefore, the area under the ROC is a measure of test accuracy. The accuracy of the test depends on how well the test separates the group being tested into those with and without the disease in question. An area under the curve (also referred to herein as "AUC") of 1 represents a perfect method, while an area of 0.5 represents a less useful method. Thus, preferred diagnostic methods of the present invention have an AUC greater then 0.50, more preferred methods have an AUC greater than 0.9 and most preferred methods have an AUC greater than 0.97.

Other useful and suitable measures for the utility of a method are positive predictive value and negative predictive value. A positive predictive value is the percentage of actual positives that test as positive. A negative predictive value is the percentage of actual negatives that test as negative.

A person skilled in the art will acknowledge that although the specificity and/or the sensitivity of the methods according to the present invention are as high as described above and were determined as described in the Examples hereinafter, individual cases may not be excluded where a patient having Niemann-Pick disease will be tested false negative or where a patient not having Niemann-Pick disease will be tested false positive with a method of the invention. A person skilled in the art will thus immediately acknowledge that according to the methods according to the present invention, wherein a level of a biomarker or a ratio of levels of two biomarkers is compared to a cut-off value and wherein said comparison to said cut-off value is for use to differentially diagnose a disease, comprising each and any one of Niemann-Pick disease type A and B, Niemann-Pick disease type C and Niemann-Pick disease type C carrier, said cut-off value represents a level of said biomarker and/or a value of said ratio which discriminates a particularly disease from another, e.g. which discriminates a level of a biomarker indicative that the subject has Niemann-Pick disease type A or B from a level of a biomarker indicative that the subject has Niemann-Pick disease type C, and/or from a level and/or a value in a healthy subject. Having said this, it is obvious for the person skilled in the art that also according to the methods of the present invention, wherein the method is for differentially diagnosing Niemann-Pick disease type A and B, Niemann-Pick disease type C and/or Niemann-Pick disease type C carrier individual cases may not be excluded where a patient having Niemann-Pick disease will be tested false negative or where a patient not having Niemann-Pick disease will be tested false positive, or where the type and/or status is diagnosed incorrectly with a method of the invention.

Taking said cases into account while determining the specificity and the sensitivity of the method according to the present invention, the specificity and the sensitivity will be lower than the above described values. Nevertheless, the person skilled in the art will also acknowledge that such high specificity and such high sensitivity as has been outlined above has never been described before for a method for diagnosing Niemann-Pick disease. Therefore it is important to note that although the sensitivity and the specificity of the method of the present invention may vary if patient collectives other than the one reported in the Example part, e.g. varying in number of patients, will are subject to the methods of the present invention, it is the firm belief of the inventors that no method known in the prior art using, especially using biomarkers will achieve a higher specificity and a higher sensitivity compared to the methods according to the present invention. This is especially true since the limit of detection of the methods of the present invention allows for determining the level of free lyso-sphingomyelin and compound 509 in healthy subjects. Accordingly, a diseased subject tested false negative applying the methods of the present invention is tested false negative for the reason that a level of the biomarker in a sample from said false negative tested diseased subject is as high as the level of the biomarker in a sample from a healthy subject. In particular it is important to note that said false negative tested subject is not tested negative for the reason that the level of the biomarker was too low to be determined by the method of the present invention.

A "limit of detection" of a substance such as free lyso-sphingomyelin and/or compound 509, as used herein, preferably is a level of the substance determined by a method for determining a level of the substance, wherein a level less then or lower then said limit of detection cannot be determined by said method. It is thus immediately clear that a "cut-off value" and a "limit of detection", as used herein, are preferably not necessarily identical, although both reflect a certain level of a substance, e.g. of a biomarker of the present invention. It will be immediately understood that in contrast to a cut-off value will be selected preferably such that selectivity and sensitivity of the method are as high as possible. In contrast thereto a limit of detection represents an absolute level of the biomarker of the present invention which reflects the minimum level of biomarker which can be detected with a method for determining the level of said biomarker. It is thus immediately clear that a limit of detection depends on the method for determining a level of a substance and on the substance the level of which is to be determined by the method. A skilled person will immediately understand that a high limit of detection, e.g. higher than an ideal cut-off value would possibly result in a low sensitivity of the method since the percentage of true positives that are predicted by a test to be positive also depends on whether a level of the biomarker may be determined for said true positives. In other words, if the limit of detection is higher than an ideal cut-off value, true positives having a level of the biomarker slightly higher than the cut-off value may not be distinguished from true negatives having a level of the biomarker lower than the cut-off value since no level of the biomarker may be determined for both true positives having a level of the biomarker slightly higher than the cut-off value and negatives having a level of the biomarker lower than the cut-off value. It is thus immediately clear that a low limit of detection is of advantage. It is therefore also the merit of the inventors to show that a lower limit of detection allows for a method for diagnosing Niemann-Pick disease in a subject comprising a step of determining a level of a biomarker present in the sample with higher selectivity and sensitivity. An "ideal cut-off value" as used herein, preferably is the cut-off value as described herein the method using said ideal cut-off value has the highest selectivity and sensitivity.

It is an embodiment of the methods according to the present invention to comprise a step of validating said method by diagnosing a disease or disorder, preferably Niemann-Pick disease in a subject by the method of the present invention; a step of diagnosing the disease or disorder, preferably Niemann-Pick disease, in a subject by a genetic testing, comprising sequencing of a gene, preferably sequencing of a gene a mutation of which is known to the one skilled in the art to cause the disease or disorder, more preferably sequencing the NPC1 and NPC2 genes in case of Niemann-Pick disease type C and Niemann-Pick disease type C carrier and the gene SMPD1 in case of Niemann-Pick disease type A and B; and comparing the results of said method and said genetic testing. A healthy subject as used herein, preferably is considered to be healthy with regard to a disease or disorder if said subject is not suffering from symptoms associated with said disease or disorder and if the result of a genetic testing reveals no mutations of a gene a mutation of which is known to the one skilled in the art to cause the disease or disorder. A healthy subject also is understood to be a subject being positively tested for not having Niemann-Pick disease. In a preferred embodiment a healthy subject is a subject not being a carrier of Niemann-Pick disease, more preferably not being a Niemann-Pick disease type C carrier.

The term "qualifying Niemann-Pick disease status" in a subject as used herein, preferably means a classification of a subject's biomarker profile selected from the group comprising to identify or detect the presence or absence of Niemann-Pick disease in the subject, to predict the onset of or the risk for developing of Niemann-Pick disease in the subject, to determine the course of Niemann-Pick disease in a subject, to determine and/or predict the severity of Niemann-Pick disease in a subject, to determine whether a subject suffers from an early status of Niemann-Pick disease or an advanced or progressed status of Niemann-Pick disease or to determine whether a level of a biomarker in a subject has significantly changed over time.

The term "managing subject treatment" or "subject management" as used herein, preferably refers to the behavior of the clinician or physician subsequent to the determination of Niemann-Pick disease status. For example, if the result of the method according to the present invention is inconclusive or there is reason that confirmation of status is necessary, the physician may order new tests, such as testing for the function of the affected proteins and/or sequencing of the SMPD1, NPC1 and NPC2 genes, respectively. Alternatively, if the status indicates that treating for Niemann-Pick disease is appropriate, the physician may schedule the subject for treating for Niemann-Pick disease type A and B or Niemann-Pick disease type C. Likewise, if the status is negative or if the results show that treatment has been successful, no further management may be necessary. Nevertheless a person skilled in the art will immediately acknowledge that besides gene therapy any therapy applied. Furthermore it is an embodiment of the present invention that managing subject treatment comprises titrating of a dose of a drug applied as a treatment for Niemann-Pick disease, e.g. units of recombinant enzyme applied in ERT, administered to a patient. In some embodiments of the methods of the present invention wherein a level of a biomarker present in a sample from a subject and/or a ratio of the levels of two biomarkers is determined at several points in time, or is compared to other levels of the biomarker, a cut-off value and/or a level of said biomarker in a control and/or another value of a ratio of the levels of two biomarkers, a skilled person will apply or not apply a therapy, or amend a therapy already applied in order to treat or not to treat, or to continue treating Niemann-Pick disease.

It is within the present invention that a skilled person will apply a dosage and/or maintain a dosage or amend a dosage, e.g. apply a dosage or a higher dosage, i.e. elevate a dosage, if such a comparison of the level of a biomarker and/or the ratio of the levels of two biomarkers shows e.g. that the level of said biomarker and/or the ratio of the levels of two biomarkers is higher than for example, a cut-off value, i.e. the patient is diagnosed to have Niemann-Pick disease; or that a level and/or ratio determined in the same patient earlier in time is lower or the same, i.e. a therapy applied is not sufficient, i.e. does not result in a decrease in the level. On the other hand skilled person will apply or not apply a dosage or maintain or reduce a dosage, e.g. apply no dosage or a lower dosage, i.e. decrease a dosage, if such a comparison of the level and/or the ratio of the level of a/two biomarker shows e.g. that the level of said biomarker and/or the ratio of the levels of two biomarkers is lower than for example, a cut-off value, i.e. the patient is diagnosed not to have Niemann-Pick disease; or that a level and/or a ratio determined in the same patient earlier in time is higher, i.e. a therapy applied is sufficient, i.e. does result in a decrease in the level. In an embodiment of the present invention a relatively high level of free lyso-sphingomyelin and/or compound 509 based on such a comparison is indicative for applying a high dosage of recombinant enzyme applied in ERT and/or a relatively low level of free lyso-sphingomyelin and/or compound 509 based on such a comparison is indicative for applying a low dosage of recombinant enzyme applied in ERT. Nevertheless it will also be immediately understood that a skilled person will consider a patient's history, i.e. a skilled person managing subject treatment of a patient suffering from Niemann-Pick disease and being treated such that a level of biomarker and/or a ratio of the levels of two biomarkers is lower than a cut-off value, for example, will not decide to stop treatment rather than decrease a dosage and increase the time between further applications of the methods of the present invention.

The course of Niemann-Pick disease may be determined by the method according to the present invention by determining a level of the biomarker and/or a ratio of the levels of two biomarkers in the sample from the subject at different time points in the course of the disease. It is important to note that a single application of a method for diagnosing Niemann-Pick disease according to the present invention allows for diagnosing Niemann-Pick disease and in certain embodiments comprises a step of managing subject treatment based on the diagnosis of whether the subject is suffering from or for being at risk for developing Niemann-Pick disease. If a subject a sample of which is thus subjected to the method of the present invention is tested positive for suffering from or to be at risk for developing Niemann-Pick disease a skilled clinician will know how to decide concerning managing subject treatment, i.e. how the subject will be treated, e.g. applying a certain dose of enzyme in relation to an ERT. It will be immediately understood that independent of the decision of a skilled clinician on how to manage subject treatment the skilled clinician may decide for at least one additional application of the method according to the present invention on a later time point. It is thus an embodiment of the present invention that the levels of the biomarker and/or a ratio of the levels of two biomarkers determined at the different time points, wherein different time points means at least two time points, may be compared. Without wishing to be bound by any theory the present inventors have found that the level of the biomarker of the present invention and/or a ratio of the levels of two biomarkers in samples form one particular patient may be correlated to the severity of the disease in said patient at the time point the sample from the patient is taken. It will be thus immediately understood that an elevated level of the biomarker and/or an elevated ratio of the levels of two biomarkers determined in the sample of a later time point compared to the level of the biomarker and/or the ratio of the levels of two biomarkers determined in the sample of an earlier time point is indicative for a more severe status of the subject at the later time point compared to the status of the subject at the earlier time point. A decreased level of the biomarker and/or ratio of the levels of two biomarkers determined in the sample of a later time point compared to the level and/or the ratio of the levels of two biomarkers of the biomarker determined in the sample of an earlier time point is indicative for a less severe status of the subject at the later time point compared to the status of the subject at the earlier time point. Accordingly, in one aspect the present invention provides a method for determining the course of Niemann-Pick disease in a subject comprising the step of determining at several points in time a level of a biomarker and/or a ratio of the levels of two biomarkers present in a sample from the subject, wherein the biomarker is free lyso-sphingomyelin and/or compound 509. In a further aspect the invention concerns a method for determining the effectiveness of at least one treatment applied to a subject being positively tested for suffering from or being at risk for developing Niemann-Pick disease comprising the step of determining at several points in time a level of a biomarker and/or a ratio of the levels of two biomarkers present in a sample from the subject, wherein the biomarker is free lyso-sphingomyelin and/or compound 509. It will be immediately understood by a person skilled in the art that the methods of the present invention thus allow for selecting a therapy and/or adjusting the doses and/or dosage of a selected therapy based on the results of the method of the invention. If for example the subject is scheduled for treating for Niemann-Pick disease the method for diagnosing Niemann-Pick disease in a subject according to the present invention may be applied every 3 months and levels of the biomarker and/or a ratio of the levels of two biomarkers thus determined will be compared in order to determine the effectiveness of the treatment(s) and/or therapy/therapies applied to the subject. If the subject reaches a status, wherein a stable level of the biomarker and/or a stable ratio of the levels of two biomarkers is maintained over time the frequency of application of the method for diagnosing Niemann-Pick disease in a subject according to the present invention may be reduced to every 6 month. If the dosage of the therapy is changed, e.g. the units of recombinant enzyme applied in ERT are reduced or increased, the frequency of application of the method for diagnosing Niemann-Pick disease in a subject according to the present invention may be set back to every 3 month. By comparison of the determined levels of the biomarker and/or ratios of the levels of two biomarkers in the samples from the subject the skilled physician will recognize whether the level of the biomarker and/or the ratio of the levels of two biomarkers increases, decreases or whether a stable level of the biomarker and/or a stable ratio of the levels of two biomarkers is maintained over time. Accordingly, the skilled physician may decide to reduce the dosage of the therapy, e.g. the units of recombinant enzyme applied in ERT; to increase the dosage of the therapy; or to maintain the dosage of the therapy according to the comparison of the levels of the biomarker and/or the ratios of the levels of two biomarkers determined with the method according to the present invention. A reduction of about 60% of the level of free lyso-sphingomyelin and/or compound 509 within a period of 12 month is indicative for a successful therapy for Niemann-Pick disease, wherein reduction as used herein, preferably means that the level of free lyso-sphingomyelin and/or compound 509 determined by the method of the present invention determined at the end of a time period is compared to the level of free lyso-sphingomyelin and/or compound 509 determined by the method of the present invention determined at the beginning of said time period. Accordingly the skilled physician may decide to reduce the dosage of the applied therapy or to maintain the dosage of the therapy. If the reduction of the level of free lyso-sphingomyelin and/or compound 509 is significantly weaker the skilled physician may decide to increase the dosage of the therapy. It is also a merit of the present inventors to have recognized that the reduction of the level of free lyso-sphingomyelin and the reduction of compound 509 correlates with the effectiveness of a therapy. The stronger the reduction of the level of the free lyso-sphingomyelin and/or the stronger the reduction of the level of the compound 509 within a time period, e.g. 12 months, the more successful is a therapy, such as for example ERT, SRT or a chaperone based therapy. It is thus a further embodiment of the present invention that the method of the present invention is for comparing the effectiveness of a therapy or of at least two therapies applied to a subject.

A person skilled in the art thus will acknowledge that the progression, i.e. course of Niemann-Pick disease, as well as the effectiveness of a therapy in a single subject can be monitored by frequent determining of the level of free lyso-sphingomyelin and/or compound 509 and/or the ratio of the levels of two biomarkers in samples from the subject.

In a further aspect the invention concerns a method for determining the effectiveness of at least one treatment applied to a subject being positively tested for suffering from or being at risk for developing Niemann-Pick disease comprising the step of determining at several points in time a level of a biomarker and/or the ratio of the level of two biomarkers present in a sample from the subject, wherein the biomarker is free lyso-sphingomyelin and/or compound 509. In connection with what has been outlined above in relation to managing subject treatment a person skilled in the art will immediately understand that the effectiveness of one treatment or the combination of at least two treatments may be compared applying the methods of the present invention. Thus it is possible to test and compare several new drugs, dosage forms, dosages or treatments for Niemann-Pick disease by the method of the present invention.

It is an embodiment of the present invention that the method for diagnosing Niemann-Pick disease according to the present invention is independent of whether the subject has or has not been previously treated for Niemann-Pick disease. Thus the sample from the subject may be a sample from a subject who has been previously treated for Niemann-Pick disease as well as a sample from a subject who has not been previously treated for Niemann-Pick disease. It is thus a further embodiment of the present invention that the method of the present invention comprises a step of managing subject treatment and/or determining a level of the biomarker and/or a ratio of the levels of two biomarkers in the sample from the subject after subject management. Said subject treatment can be based on the diagnosis of whether the subject is suffering from or for being at risk for developing Niemann-Pick disease; on the detection of the biomarker in a sample from the subject after subject management; or on the determining of the level of the biomarker and/or the ratio of the levels of two biomarkers in the sample from the subject after subject management. Nevertheless a person skilled in the art will understand that a sample of some patients not having Niemann-Pick disease or of some patients being successfully treated for Niemann-Pick disease will show a level of free lyso-sphingomyelin and compound 509 lower than the limit of detection.

Without wishing to be bound by any theory the present inventors assume that the level of free lyso-sphingomyelin and the level of compound 509 and the ratio of the level of compound 509 to the level of free lyso-sphingomyelin, respectively, present in a sample from a subject further correlates with the severity of the disease in a subject suffering from Niemann-Pick disease. In connection therewith the present inventors assume that although, in principle, the level of free lyso-sphingomyelin, the level of compound 509 and/or the ratio of the level of compound 509 to the level of free lyso-sphingomyelin is different in particular individuals, and more specifically may be different in particular individuals having the same mutation(s), that the higher is a level of free lyso-sphingomyelin, a level of compound 509 and a ratio of the level of compound 509 to the level of free lyso-sphingomyelin, respectively, the higher is the severity of a course of Niemann-Pick disease in terms of a statistical mean according to a clinical score. Thereby the level of free lyso-sphingomyelin, the level of compound 509 and/or the ratio of the level of compound 509 to the level of free lyso-sphingomyelin, respectively, correlates with the severity of Niemann-Pick disease in that in patients being positively tested for distinct mutations of the SMPD1, NPC1 and NPC2 genes, respectively, being known to generally causes a mild or a more severe course of Niemann-Pick disease, a level of free lyso-sphingomyelin, a level of compound 509 and/or a ratio of the level of compound 509 to the level of free lyso-sphingomyelin, respectively, determined in said patients statistically correlates with the severity generally related to such mutation.

Thus a further embodiment of the different aspects of the present invention concerns a method for determining the severity of Niemann-Pick disease in a subject comprising a step of
  a) determining a level of the biomarker and/or a ratio of the levels two biomarkers present in a sample from the subject wherein the biomarker is free lyso-sphingomyelin and/or compound 509 and a step of
  b) determining the severity of Niemann-Pick disease, e.g. by comparing the level of free lyso-sphingomyelin and/or compound 509 and/or the ratio of the levels two biomarkers in a subject preferably determined by a method of the present invention to a clinical score.

In connection therewith it is important to note that if a level of free lyso-sphingomyelin, the level of compound 509 and/or the ratio of the level of compound 509 to the level of free lyso-sphingomyelin, respectively, is determined in samples from the patients suffering from Niemann-Pick disease showing a mutation usually linked to a more severe course of Niemann-Pick disease upon sequencing of the respective gene (homozygous and compound heterozygous) subjected to a method of the present invention a mean-level of free lyso-sphingomyelin, compound 509 and/or the ratio of the level of compound 509 to the level of free lyso-sphingomyelin, respectively, is higher than the mean-level of the free lyso-sphingomyelin, compound 509 and/or the ratio of the level of compound 509 to the level of free lyso-sphingomyelin, respectively, determined in samples from the patients suffering from Niemann-Pick disease showing a mutation usually linked to a more mild course of Niemann-Pick disease upon sequencing of the respective gene, applying the same method. A "mutation usually linked to a more severe course of Niemann-Pick disease" as used herein preferably is known to cause a more severe course of Niemann-Pick disease—this is especially true in case the subject is homozygous as to said mutation. Corresponding to that in an embodiment a higher mean-level of free lyso-sphingomyelin, compound 509 and/or the ratio of the level of compound 509 to the level of free lyso-sphingomyelin, respectively, is determined in the homozygous compared to the homozygous mutation usually linked to a more mild course of Niemann-Pick disease. Moreover patients having a compound heterozygous usually linked to a more severe course of Niemann-Pick disease have a significant lower free lyso-sphingomyelin level, compound 509 level and/or ratio of the level of compound 509 to the level of free lyso-sphingomyelin, respectively, than homozygous ones. A person skilled in the art will know clinical scores to categorize the severity of Niemann-Pick disease or symptoms or an entirety of symptoms thereof. It is thus an embodiment of the method of the present invention that the course of Niemann-Pick disease in a patient is predicted and more particularly the severity of Niemann-Pick disease is determined based on the level of the biomarker determined according to the method of the present invention.

A person skilled in the art will acknowledge that a level of the biomarker of the present invention determined in a sample from a subject wherein said level of the biomarker is correlated with the severity of Niemann-Pick disease as described above, will be indicative for applying a certain therapy and/or dose or dosage of said therapy. For example, if the level of the biomarker and/or the ratio of the levels of two biomarkers determined according to the methods of the invention is correlated with "severe" Niemann-Pick disease status the subject is scheduled for treatment of Niemann-Pick disease and the method for diagnosing Niemann-Pick disease in a subject according to the present invention may be applied every 3 months and levels of the biomarker thus determined will be compared in order to determine the effectiveness of the treatment(s) and/or therapy/therapies applied to the subject. If the subject reaches a status, wherein the level of the biomarker and/or the ratio of the levels of the two biomarkers, respectively, is correlated with a "mild" Niemann-Pick disease or wherein a stable level and/or ratio of the biomarker is maintained over time the frequency of application of the method for diagnosing Niemann-Pick disease in a subject according to the present invention may be reduced to every 6 month.

In another aspect the present invention is related to a method of determining the effectiveness of a composition for the treatment of Niemann-Pick disease. Such method may comprise the steps of determining a level of free lyso-sphingomyelin and/or compound 509 and/or a ratio of the level of compound 509 to the level of free lyso-sphingomyelin, respectively, in a subject having Niemann-Pick disease; administering to said subject said compound in an amount sufficient to determine the effectiveness of said compound; re-determining the level of free lyso-sphingomyelin and/or compound 509 and/or the ratio of the levels of compound 509 to the level of free lyso-sphingomyelin, respectively, in said subject; comparing the level of free lyso-sphingomyelin and/or compound 509 and/or the ratio of the levels of compound 509 to the level of free lyso-sphingomyelin, respectively, determined before and after administering said composition, wherein a lower level of free lyso-sphingomyelin and/or compound 509 and/or a lower ratio of the levels of compound 509 to the level of free lyso-sphingomyelin, respectively, determined after administering said composition compared to the level of free lyso-sphingomyelin and/or compound 509 and/or the ratio of the levels of compound 509 to the level of free lyso-sphingomyelin, respectively, determined after administering said composition indicates the effectiveness of said compound for treating Niemann-Pick disease.

Niemann-Pick disease affects mostly children and they often die at a young and unpredictable age, many within a few months or years of birth. Many other children die of this disease following years of suffering from various symptoms of their disorder.

A preferable biomarker for the diagnosis of Niemann-Pick disease, preferably Niemann-Pick disease type C, would allow for diagnosis of Niemann-Pick disease, preferably Niemann-Pick disease type C, with high sensitivity and high specificity independent from the age of the subject.

It is the merit of the present inventors having found that the biomarkers of the present invention are useful for the diagnosis of Niemann-Pick disease in a subject independent from the age of the subject. It is thus an embodiment of the present invention that the method of the present invention allows for diagnosing Niemann-Pick disease in a subject independent from age. In a preferred embodiment the method of the present invention the subject is a subject of young age. A subject of young age as used herein preferably is a subject of less than 30 years of age, more preferably of less than 20 years of age and most preferably of less than 10 years of age.

The present invention is now further illustrated by the following figures and examples from which further features, embodiments and advantages may be taken.

More specifically,

Figure 1:
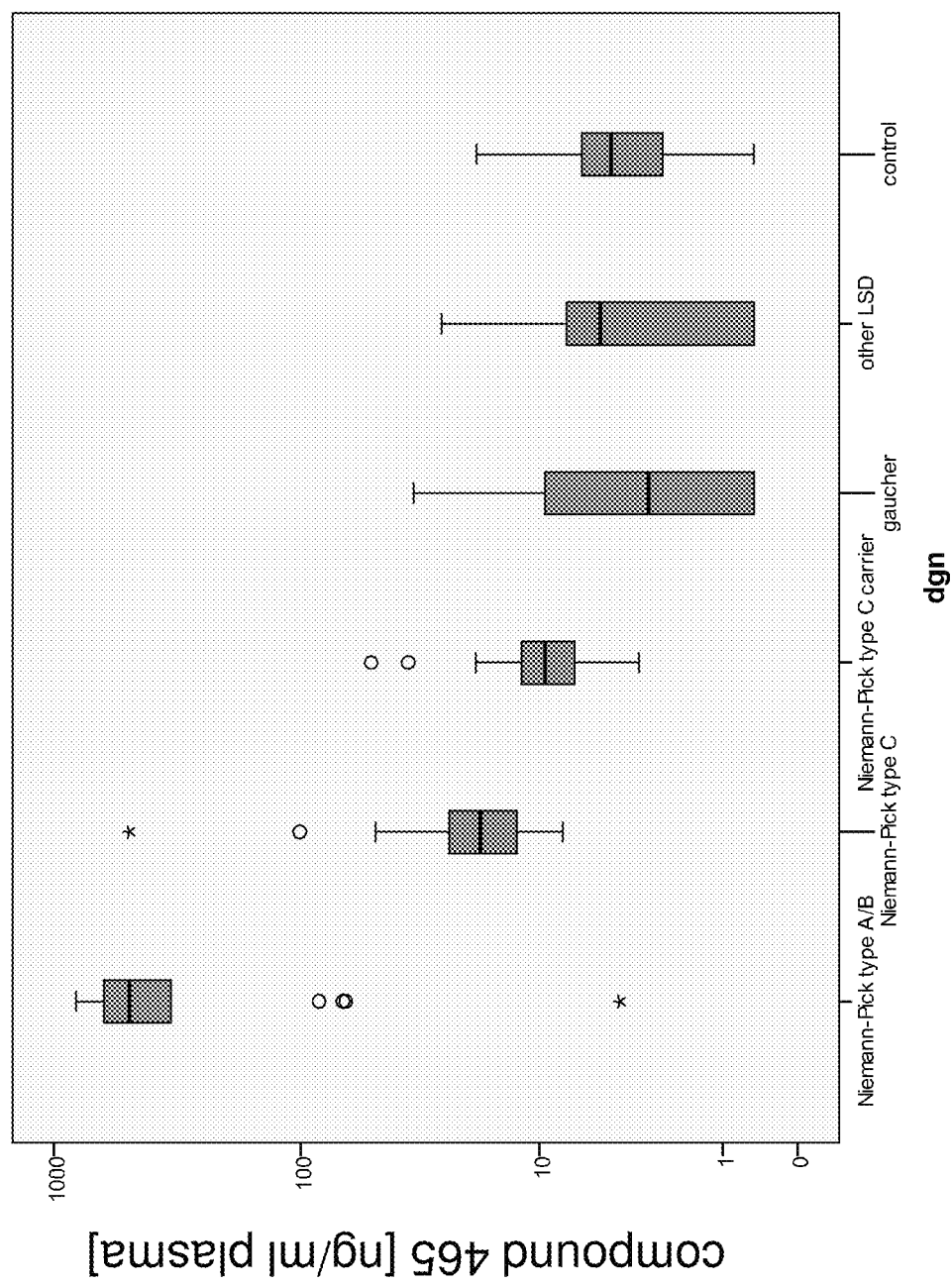
FIG. 1 is a boxplot indicating levels of compound 465 in ng/ml plasma.

FIGS. 8A(1)-8A(3) are HPLC-mass spectrometric chromatogram displaying peak intensity of free lyso-sphingomyelin, compound 509 and IS of a healthy subject;

FIGS. 8B(1)-8B(3), 8C(1)-8C(3), 8D(1)-8D(3) and 8E(1)-8E(3) are HPLC-mass spectrometric chromatograms displaying peak intensity of free lyso-sphingomyelin, compound 509 and IS of Niemann-Pick disease type C patient;

FIGS. 9A, 9B, 9C and 9D are boxplots or scatterplots indicating levels of compound 465 or compound 509 in ng/ml plasma depending on the age of the patients.

EXAMPLES

In the Examples described in the following human plasma was used as a sample from a subject. Nevertheless a person skilled in the art will acknowledge that depending on the used type of sample from a subject, e.g. comprising saliva, liquor, plasma, serum, full blood, blood on a dry blood filter card or another blood product, the method of the present invention has to be adjusted to the type of sample and furthermore a cut-off value has to be determined for each type of sample according to the method described in the following examples. The present inventors have found that using a sample of human serum in the method as described below instead of a sample of human plasma will lead to identical results in terms of the level of free lyso-sphingomyelin and compound 509, respectively, if the sample of human serum and the sample of human plasma are taken from the same subject, at the same time point, and if the samples were measured in parallel; and, more particularly, will lead to the same cut-off value.

Example 1: Method for the Detection of Free Lyso-Sphingomyelin and/or Compound 509 in Human Serum Equipment For detecting free lyso-sphingomyelin and/or a substance with molecular weight of 508, detected as MRM transition in positive mode 509 m/z to 184 m/z, also referred to herein as compound 509 in a sample of plasma from a subject the following equipment was used.

| Apparatus/Piece of Equipment | Type/Producer |
|---|---|
| HPLC pump | Series 200, Perkin Elmer, USA |
| Sample injector | Series 200, Perkin Elmer, USA |
| Column oven | Series 200, Perkin Elmer, USA |
| Mass selective detector | API 4000 Q TRAP, AB SCIEX, USA/Canada |
| Multi-tube vortexer DVX-2500 | Henry Troemner LLC, USA |
| Vortex mixer | Vortex Genie 2; Scientific Industries, USA |
| Centrifuge | Megafuge 1.0; Heraeus, Germany |
| Multipette(s), pipette(s) | Eppendorf, Germany |
| Water bath | SW21-C, Julabo, Germany |

Reagents

For detecting free lyso-sphingomyelin and/or compound 509 in a sample of plasma from a subject the following reagents were used.

To that extent that values depend on temperature (e.g. the pH value) such values were determined at a temperature of 25° C.

| Reagent | Purity |
|---|---|
| Acetonitrile (ACN) | HPLC-grade or Gradient grade |
| Acetone | 99.5% |
| Dimethylsulfoxide (DMSO) | HPLC grade |
| Ethanol (EtOH) | p.a., 96% |
| Formic acid (FA) | p.a., 98-100% |
| Methanol (MeOH) | Gradient (LiChrosolv) |
| Trifluoroacetic acid (TFA) | purum >98% |
| Water | ASTM-I |

The abbreviation "p.a." as used herein means "pro analysis".

The term "purum" as used herein, preferably means a commercial grade of a chemical compound having a purity of the above specified value.

ASTM-I as used herein refers to a water grade standard purity achieved by purification methods comprising Reverse Osmosis and Ultraviolet (UV) Oxidation.

Preparation of Calibration Standards

A Lyso-Sphingomyelin stock solution was prepared by dissolving 2.16 mg Lyso-Sphingomyelin (as delivered by Matreya, purity stated as 95.1%) in 5 mL of MeOH/water (1:4; v/v).

Subsequently the solution V1-A was prepared as a mixture of 74 μL of Lyso-Sphingomyelin stock solution and 5 mL MeOH/water (1:4; v/v) as displayed in the following:

| Label of resulting solution | exp. conc. [µg/mL] | Volume of solution [µL] | solution | volume of solvent [mL] | solvent |
|---|---|---|---|---|---|
| V1-A | 6.0803 | 74 | Lyso-Sphingomyelin-stock | 5 | DMSO/MeOH (1:4; v/v) |

Subsequently the Calibration Standards were prepared by spiking solution V1-A or higher concentrated Calibration Standards into the solvent MeOH/water (1:1; v/v).

A detailed spiking scheme will be displayed in the following.

| Label of resulting solution | concentration [ng/mL] | Volume of solution [µL] | solution | volume of solvent [mL] | solvent | Volume [ml] |
|---|---|---|---|---|---|---|
| Std5A-NPC | 200.26 | 119.2 | V1-A | 3.5 | MeOH/water (1:1; v/v) | 3.0303 |
| Std4A-NPC | 60.002 | 29.9 | V1-A | 3 | MeOH/water (1:1; v/v) | 3.0927 |
| Std3A-NPC | 18.040 | 297 | Std5A-NPC | 3 | MeOH/water (1:1; v/v) | 3.297 |
| Std2A-NPC | 6.0025 | 92.7 | Std5A-NPC | 3 | MeOH/water (1:1; v/v) | 3.0299 |
| Std1A-NPC | 2.0024 | 30.3 | Std5A-NPC | 3 | MeOH/water (1:1; v/v) | 3.6192 |

For calibration, all calibration standards mentioned above having five concentration levels between 2.00 and 200 ng/mL were used.

Preparation of Control Samples

Control samples were prepared by spiking solution V1-A into a blank matrix.

A detailed spiking scheme will be displayed in the following.

| Label of resulting solution | concentration [ng/mL] | Volume of solution [µL] | solution | volume of blank matrix [mL] | Volume [ml] |
|---|---|---|---|---|---|
| QC-A1-NPC | native concentration | | | 3* | |
| QC-B1-NPC | 100.07 | 50.2 | V1-A | 3 | 3.0502 |

*native concentration is below 10 ng/mL, therefore the QC-B1-NPC level is hardly influenced.

Blank Matrix

As a blank matrix, human plasma of a healthy subject was used. A person skilled in the art will acknowledge that said plasma from a healthy subject will contain a native level of free lyso-sphingomyelin and/or a native level of compound 509. Said native level of free lyso-sphingomyelin is about 3.9 ng/ml according to the methods of the present invention. It is thus obvious that control samples prepared by spiking of the blank matrix, the blank matrix comprising said native level of free lyso-sphingomyelin and compound 509, respectively, also comprise said native level of free lyso-sphingomyelin and compound 509 in addition to the level of free lyso-sphingomyelin and/or compound 509 obtained by spiking with a concentrated solution or higher concentrated control sample. Accordingly, the level of free lyso-sphingomyelin in the control samples is as follows:

QC-B1-NPC 100 ng/mL+native concentration in blank matrix

A person skilled in the art will acknowledge that human plasma of a healthy subject used as blank matrix can be purchased at any commercial source known to the one skilled in the art. It is important to note that if accidentally plasma of a non-healthy subject, i.e. of a subject having Niemann-Pick disease, is used as the blank matrix, this will result in unusually high levels of free lyso-sphingomyelin or compound 509 in the control samples determined by the method according to the present invention and thus will be immediately recognized, as the tolerance of the method is determined as being within a range of 15% above or below the estimated levels of the controls subjected to the method according to the present invention.

Study Samples

Preparation of Internal Standard

The Internal Standard (IS1) stock solution was prepared dissolving 1.00 mg of Lyso-Gb2 (as delivered by Matreya) in 2 mL of DMSO/MeOH (1/1; vol/vol).

Subsequently the Internal Standard Working Solution was prepared as a mixture of 410 µL of IS1 stock solution and 500 mL of ethanol. The ethanol may be purchased from any commercial source, wherein the ethanol is absolute ethanol having a grade suitable for the methods described herein. A person skilled in the art will recognize that proteins contained in 50 µl of a sample have to precipitate if 100 µL of said Internal Standard working solution are added to the sample.

Storing of Samples and Solutions

Control samples or study samples either were immediately stored below −20° C. at once or aliquots were transferred into new glass vials before storing under the same conditions.

Concentrated solutions (stock solutions, V1-A-534 etc.) as well as Internal Standard stock solutions were frozen below −20° C. pending next spiking.

Internal Standard working solutions were stored between 2° C. and 8° C. until use.

Without wishing to be bound by any theory the present inventors assume that free lyso-sphingomyelin and/or compound 509, respectively, are stable in the above mentioned solutions. More precisely, the level of lyso-sphingomyelin and the level of compound 509 of a plasma and/or a serum sample of a Niemann-Pick disease patient determined by the methods according to the present invention are found to be identical, if the level of free lyso-sphingomyelin and, respectively, the level of compound 509 is determined in said samples prior to and after storage at 37° C. for 2 days. Accordingly, the solutions and samples of the present invention can be transported in a number of ways well known to one skilled in the art, wherein the use of a cold chain for transportation of patient material is preferred but not necessarily required. A person skilled in the art will also know methods and their respective conditions for appropriate storage of solutions and samples, wherein, for example, said solutions and samples may be stored for several weeks.

Sample Preparation for Analysis

All samples used in an analytical batch are prepared for analysis as follows:
- Frozen samples were thawed at approximately 20 to 25° C. in a water bath taking from ambient conditions. After thawing the samples were mixed.
- 50 µL of the sample were transferred into a sample vial
- 100 µL of Internal Standard working solution (in EtOH) was added to the sample
- The thus obtained mixture was subsequently mixed using a DVX-2500 Multi-tube vortex device at 2500 rpm for about 30 seconds
- The thus obtained mixture was centrifuged for phase separation at 4000 rpm for 2 minutes.
- Transfer of a volume of the supernatant adequate to injection purposes (approx. 100 µL) into appropriate (conical) auto-sampler vials Methods Chromatographic and Auto-Sampler Parameters The samples prepared for analysis as described above were subsequently subjected to the method described in the following:

| Parameter | Scheduled range/description |
| --- | --- |
| Mobile phase solvent A | 50 mM FA in water |
| Mobile phase solvent B | 50 mM FA in ACN/acetone (1:1; vol/vol) |
| Chromatographic run | 0.0-4.0 min linear gradient: 5% B → 66% B |
| | 4.1-5.1 min isocratic: 100% B |
| | 5.1-5.9 min isocratic: 5% B |
| Flow | 0.9 mL/min |
| Injection volume | 5 µL |
| Injector flush | 0.1% TFA in 70% MeOH |
| Column + Precolumn | ACE 3 C8, 50 × 2.1 mm ID + Security Guard C8 |
| Column temperature | 60° C. |
| Retention time | approx. 3.2 to 3.4 min: lyso-Sphingomyelin and lyso-Gb 2 (IS) |
| | approx. 3.6 to 3.9 min: compound 509 |

The ACE 3 C8 column (ACE C8 column Nr. ACE-112-0502) used herein has been purchased from Advanced Chromatography Technologies, Aberdeen.

A sequence as used herein, preferably is a batch of defined numbers of samples, preferably 250 in maximum analyzed sequentially, wherein parameters comprising flow and temperature remain unchanged. Adjustments and calibrations performed between sequences are known to those skilled in the art and comprise exchange of the column.

These adjustments within the specified limits are minor changes and are recorded within the raw data of the study at the measuring station.

Detection

The thus prepared samples were subsequently subjected to the detection method the parameters of which are described in the following:

| | |
| --- | --- |
| MS Ionisation mode: | Electrospray Ionisation (ESI) |
| MS polarity: | positive |
| MS detection mode: | Multiple reaction monitoring (MRM) |
| Vaporizer temperature: | 500° C. ± 50° C. |
| Ionisation voltage: | 5.5 kV |
| Collisionally activated dissociation (CAD) gas: | low |
| Gas 1: | Pressure = 45 psi |
| Gas 2: | Pressure = 60 psi |
| Curtain gas: | pressure = 40 psi |
| Lateral position: | 5 units |
| Vertical position: | 4 units |
| Quadrupole resolution | unit → unit |
| Transitions | 465.4 → 184.1 m/z lyso-Sphingomyelin |
| | 624.5 → 282.2 m/z lyso-Gb2 (Internal Standard) |
| | 509.5 → 184.1 m/z compound 509 |
| Transitions | 462.4 → 282.2 m/z lyso-Gb1 |
| | 624.5 → 282.2 m/z lyso-Gb2 (Internal Standard) |
| DP (declustering potential) | 40 V |
| CXP (collision cell exit potential) | 8 V |

A person skilled in the art will acknowledge that methods for detecting free lyso-sphingomyelin and/or compound 509, and/or determining the level of free lyso-sphingomyelin and/or compound 509 in a sample from a subject using mass spectrometric analysis may also employ other transitions and fragments which allow for specific detection of and/or quantification of free lyso-sphingomyelin and/or compound 509 in said sample from a subject.

Evaluation and Calculation of Results

To evaluate and to calculate results obtained with the above specified methods the following protocol were applied.

Rounding Procedure

Concentration data fed into and retrieved from the chromatographic data system (CDS) were rounded to five significant digits. Further calculations in the spreadsheet were performed to full computational accuracy and subsequently rounded to the significant digits/decimal places to be reported. Hence, deviations of intermediate results might occur caused by rounding. Accuracy and coefficients of variation (CV) will be reported with one and two decimal places, respectively.

Note Referring to the Rounding Procedure:

The last digit reported would be up-rounded if the subsequent digit was equal or greater than "5".

Regression and Statistics

Based on Calibration Standards the calibration curve fitting were established using the data processing software by means of peak area ratios (peak area of free lyso-phingomyelin and compound 509, respectively, contained in the sample from the subject/peak area of Internal Standard). Free lyso-sphingomyelin and compound 509 concentrations were evaluated using an Internal Standard methodA quadratic ($y=ax^2+bx+c$) regression model using the weighting factor 1/conc. will be used to calculate the concentration of each analyte in every batch to be evaluated. The concentrations were calculated by means of the following formula:

$$\text{concentration} = \frac{-b \pm \sqrt{b^2 - 4a(c - \text{peak area ratio})}}{2a}$$

Based thereon mean values, precision results (in terms of CVs) and accuracies (formula shown below) will be calculated using the program "Lotus 123".

$$\text{accuracy (\%)} = \frac{\text{calculated concentration}}{\text{expected concentration}} \cdot 100$$

Appropriate statistical models are described in e.g.

Green, J. R., Statistical Treatment of Experimental Data (Elsevier, New York, 1977), page 210 ff Lothar Sachs, Angewandte Statistik—Anwendung statistischer Methoden (Springer, Berlin, Heidelberg, N.Y., Tokyo 1984)

A person skilled in the art will acknowledge that according to a substance, the molecular structure of which is not known, a reference item is not synthesized. The evaluation of such substance is thus based on the peak area ratio to the Internal Standard added to each sample and comparison between patients and healthy persons, respectively.

Software

Data acquisition, data processing, statistics and calculations were performed using Analyst® software 1.4.2 or higher (AB SCIEX, USA/Canada) as well as Lotus 1-2-3 97 or higher (Lotus Corp, USA).

| | Handbooks |
|---|---|
| Handbook | Arbeiten mit SmartSuite 97 (Lotus Development Corp., 1997) |
| Documentation of software used | Documentation of Analyst ® Software (AB SCIEX, USA/Canada): Operator's Manual & Operator's Manual Addendum "New Functionality in Analyst 1.2" and Online Help System Analyst 1.4 (or higher) |

Example 2: Genetic Testing and Classification of Study Participants

After consenting of patients to participation in the study, patients were subjected to a genetic testing for mutations of the genes SMPD1, NPC1 and NPC2. Accordingly, 5 to 10 ml of EDTA blood were sequenced according to Seeman et al. (Seeman et al., 1995). Were appropriate other genes beside the genes SMPD1, NPC1 and NPC2 were sequenced in addition, particularly in controls. Said genetic testing was controlled using test samples of age and sex matched control patients.

448 plasma samples from 304 subjects were analyzed. More precisely, for 274 patients one plasma sample, for 14 patients two plasma samples, and for 16 patients more than two plasma samples were available.

According to the result of the above described genetic testing, patients participating in the study were classified into the following groups:

1.) Patients having Niemann-Pick disease type A or B: gold standard for the diagnosis was the detection of two pathogenic mutations within the SMPD1 gene, either homozygous or compound heterozygous (group is named in the figures as "Niemann-Pick type A/B").

2.) Patients having Niemann-Pick disease type C: gold standard for the diagnosis was the detection of pathogenic mutations within the NPC1 or NPC2 gene, either homozygous or compound heterozygous (group is named in the figures as "Niemann-Pick type C").

3.) Patients being heterozygous carriers of one mutation within the NPC1 or NPC2 gene (typically relatives of affected patients) (group is named in the figures as "Niemann-Pick type C carrier").

4.) Patients with other lysosomal storage disorders as control (group is named in the figures as "other LSD"); this comprises patients with Krabbe disease among others. Patients being positively tested for Gaucher's disease were grouped separately; all diagnoses have been proven by the detection of two pathogenic mutations.

5.) Healthy age and gender matched controls (group is named in the figures as "control").

The distribution of the gender of the 304 patients is depicted in Table 1b.

TABLE 1B

| 304 subjects classified by gender | | |
|---|---|---|
| | All N (individuals) | % |
| total | 304 | |
| Sex | | |
| male | 141 | 46.7 |
| female | 161 | 53.3 |
| missing | 2 | — |

The following table 1C shows the distribution of the age of the 304 patients and the classification of said patients based on the results of the above described genetic testing as well as the gender of said patients.

TABLE 1c

| Patient characteristics of 304 subjects | | | |
|---|---|---|---|
| | NP A/B | NP C | NP C carrier |
| N individuals | 18 | 36 | 16 |
| % | 5.9 | 11.8 | 5.3 |
| N measures | 19 | 63 | 26 |
| Age in years (median, interquartile range) (number of cases) | 2.0 (1.0-14) (n = 11) | 17.0 (7.8-25.0) (n = 34) | 47.5 (35.5-53.3) (n = 14) |

| | m(ale) | f(emale) | m | f | m | f |
|---|---|---|---|---|---|---|
| n | 9 | 9 | 17 | 19 | 8 | 8 |
| % in this subgroup | 50.0 | 50.0 | 47.2 | 50.0 | 50.0 | 50.0 |
| Age (median, interquartile range) | 1.0 (0-11) | 10.5 (2.5-47.0) | 14.0 (5.5-25.5) | 19.0 (10.0-24.0) | 47.5 (31.5-54.0) | 47.0 (38.0-52.8) |

TABLE 1c-continued

Patient characteristics of 304 subjects

|  | Gaucher | other LSDs | healthy controls |
|---|---|---|---|
| N individuals | 14 | 114 | 106 |
| % | 4.6 | 37.5 | 34.9 |
| N measures | 78 | 151 | 111 |
| Age in years (median, interquartile range) (number of cases) | 44.0 (27.5-58.0) (n = 13) | 34.0 (14.0-49.0) (n = 91) | 47.0 (36.0-54.0) (n = 98) |

|  | m | f | m | f | m | f |
|---|---|---|---|---|---|---|
| n | 10 | 4 | 59 | 53 | 38 | 68 |
| % in this subgroup | 71.4 | 28.6 | 52.7 | 47.3 | 35.8 | 64.2 |
| Age (median, interquartile range) | 44.0 (27.5-55.5) | 48.5 (20.8-60.5) | 24.0 (10.0-49.0) | 44.0 (26.0-50.0) | 47.5 (39.3-53.0) | 46.5 (35.0-56.0) |

The level of free lyso-sphingomyelin and/or compound 509 in samples of said 304 subjects was determined according to the method described in Example 1. Table 1d shows the mean and median levels of free lyso-sphingomyelin and of compound 509 as well as the ratio of the level of compound 509 to the level of free lyso-sphingomyelin in said samples of said 304 subjects.

TABLE 1D

Median (and interquartile range) values in different groups

|  | n | 465 | 509 | 509/465 |
|---|---|---|---|---|
| NP A/B | 18 | 494.0 (274.6-634.8) | 30.94 (17.78-41.84) | 0.07 (0.06-0.10) |
| NP C | 36 | 18.0 (12.5-24.7) | 4.14 (2.67-5.58) | 0.24 (0.13-0.32) |
| NP C carrier | 16 | 9.4 (6.7-12.6) | 0.16 (0.07-0.66) | 0.03 (0.01-0.07) |
| Gaucher | 14 | 3.0 (0.5-9.7) | 0.09 (0.05-0.17) (n = 13) | 0.01 (0.01-0.10) (n = 13) |
| other LSDs | 114 | 5.3 (0.5-7.6) | 0.04 (0.02-0.07) | 0.01 (0.005-0.02) |
| control | 106 | 4.7 (2.4-6.4) | 0.04 (0.02-0.06) | 0.01 (0.005-0.02) |

The level of free lyso-sphingomyelin in samples from said patients depending on the classification by genetic analysis is shown in FIG. 1.

FIG. 1 is a boxplot indicating levels of free lyso-sphingomyelin, i.e. compound 465. The y-axis demonstrates the logarithmised levels of free lyso-sphingomyelin in ng/ml determined in plasma of patients by the method according to the present invention, wherein the x-axis depicts groups of patients (dgn), which have been grouped as described in Example 2. The boxplot represents the $25^{th}$ and $75^{th}$ percentile of each group of patients by the bottom and top of the box, respectively; the band near the middle of the box represents the $50^{th}$ percentile (i.e. the median) of each group; The whiskers represent one standard deviation above and below the mean of the data; Any data not included between the whiskers is shown as an outlier with a small circle or star.

The processed cases were as follows:

| group of patients | valid N |
|---|---|
| 1.00 NP A/B | 18 |
| 2.00 NP C | 36 |

-continued

| group of patients | valid N |
|---|---|
| 3.00 NP C carrier | 16 |
| 4.00 Gaucher | 14 |
| 5.00 other LSDs | 114 |
| 6.00 healthy controls | 106 |

Figure 2:
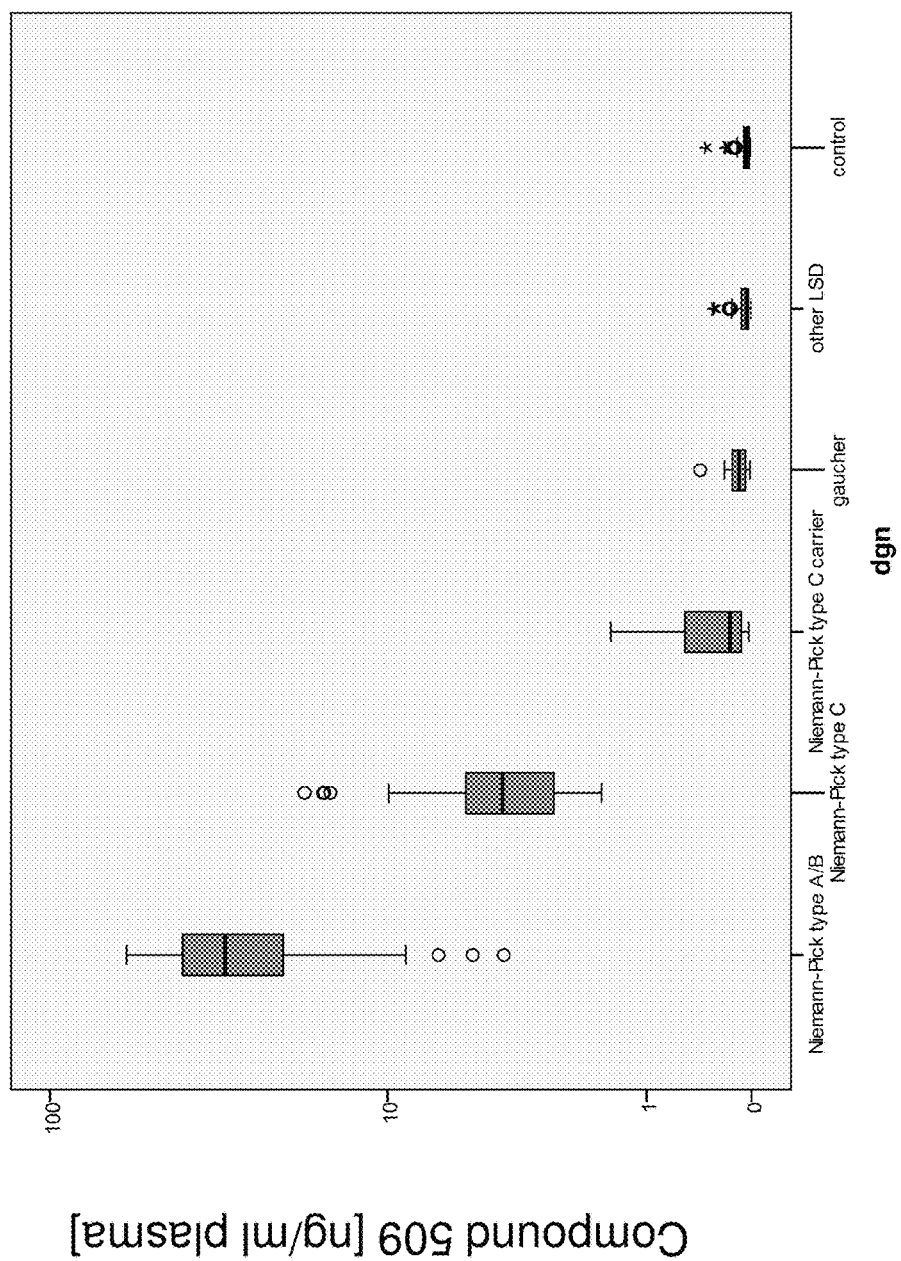
FIG. 2 is a boxplot indicating levels of compound 509 in ng/ml plasma.

The level of compound 509 in samples from said patients depending on the classification by genetic analysis is shown in FIG. 2.

FIG. 2 is a boxplot indicating levels of compound 509; the y-axis demonstrates the logarithmised levels of compound 509 in ng/ml determined in plasma of patients by the method according to the present invention, wherein the x-axis depicts groups of patients (dgn), which have been grouped as described in Example 2. The boxplot represents the $25^{th}$ and $75^{th}$ percentile of each group of patients by the bottom and top of the box, respectively; the band near the middle of the box represents the 50$^{th}$ percentile (i.e. the median) of each group; The whiskers represent one standard deviation above and below the mean of the data; Any data not included between the whiskers is shown as an outlier with a small circle or star.

The processed cases were as follows

| dgn | cases valid N |
|---|---|
| 1.00 NP A/B | 18 |
| 2.00 NP C | 36 |
| 3.00 NP C carrier | 16 |
| 4.00 Gaucher | 13 |
| 5.00 other LSDs | 114 |
| 6.00 healthy controls | 106 |

Figure 3:
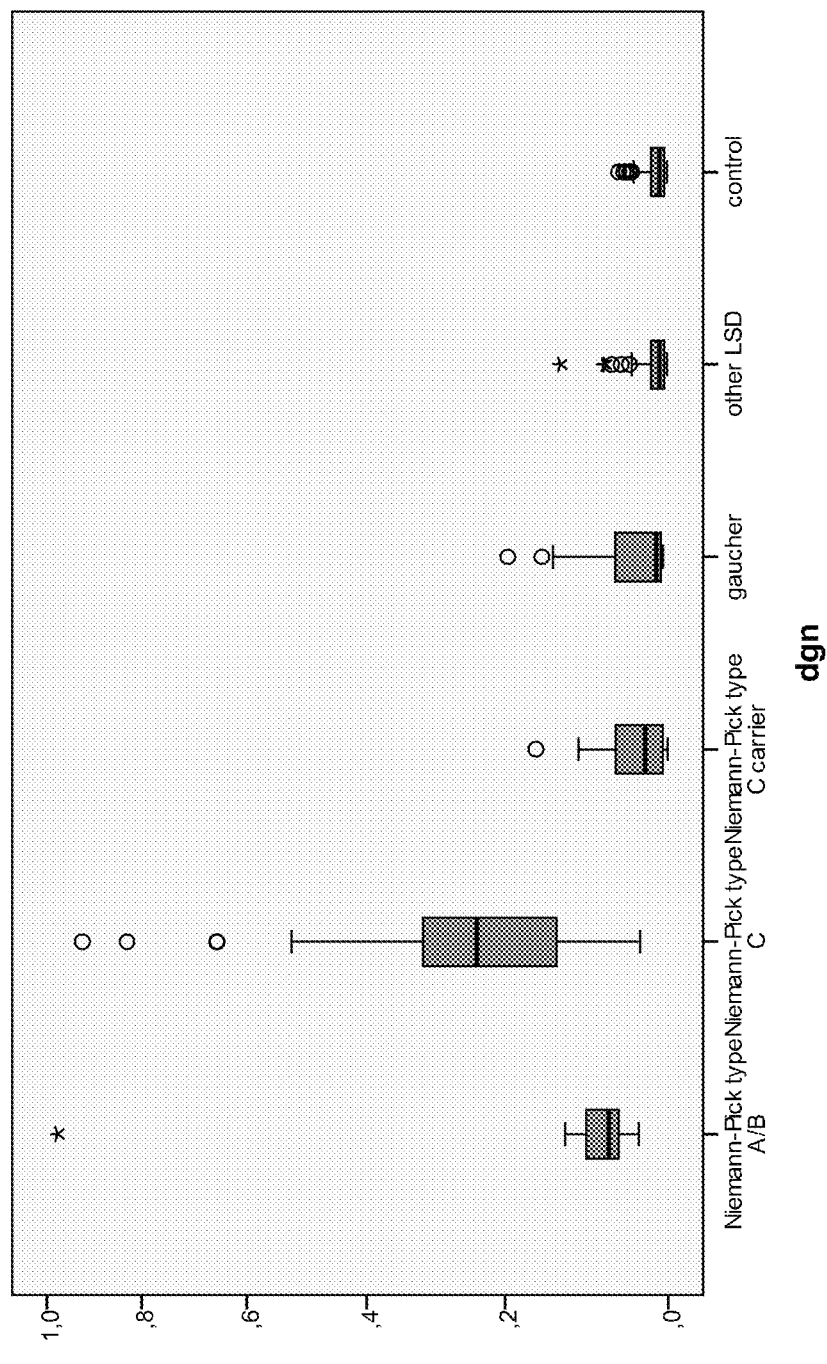
FIG. 3 is a boxplot indicating the ratio of levels of compound 509 to levels of compound 465.

The ration of the level of compound 509 and the level of free lyso-sphingomyelin in samples from said patients depending on the classification by genetic analysis is shown in FIG. 3.

FIG. 3 is a boxplot indicating on the y-axis the ratio of the level of compound 509 to the level of compound 465 both determined in plasma of patients by the method according to the present invention, wherein the x-axis depicts groups of patients (dgn), which have been grouped as described in Example 2. The boxplot represents the 25$^{th}$ and 75$^{th}$ percentile of each group of patients by the bottom and top of the box, respectively; the band near the middle of the box represents the 50$^{th}$ percentile (i.e. the median) of each group; The whiskers represent one standard deviation above and below the mean of the data; Any data not included between the whiskers is shown as an outlier with a small circle or star.

The processed cases were as follows:

| dgn | cases valid N |
|---|---|
| 1.00 NP A/B | 18 |
| 2.00 NP C | 36 |
| 3.00 NP C carrier | 16 |
| 4.00 Gaucher | 13 |
| 5.00 other LSDs | 114 |
| 6.00 healthy controls | 106 |

The type of mutation and the distribution of the types of mutations of the NPC1 gene in patients classified as Niemann-Pick disease type C patients according to the results obtained in the genetic testing as described above are depicted in Table 2A below.

TABLE 2A

Distribution of mutations being detected in Niemann-Pick disease type C patients 48 of 72 measures are valid/36 individuals (two measures per individual)

| cDNA | n | % of valid measures |
|---|---|---|
| c.2861C > T | 5 | 10.4% |
| c.3019C > G | 4 | 8.3% |
| c.3104C > T | 3 | 6.3% |
| c.1166G > T | 2 | 4.2% |
| c.1990G > A | 2 | 4.2% |
| c.2196dupT | 2 | 4.2% |
| c.3245G > A | 2 | 4.2% |

TABLE 2A-continued

Distribution of mutations being detected in Niemann-Pick disease type C patients 48 of 72 measures are valid/36 individuals (two measures per individual)

| cDNA | n | % of valid measures |
|---|---|---|
| c.3478-6T > A | 2 | 4.2% |
| c.3493G > A | 2 | 4.2% |
| c.1112delT | 1 | 2.1% |
| c.1114C > T | 1 | 2.1% |
| c.1202C > T | 1 | 2.1% |
| c.1501G > T | 1 | 2.1% |
| c.1535A > G | 1 | 2.1% |
| c.2621A > T | 1 | 2.1% |
| c.2660C > T | 1 | 2.1% |
| c.2684dupG | 1 | 2.1% |
| c.2727G > A | 1 | 2.1% |
| c.2795 + 1G > C | 1 | 2.1% |
| c.289T > A | 1 | 2.1% |
| c.3001A > G | 1 | 2.1% |
| c.58-3T > G | 1 | 2.1% |
| c.616_619delACTC | 1 | 2.1% |
| c.749_755delAGCCCCA | 1 | 2.1% |
| c.1143G > C | 1 | 2.1% |
| c.1554-1900G > A | 1 | 2.1% |
| c.2292G > A | 1 | 2.1% |
| c.2668T > C | 1 | 2.1% |
| c.2872C > T | 1 | 2.1% |
| c.3100G > A | 1 | 2.1% |
| c.3433T > C | 1 | 2.1% |
| c.3618delA | 1 | 2.1% |
| c.3662delT | 1 | 2.1% |

The type of mutation and the distribution of the types of mutations of the SMPD1 gene in patients classified as Niemann-Pick disease type A/B patients according to the results obtained in the genetic testing as described above are depicted in Table 2B below.

TABLE 2B

Distribution of mutations being detected in Niemann-Pick disease type A/B patients 34 of 36 measures are valid/18 individuals (two measures per individual

| cDNA | n | % of valid measures |
|---|---|---|
| c.1556A > G | 5 | 14.71% |
| c.416T > C | 4 | 11.76% |
| c.573delT | 4 | 11.76% |
| c.1267C > T | 2 | 5.88% |
| c.1493G > A | 2 | 5.88% |
| c.1502A > C | 2 | 5.88% |
| c.1624C > T | 2 | 5.88% |
| c.1718G > C | 2 | 5.88% |
| c.488T > C | 2 | 5.88% |
| c.502G > A | 2 | 5.88% |
| c.742G > A | 2 | 5.88% |
| c.776T > G | 2 | 5.88% |
| c.1390G > T | 1 | 2.94% |
| c.533T > A | 1 | 2.94% |
| c.1785-1786delTT | 1 | 2.94% |

Example 3: Diagnosis of Niemann-Pick Disease Using Free Lyso-Sphingomyelin and/or Compound 509 as a Biomarker The protocols described in Example 1 above were used to generate HPLC-mass spectrometric chromatograms of 448 plasma samples derived from the 304 subjects. Exemplary HPLC-mass spectrometric chromatograms displaying peak intensity of free lyso-sphingomyelin and IS of four Niemann-Pick disease type C patients and one healthy control person are depicted in FIG. 8A, FIG. 8B, FIG. 8C, FIG. 8D and FIG. 8E.

More particularly, FIG. 8A shows HPLC-mass spectrometic chromatograms displaying peak intensity in cps of free lyso-sphingomyelin (upper panel), compound 509 (middle panel) and IS (lower panel) of a sample from a healthy subject as a function over the retention time in minutes. FIG. 8B, FIG. 8C, FIG. 8D and FIG. 8E show HPLC-mass spectrometic chromatograms displaying peak intensity in cps of free lyso-sphingomyelin (upper panel), compound 509 (middle panel) and IS (lower panel) of a sample from a healthy subject as a function over the retention time in minutes. The retention time of a substance as used herein, preferably is depicted on the x-axis and is the elapsed time between the time of injection of a solute, e.g. a biomarker according to the present invention and/or an internal standard, and the time of elution of the peak maximum of said solute. A person skilled in the art will acknowledge that the retention time of a substance according to the herein described methods is a unique characteristic of said solute and can be used for identification purposes. Internal Standard working solution comprising Lyso-Gb2 as an internal standard was added to the sample as described in Example 1. It is important to understand that by said addition of IS to the sample, i.e. spiking of the sample, to be subjected to the method according to the present invention, the concentration of IS in the sample is known and by determining the area under the peak, i.e. the peak area, of the internal standard in said HPLC-mass spectrometric chromatogram the relation between a peak area and a concentration of a substance, e.g. of IS and/or a biomarker thus can be calculated. More precisely, a person skilled in the art will acknowledge that a peak area of a substance depicted in an HPLC-mass spectrometric chromatogram, such as the HPLC-mass spectrometric chromatogram depicted in FIG. 8A, FIG. 8B, FIG. 8C, FIG. 8D or FIG. 8E, represents a measure for an amount of said substance subjected to an HPLC-mass spectrometric analysis. Moreover, a person skilled in the art will be able to calculate the amount of the substance in a sample from a subject subjected to an HPLC-mass spectrometric analysis, e.g. the amount of free lyso-sphingomyelin in a sample subjected to the method of the present invention, using a ratio of the peak area of free lyso-sphingomyelin, the amount of which is to be determined by said method and the peak area of IS, e.g. free lyso-Gb2; as well as calibration curves generated with said method and said free lyso-sphingomyelin and/or IS. Accordingly, this allows subsequently for determining a level of free lyso-sphingomyelin.

With regard to compound 465<lloq has been replaced by 0.02, which refers to half of the limit of detection For comparing the diagnostic value of the different biomarkers and for the calculation of correlations between the biomarkers we first aggregated the data by using the first measured value of every marker for every patient.

Paired sample statistical techniques were used for the comparison of two biomarkers. The method exploits the mathematical equivalence of the AUC to the Mann-Whitney U-statistic (Delong E. R., Delong D. M., Clarke-Pearson D. L., 1988, *Biometrics*, 44, 837-45.).

The accuracy of levels of the different biomarkers (free lyso-sphingomyelin, compound 509) obtained by the method described in Example 1 above, as well as the accuracy of the ratio of the two biomarkers according to the present invention, was evaluated to discriminate patients with Niemann-Pick disease from patients without having Niemann-Pick disease, as well as to discriminate patients with Niemann-Pick disease type C from patients with Niemann-Pick disease type A/B, using Receiver Operating Characteristic (ROC) curve analysis (Metz C. E., 1978, *Semin Nucl Med*, 8, 283-98; Zweig M. H., Campbell G., 1993, *Clin Chem*, 39, 561-77).

The ROC curves were calculated using PASW Statistics 18, Release Version 18.0.2 (© SPSS, Inc., 2009, Chicago, Ill., www.spss.com). The comparisons of ROC curves and the linear mixed models were done using SAS software, Version 9.2 of the SAS System for Windows. (© 2008 SAS Institute Inc., Cary, N.C., USA).

Figure 5A:
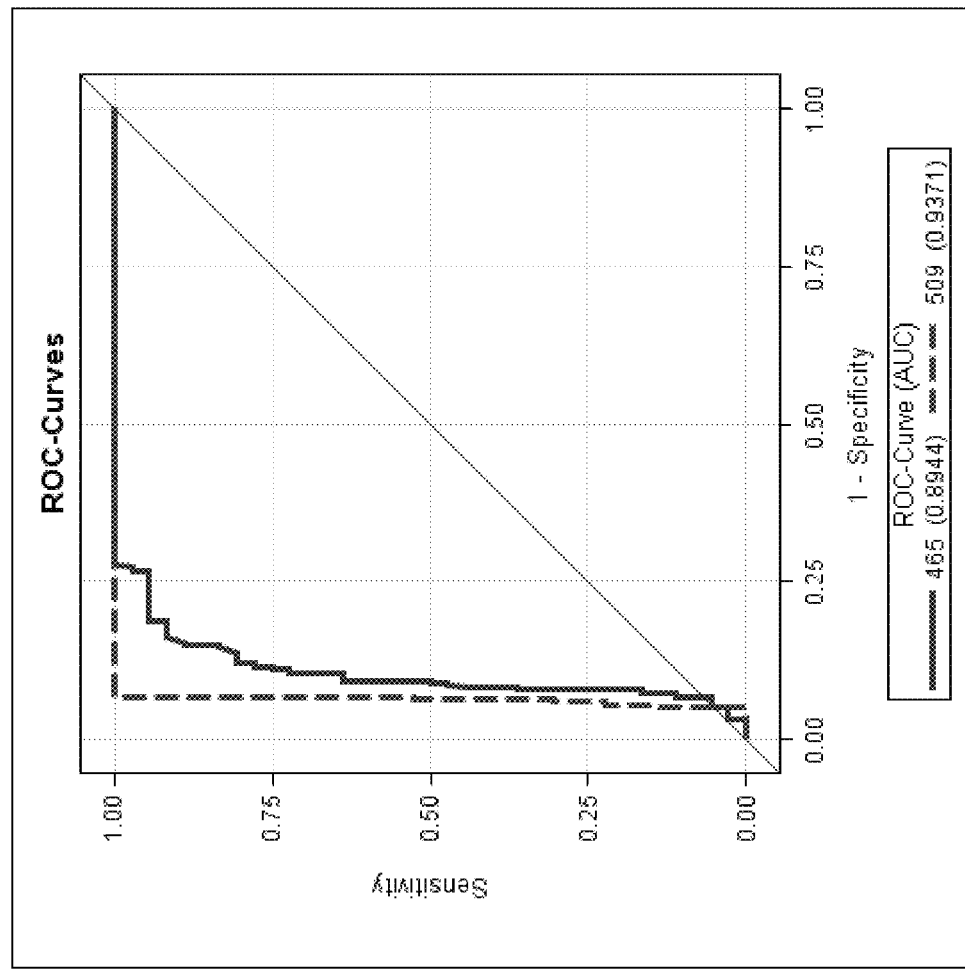
FIGS. 5A, 5B and 5C are graphs showing receiver operating characteristics (ROC) curves for the diagnosis of NP type C.
Figure 5B:
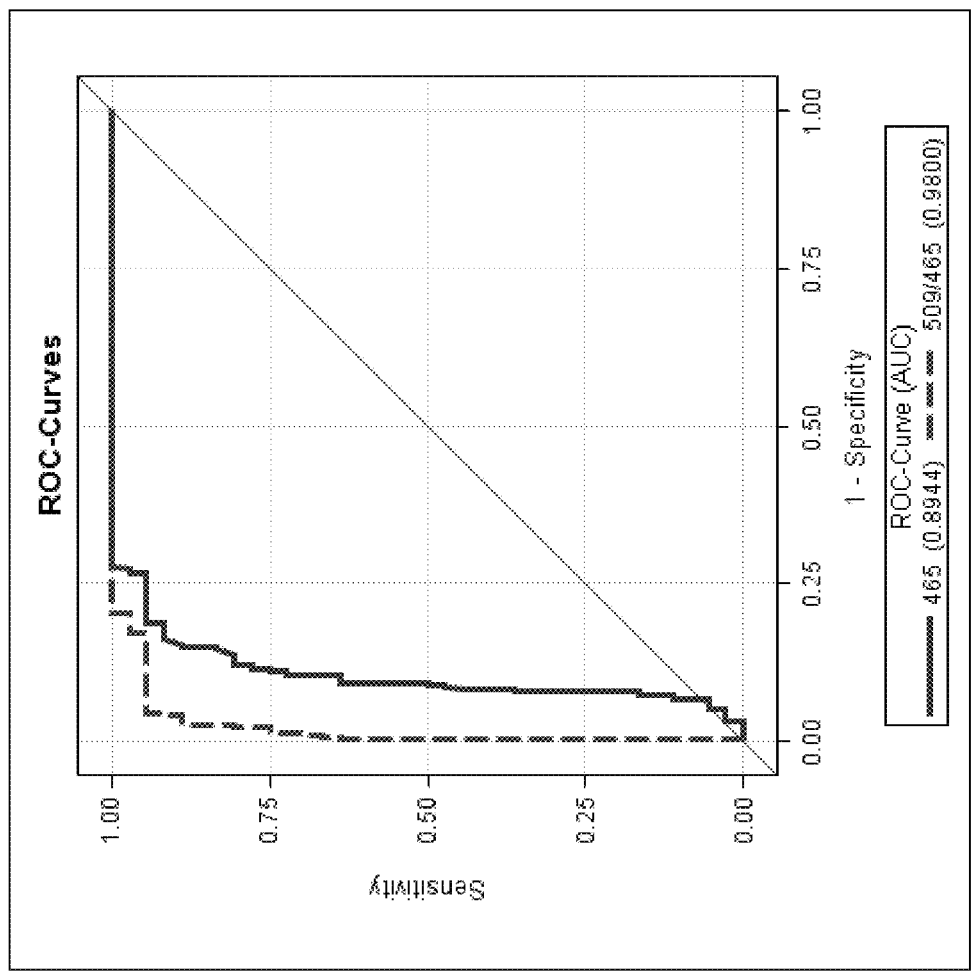
Figure 5C:
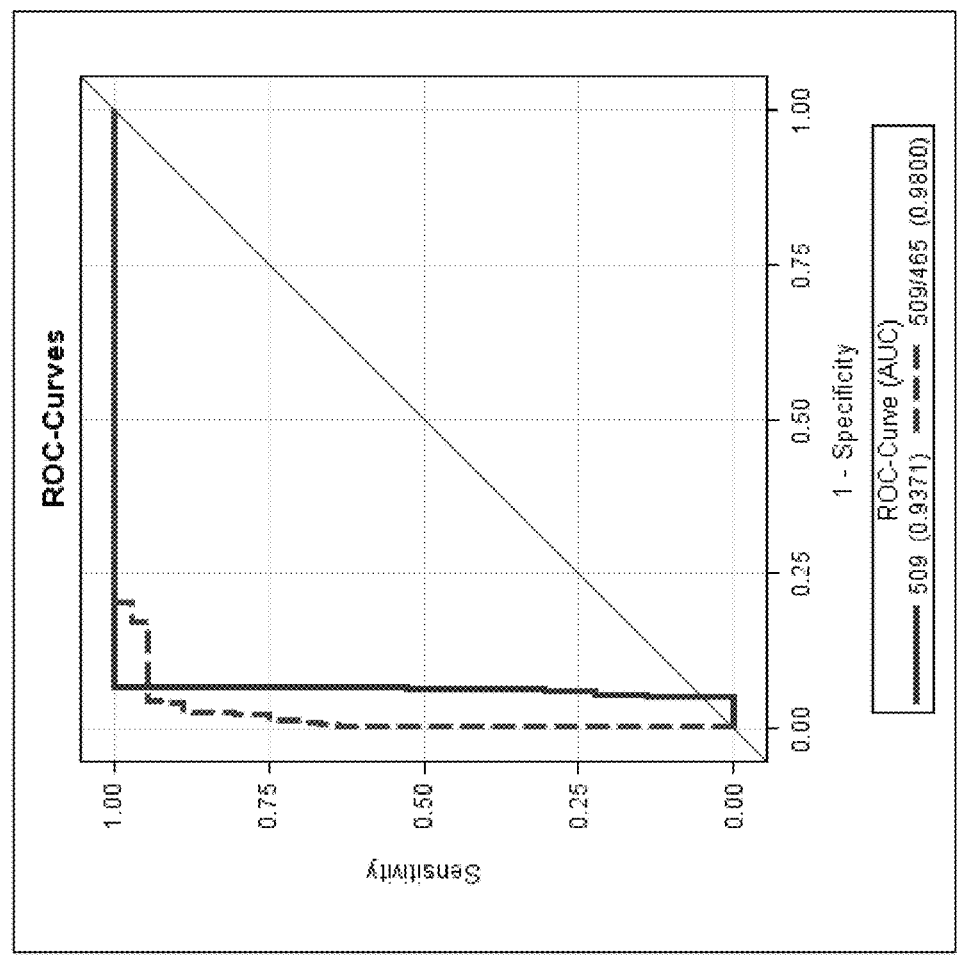
Figure 6:
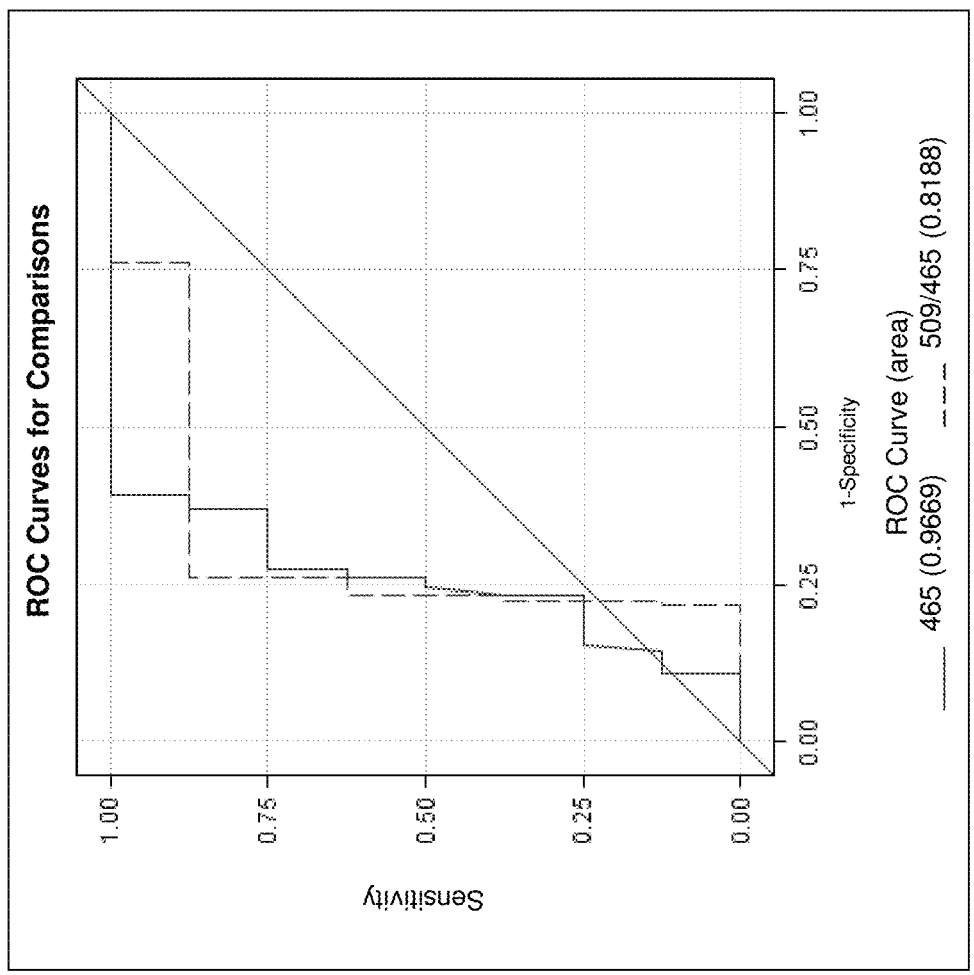
FIG. 6 is a graph showing receiver operating characteristics (ROC) curves of compound 465 and of compound 509 for the diagnosis of NP type C carrier.

The results depicted in the ROC-curves shown in FIG. 4, FIG. 5 and FIG. 6 also show the specificity and the sensitivity of the method according to the present invention depending on different cut-off values of free lyso-sphingomyelin. The area under the curve (AUC) and the 95% confidence limits for the free lyso-sphingomyelin are reported in table 3.

Figure 4A:
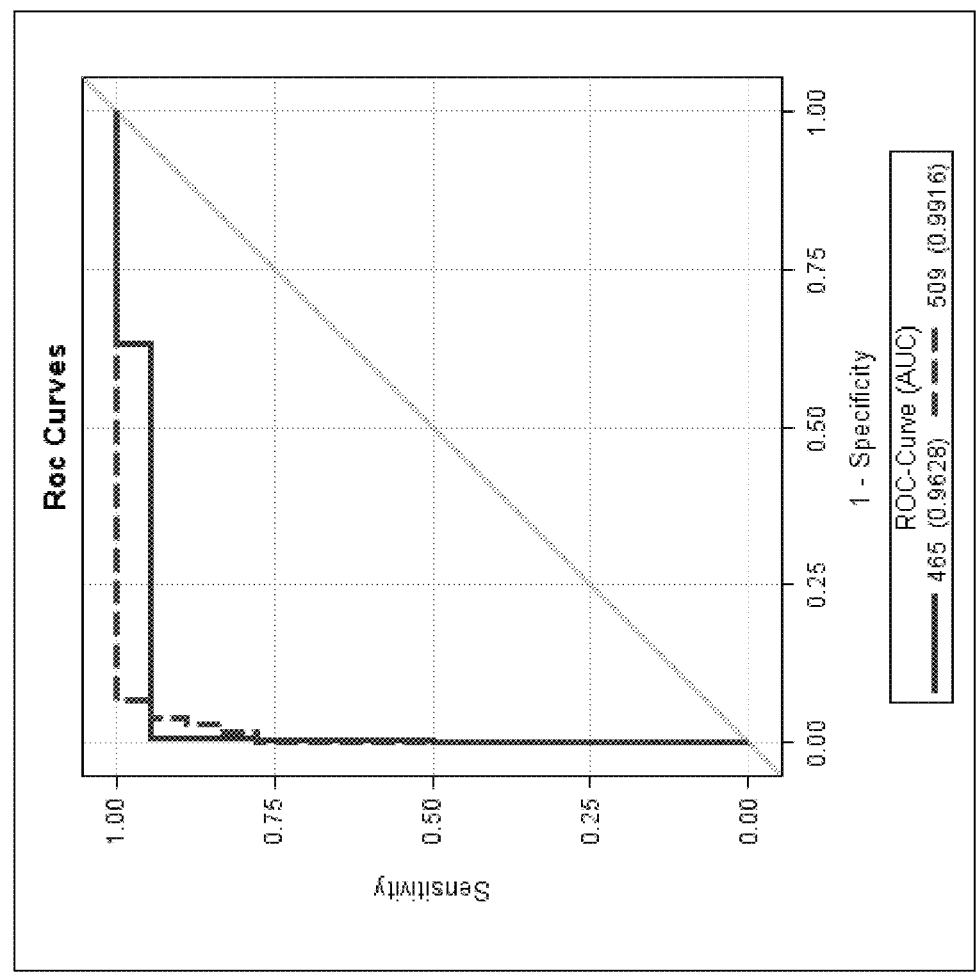
FIGS. 4A, 4B and 4C are graphs showing receiver operating characteristics (ROC) for the diagnosis of NP type A and B.
Figure 4B:
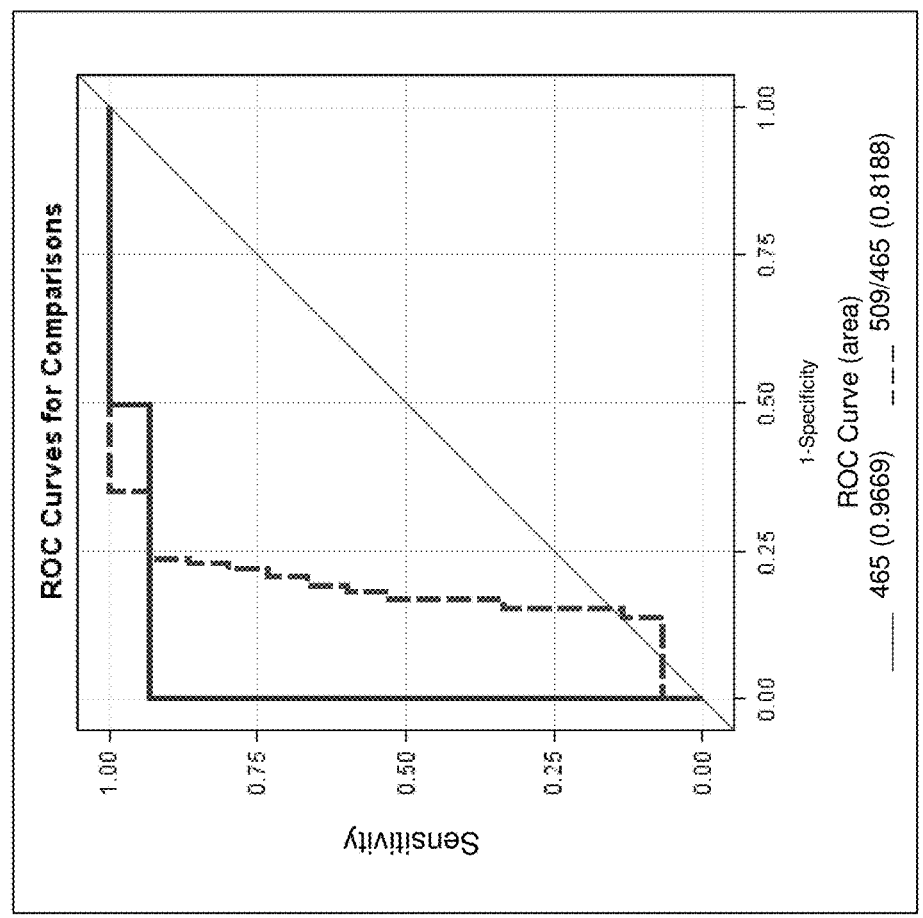
Figure 4C:
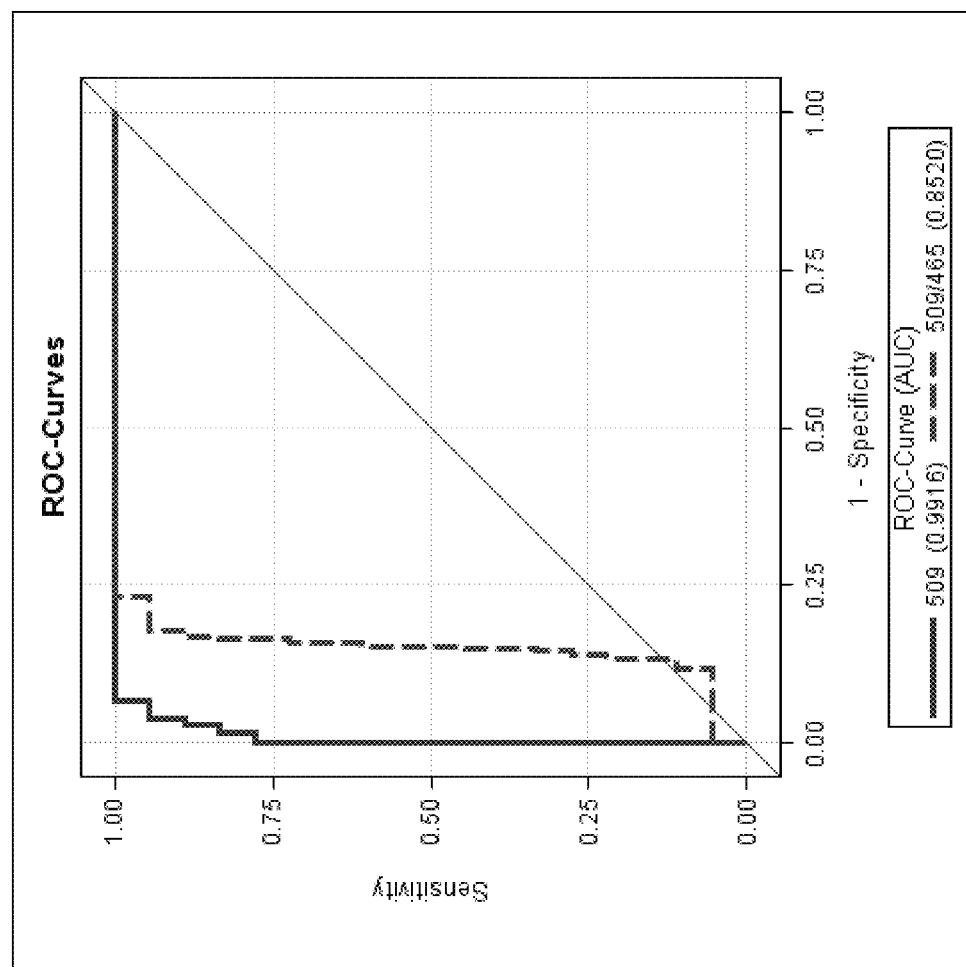

FIGS. 4A to C are graphs showing receiver operating characteristics (ROC) curves for the diagnosis of NP type A and B; The x-axis represents "1-specificity" and the y-axis represents the sensitivity.

FIG. 4A shows ROC-curves of compound 465 and compound 509 for the diagnosis of NP type A and B wherein the test for differences between ROC curves resulted in a p-value of 0.363. The ROC-curve for compound 465 depicted by the solid line is reflecting an AUC of 0.9628, whereas the ROC-curve for compound 509 depicted by the dashed line is reflecting an AUC of 0.9916. The graph is based on the diagnosis of 303 patients in total, wherein 18 thereof were positively tested for having NP Typ A/B by Genetic testing as described in Example 2 herein.

FIG. 4B shows ROC-curves of compound 465 and the ratio of level of compound 509 to level of compound 465 for the diagnosis of NP type A and B, wherein the test for differences between ROC curves resulted in a p-value of 0.0083. The ROC-curve for compound 465 depicted by the solid line is reflecting an AUC of 0.9669, whereas the ROC-curve for compound 509 depicted by the dashed line is reflecting an AUC of 0.9903. The graph is based on the diagnosis of 146 patients in total, wherein 15 thereof were positively tested for having NP Typ A/B by Genetic testing as described in Example 2 herein.

FIG. 4C shows ROC-curves of compound 509 and the ratio of level of compound 509 to level of compound 465 for the diagnosis of NP type A and B of 303 samples, wherein 18 are positive for NPC Type A/B and wherein the Wald Test for differences between ROC curves resulted in a p-value of p<0.0001. The ROC-curve for compound 509 depicted by the solid line is reflecting an AUC of 0.9916, whereas the ROC-curve for the ratio of leves of compound 509 to level of compound 465 depicted by the dashed line is reflecting an AUC of 0.8520. The graph is based on the diagnosis of 303 patients in total, wherein 18 thereof were positively tested for having NP Typ A/B by Genetic testing as described in Example 2 herein.

FIGS. 5A to C are graphs showing receiver operating characteristics (ROC) curves for the diagnosis of NP type C; The x-axis represents "1-specificity" and the y-axis represents the sensitivity.

FIG. 5A shows ROC-curves of compound 465 and compound 509 for the diagnosis of NP type C, wherein the test for differences between ROC curves resulted in a p-value of 0.0003. The ROC-curve for compound 465 depicted by the solid line is reflecting an AUC of 0.8944, whereas the ROC-curve for compound 509 depicted by the dashed line is reflecting an AUC of 0.9371. The graph is based on the diagnosis of 303 patients in total, wherein 36 thereof were positively tested for having NP type C by Genetic testing as described in Example 2 herein.

FIG. 5B shows ROC-curves of compound 465 and the ratio of level of compound 509 to level of compound 465 for the diagnosis of NP type C, wherein the test for differences between ROC curves resulted in a p-value of 0.0001. The ROC-curve for compound 465 depicted by the solid line is reflecting an AUC of 0.8685, whereas the ROC-curve for the ratio of level of compound 509 to level of compound 465 depicted by the dashed line is reflecting an AUC of 0.9654. The graph is based on the diagnosis of 303 patients in total, wherein 36 thereof were positively tested for having NP type C by Genetic testing as described in Example 2 herein.

FIG. 5C shows ROC-curves of compound 509 and the ratio of level of compound 509 to level of compound 465 for the diagnosis of NP type C, wherein the test for differences between ROC curves resulted in a p-value of 0.0065. The ROC-curve for compound 509 depicted by the solid line is reflecting an AUC of 0.9371, whereas the ROC-curve for the ratio of level of compound 509 to level of compound 465 depicted by the dashed line is reflecting an AUC of 0.9800. The graphs are based on the diagnosis of 303 patients in total, wherein 36 thereof were positively tested for having NP type C by Genetic testing as described in Example 2 herein.

FIG. 6 is a graph showing receiver operating characteristics (ROC) curves of compound 465 and of compound 509 for the diagnosis of NP type C carrier; the graph is based on the diagnosis of 146 patients in total, wherein/thereof were positively tested for being NP type C carriers by Genetic testing as described in Example 2 herein. The x-axis represents "1-specificity" and the y-axis represents the sensitivity. The test for differences between ROC curves resulted in a p-value of 0.5991. The ROC-curve for compound 465 depicted by the solid line is reflecting an AUC of 0.7468, whereas the ROC-curve for compound 509 depicted by the dashed line is reflecting an AUC of 0.6984.

TABLE 3

Sensitivity and specificity for different biomarkers with regard to NPC

|  | 465 | 509 | 509/465 |
| --- | --- | --- | --- |
| NP A/B (n) | 18 of 304 | 18 of 303 | 18 of 303 |
| Cut point | >59 | >5 | >0.045 |
| Sensitivity | 94.4% | 94.4% | 94.4% |
| Specificity | 99.3% | 96.1% | 82.1% |
| AUC and 95% CI in ROC Analysis | 0.96 (0.90-1.00) | 0.99 (0.98-1.00) | 0.85 (0.81-0.90) |
| NP C | 36 of 304 | 36 of 303 | 36 of 303 |
| Cut point | >9.23 | >1.7 | >0.087 |
| Sensitivity | 94.4% | 97.2% | 94.4% |
| Specificity | 81.3% | 93.3% | 95.5% |
| AUC and 95% CI in ROC Analysis | 0.90 (0.86-0.93) | 0.94 (0.91-0.97) | 0.98 (0.96-1.00) |

Table 4 below shows accordingly the sensitivity and the specificity of the method according to the present invention depending on different cut-off values of free lyso-sphingomyelin.

Comparing the level of the biomarker in a sample from a subject determined by the method according to the present invention to a cut-off value, preferably a cut-off value allowing for a diagnosis having high specificity and high sensitivity thus allows for diagnosing Niemann-Pick disease in said subject, wherein an elevated level of the biomarker in the sample from the subject compared to the cut-off value is indicative for the subject for suffering from or for being at risk for developing Niemann-Pick disease and wherein a lower level of the biomarker in the sample from the subject compared to the cut-off value is indicative for the subject for not suffering from or for not being at risk for developing Niemann-Pick disease.

Comparing the ratio of the levels of two biomarker in a sample from a subject determined by the method according to the present invention to a cut-off value, preferably a cut-off value allowing for a diagnosis having high specificity and high sensitivity thus allows for diagnosing Niemann-Pick disease in said subject, wherein an elevated the ratio of the levels of two biomarker in the sample from the subject compared to the cut-off value is indicative for the subject for suffering from or for being at risk for developing Niemann-Pick disease and wherein a lower the ratio of the levels of two biomarker in the sample from the subject compared to the cut-off value is indicative for the subject for not suffering from or for not being at risk for developing Niemann-Pick disease.

Accordingly, in table 3 the sensitivity and the specificity of free lyso-sphingomyelin as a biomarker used in a method for diagnosing Niemann-Pick disease, and more particularly different types of Niemann-Pick disease in a sample from a subject is compared using different cut-off values. Free lyso-sphingomyelin was determined according to the method of the present invention. The ideal cut-off value for the respective biomarkers and disease may be taken from table 3 above.

A person skilled in the art will acknowledge that the method according to the present invention using free lyso-sphingomyelin and/or compound 509 as a biomarker, and/or the ratio of the level of compound 509 to the level of free lyso-sphingomyelin, for diagnosing Niemann-Pick disease is clearly advantageous over methods of the prior art.

Accordingly, levels of compound 509 determined in a sample from a subject according to the method of the instant application higher than 5 ng/ml allow for diagnosing that the subject is suffering from or is at risk for developing NP type A and B with a sensitivity of 94.4% and a specificity of 96.1%.

Levels of compound 509 determined in a sample from a subject according to the method of the instant application higher than 1.7 ng/ml allow for diagnosing that the subject is suffering from or is at risk for developing NP type C with a Sensitivity of 97.2% and a specificity of 93.3%.

Levels of compound 509 determined in a sample from a subject according to the method of the instant application higher than 0.031 ng/ml allow for diagnosing that the subject is suffering from or is at risk for developing NP type C carrier with a sensitivity of 100% and a specificity of 22.5%.

Levels of free lyso-sphingomyelin determined in a sample from a subject according to the method of the instant application higher than 59 ng/ml allow for diagnosing that the subject is suffering from or is at risk for developing NP type A and B with a sensitivity of 94.4% and a specificity of 99.3%.

Levels of free lyso-sphingomyelin determined in a sample from a subject according to the method of the instant application higher than 9.23 ng/ml allow for diagnosing that the subject is suffering from or is at risk for developing NP type C with a sensitivity of 94.4% and a specificity of 81.3%.

Levels of free lyso-sphingomyelin determined in a sample from a subject according to the method of the instant application higher than 6.5 ng/ml allow for diagnosing that the subject is suffering from or is at risk for developing NP type C carrier with a sensitivity of 100% and a specificity of 61.2%.

The ratio of the level of compound 509 to the level of free lyso-sphingomyelin determined in a sample from a subject according to the method of the instant application higher than 0.045 allow for diagnosing that the subject is suffering from or is at risk for developing NP type A and B with a Sensitivity of 94.4% and a specificity of 82.1%.

The ratio of the level of compound 509 to the level of free lyso-sphingomyelin determined in a sample from a subject according to the method of the instant application higher than 0.087 allow for diagnosing that the subject is suffering from or is at risk for developing NP type C with a sensitivity of 94.4% and a specificity of 95.5%.

Example 4: Analysis of Change of Biomarkers Over Time

The method and patients used in connection with this Example were those as described in Examples 1 to 3.

For analyzing how the level of biomarkers, such as compound 509, changed over time in patients having Niemann-Pick disease non aggregated data was analyzed for those patients for whom more than one plasma sample was analyzed, namely six NPC type C patients and one NPC type C carrier. A time point zero was set to the first measure under therapy for every patient. Linear mixed models were used for testing if time dependent reduction occurred.

Figure 7:
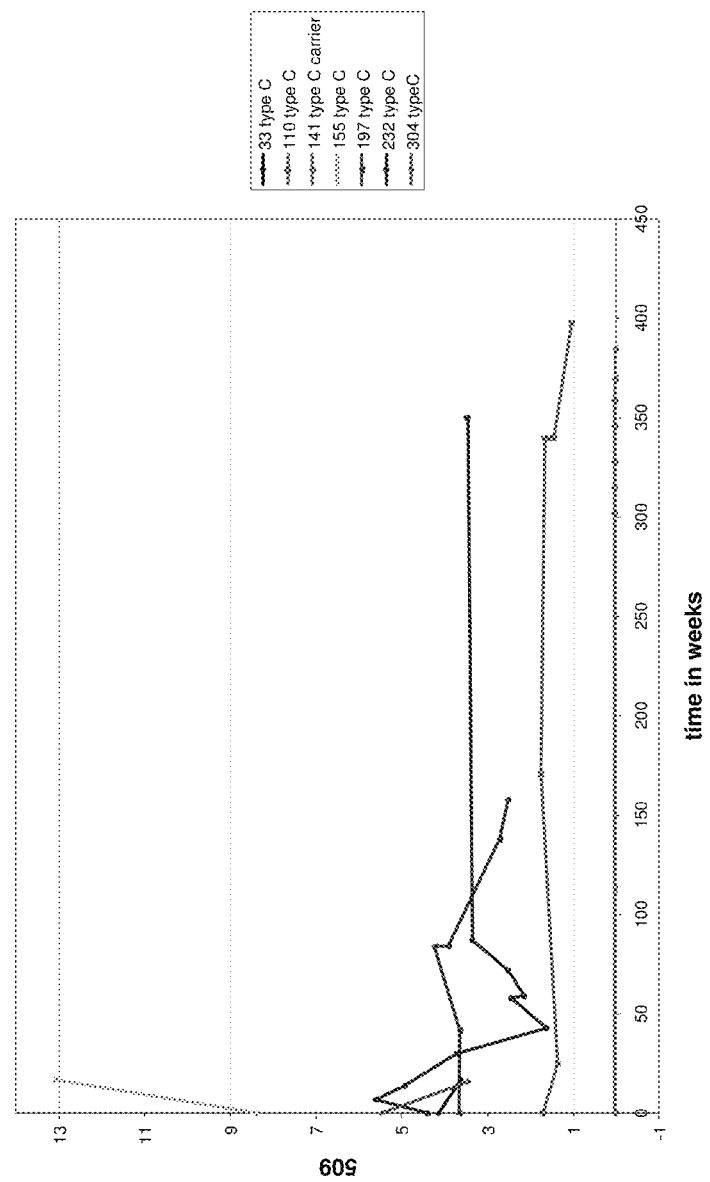
FIG. 7 is a diagram showing plasma levels of a biomarker of the present invention as a function over time for a total of 6 Niemann-Pick disease type C patients and 1 Niemann-Pick disease type C carrier.

The levels of compound 509 over time for individual patients are shown in FIG. 7.

More particularly, FIG. 7 is a diagram showing the levels of compound 509 in ng/ml plasma as a function over time for a total of 6 Niemann-Pick disease type C patients and 1 Niemann-Pick disease type C carrier.

The level of the respective biomarker was determined by the method according to the present invention in a plasma sample from the Niemann-Pick disease type C patients which were subjected to therapy during the course of the study. Each curve and each patient number, respectively, represents levels determined in plasma collected from the same patient at different time points as indicated on the x-axis. The x-axis represents the time points of plasma collection, wherein time point zero indicates the first measure under therapy for each patient. For the analysis of the change of the level of the biomarker according to the present invention over time in Niemann-Pick disease type C patients as described in Example 3 non aggregated data was used for those patients for which more than one plasma sample has been analysed. In FIG. 7 the y-axis represents levels of compound 509 as a function over time.

Example 5: Analysis of Levels of Biomarkers Depending on Age of Subjects

Lysosomal storage diseases affect mostly children and they often die at a young and unpredictable age, many within a few months or years of birth. Many other children die of this disease following years of suffering from various symptoms of their particular disorder.

It is thus from particular interest to test the value of the biomarkers of the invention for the diagnosis of Niemann-Pick disease in groups of patients of young age.

A preferable biomarker for the diagnosis of Niemann-Pick disease, preferably Niemann-Pick disease type C, would allow for diagnosis of Niemann-Pick disease, preferably Niemann-Pick disease type C, with high sensitivity and high specificity independent from the age of the subject.

The levels of compound 465 and compound 509, respectively, determined according to the method of the present invention were analyzed with respect to the age of the subject.

The result is shown in Table 5 and FIG. 9.

Table 5 below shows the distribution of age among the tested subjects.

TABLE 5A

| | Distribution of age | |
|---|---|---|
| age in years | dgn | cases valid N |
| 1.00 0-10 | 1.00 Niemann-Pick type A/B | 7 |
| | 2.00 Niemann-Pick type C | 10 |
| | 4.00 gaucher | 1 |
| | 5.00 other LSD | 20 |
| | 6.00 control | 5 |
| 2.00 11-20 | 1.00 Niemann-Pick type A/B | 3 |
| | 2.00 Niemann-Pick type C | 13 |
| | 4.00 gaucher | 2 |
| | 5.00 other LSD | 8 |
| | 6.00 control | 2 |
| 3.00 21-30 | 2.00 Niemann-Pick type C | 11 |
| | 5.00 other LSD | 11 |
| | 6.00 control | 8 |
| | 3.00 Niemann-Pick type C carrier | 2 |
| 4.00 31-40 | 4.00 gaucher | 1 |
| | 5.00 other LSD | 12 |
| | 6.00 control | 16 |
| | 3.00 Niemann-Pick type C carrier | 2 |
| 5.00 41-50 | 4.00 gaucher | 4 |
| | 5.00 other LSD | 20 |
| | 6.00 control | 30 |
| | 3.00 Niemann-Pick type C carrier | 6 |
| 6.00 51-60 | 1.00 Niemann-Pick type A/B | 1 |
| | 4.00 gaucher | 3 |
| | 5.00 other LSD | 13 |
| | 6.00 control | 30 |
| | 3.00 Niemann-Pick type C carrier | 4 |
| 7.00 61-70 | 4.00 gaucher | 2 |
| | 5.00 other LSD | 5 |
| | 6.00 control | 5 |
| 8.00 71 or older | 5.00 other LSD | 2 |
| | 6.00 control | 2 |

Figure 9A:
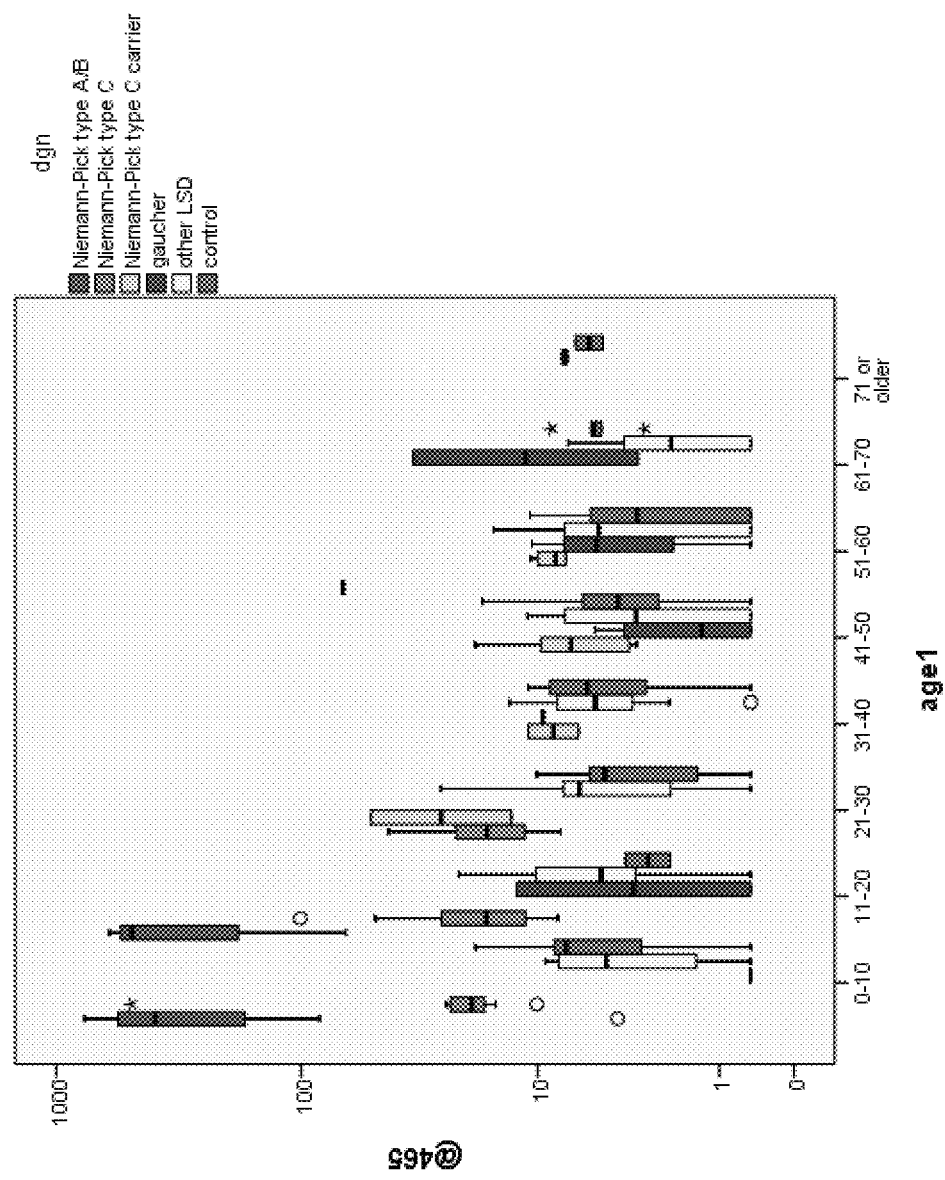
Figure 9B:
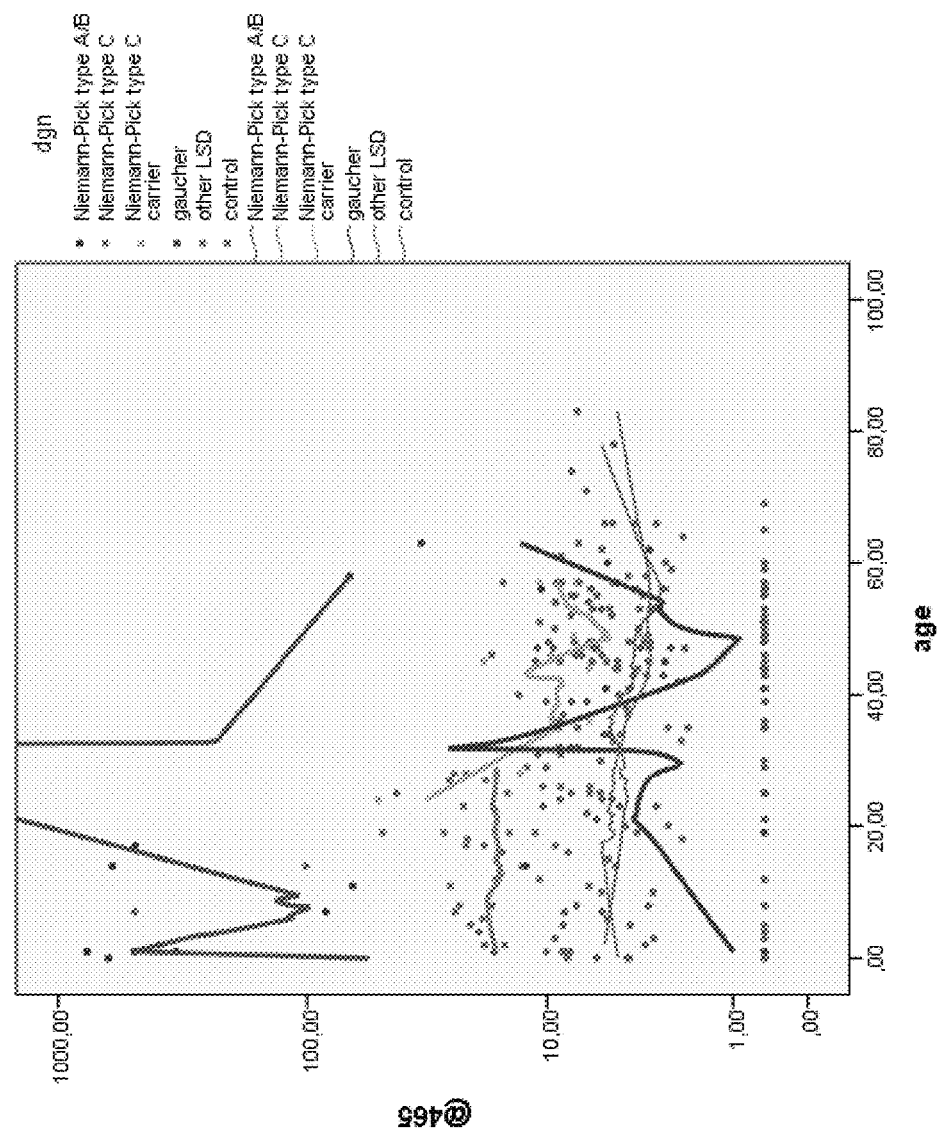
Figure 9C:
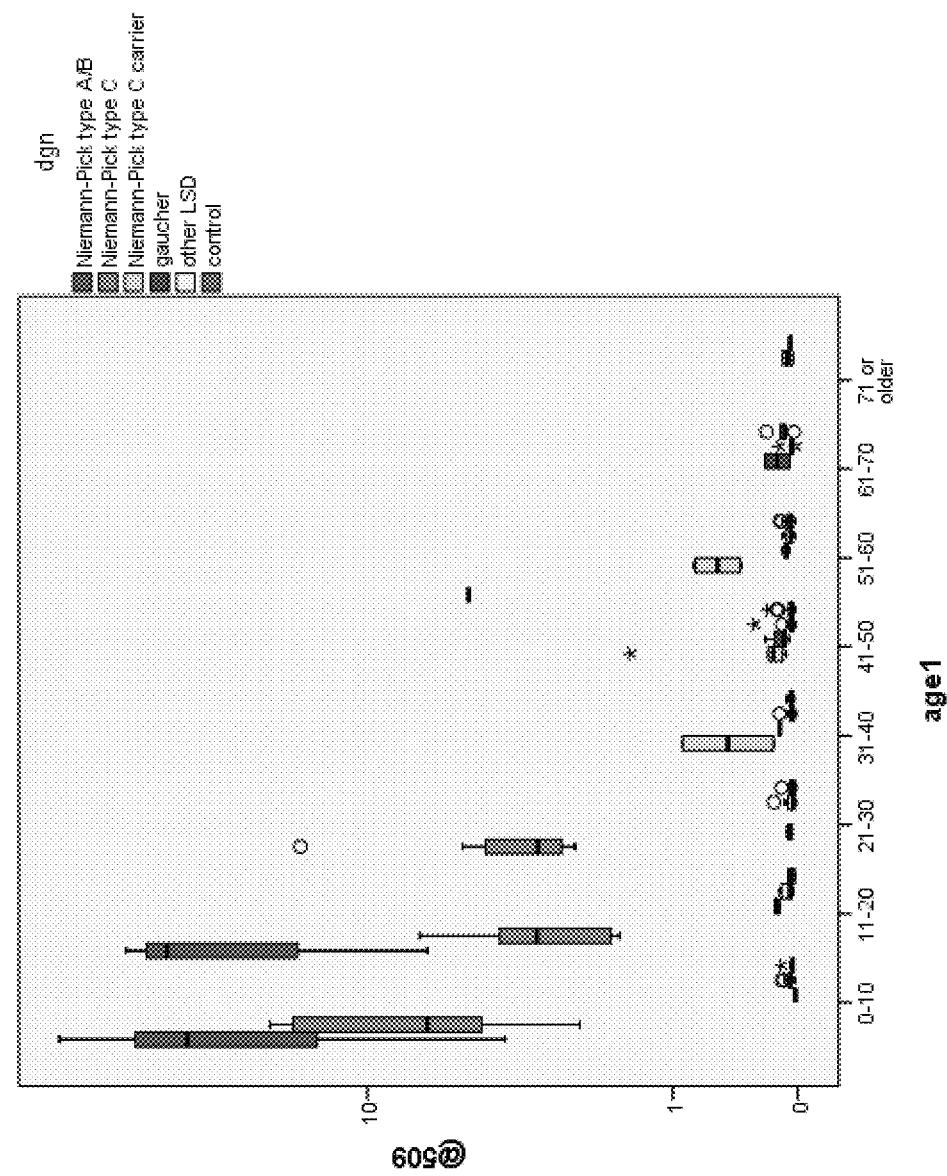
Figure 9D:
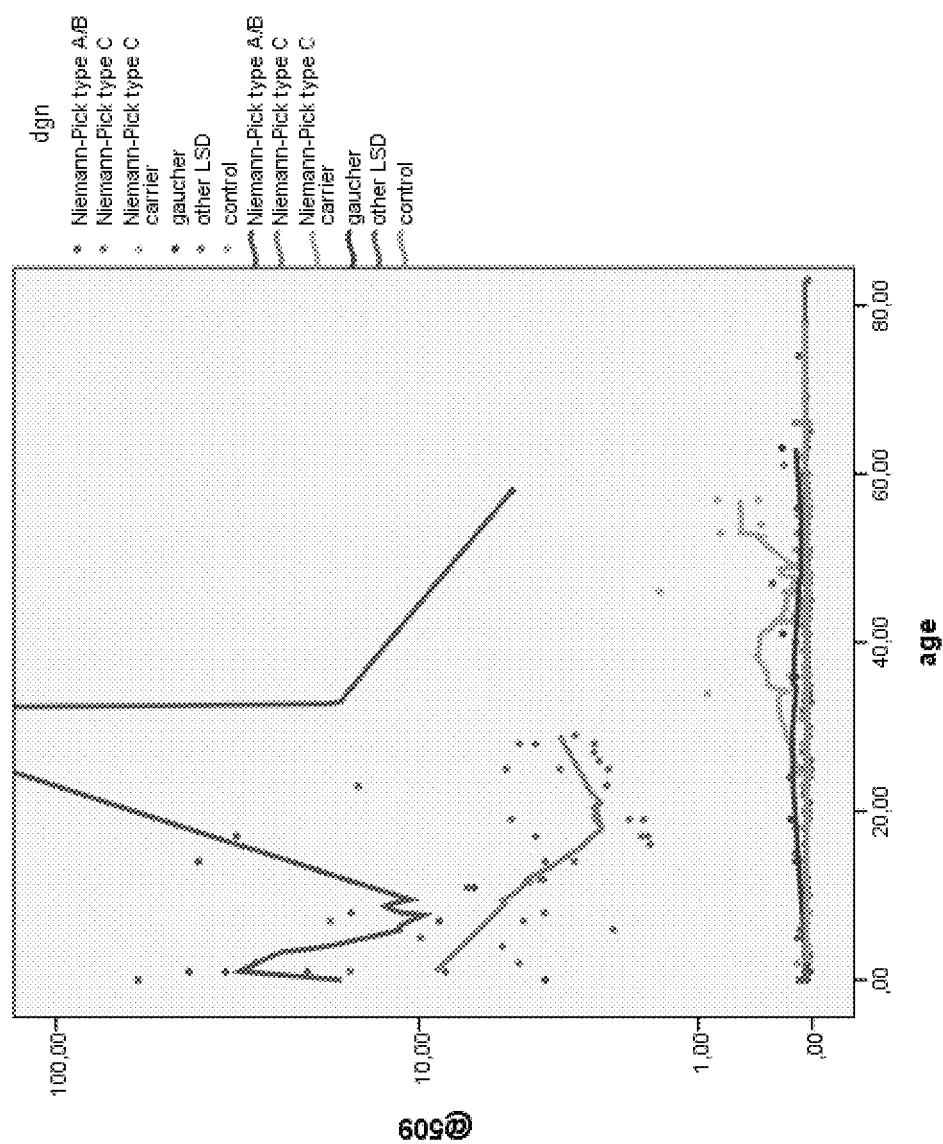

More particularly, FIG. 9A is a boxplot and FIG. 9B is a scatterplot indicating levels of free lyso-sphingomyelin, i.e. compound 465; and FIG. 9C is a boxplot and FIG. 9D is a scatterplot indicating levels of compound 509; The y-axis demonstrates the logarithmised levels of free lyso-sphingomyelin and compound 509, respectively, in ng/ml determined in plasma of patients by the method according to the present invention, wherein the x-axis depicts groups of patients by years of age. In boxplots the patients have been grouped by age in years as indicated, i.e. patients being 0-10, 11-20, 21-30, 31-40, 41-50, 51-60, 61-70 years old or being 71 years old and older The boxplot represents the $25^{th}$ and $75^{th}$ percentile of each group of patients by the bottom and top of the box, respectively; the band near the middle of the box represents the $50^{th}$ percentile (i.e. the median) of each group; The whiskers represent one standard deviation above and below the mean of the data; Any data not included between the whiskers is shown as an outlier with a small circle or star.

It may be immediately taken therefrom that compound 509 as well as compound 465 are biomarker which allow for the diagnosis of Niemann-Pick disease, preferably Niemann-Pick disease type A/B and more preferably Niemann-Pick disease type C with high sensitivity and high specificity independent from the age of the subject.

Furthermore it can be taken from that the method of the present invention thus allows for diagnosing Niemann-Pick disease in a subject independent from age. More particularly, the method of the present invention allows for diagnosing Niemann-Pick disease in a subject, wherein the subject is a subject of young age, more particularly of less than 30 years of age, less than 20 years of age or less than 10 years of age.

Example 6: Free Lyso-Gb3 in Cerebellum of Transgenic Rats

The level of free lyso-sphingomyelin was determined in the cerebellum of 3 transgene NPC1−/− rats and compared to the level in a sample from a control animal (NPC1+/+).
The results are shown in table 6.

TABLE 6

Lyso-Gb3 rat animal cerebellum

| id | code | | sex | Matrix | | free lyso-Sphingomyelin |
|---|---|---|---|---|---|---|
| G6 | 1 cerebellum | NPC1 −/− | f | P50 | extract of murine tissue | 11.8 |
| G7 | 2 cerebellum | NPC1 −/− | f | P50 | extract of murine tissue | 20.9 |
| G8 | 10 cerebellum | NPC1 −/− | f | P50 | extract of murine tissue | 20.1 |
| G9 | F1 cerebellum | NPC1 +/+ | m | adult | extract of murine tissue | 7.21 |

It can be taken from the above that the level of free lyso-sphingomyelin is elevated, by approximately factor 2 to 3, in the cerebellum in NPC1−/− animals to samples from control animals without gene-knock-out, i.e. NPC1+/+.

In other words, in the cerebellum of NOC1− knock-out animals free lyso-Sphingomyelin concentration is about double as high as in wildtype controls Said finding correlates with histopathological situation in humans, wherein preferably the cerebellum is affected.

The features of the present invention disclosed in the specification, the claims, the sequence listing and/or the drawings may both separately and in any combination thereof be material for realizing the invention in various forms thereof.

What is claimed is:

1. A method for generating quantitative data for a subject comprising determining a level of a biomarker in samples from the subject, wherein the samples are samples of blood on a dry blood filter card, wherein the samples were taken at several points in time from the subject, wherein the biomarker is free lyso-sphingomyelin and wherein the subject is suffering from Niemann-Pick disease or suspected of suffering from Niemann-Pick disease.

2. The method according to claim 1, wherein the method further comprises:

i) adding an internal standard to a sample from the subject, wherein the sample from the subject is blood;

ii) optionally mixing the sample containing the internal standard;

iii) subjecting the sample to a protein precipitation step, wherein protein from the sample is precipitated and a first supernatant of the sample is provided;

iv) optionally subjecting the first supernatant of the sample or at least a part thereof to a first separation step which provides a second supernatant, optionally wherein the first separation step is a step of centrifugation;

v) subjecting the first supernatant and/or the second supernatant, or at least a part thereof, to a second separation step, wherein the second separation step comprises injecting at least a part of the first supernatant and/or at least a part of the second supernatant into an HPLC-MS/MS system and using an HPLC column with a gradient from acidic water to acetonitrile/acetone; wherein the HPLC column is an HPLC column selected from the group consisting of a C8 HPLC column and a C18 HPLC column, and wherein the second separation step provides a separated sample; and vi) subjecting the separated sample to MS/MS, wherein MS/MS comprises electrospray ionization and Multiple Reaction Monitoring, thereby detecting the biomarker.

3. The method of claim 1, wherein the samples are taken every three months.

4. The method of claim 1, wherein the samples are taken every six months.

5. The method according to claim 1, wherein the biomarker is detected by means of immunoassay, mass spectrometric analysis, biochip array, functional nucleic acids and/or a fluorescent derivative of the biomarker.

6. The method according to claim 5, wherein mass spectrometric analysis is selected from the group consisting of SELDI, MALDI, MALDI-Q TOF, MS/MS TOF-TOF and ESI-O-TOF.

7. The method according to claim 1, wherein Niemann-Pick disease is selected from the group consisting of Niemann-Pick disease type A and B, Niemann-Pick disease type C, and Niemann-Pick disease type C carrier.

* * * * *

UNITED STATES PATENT AND TRADEMARK OFFICE
CERTIFICATE OF CORRECTION

| | |
|---|---|
| PATENT NO. | : 11,231,412 B2 |
| APPLICATION NO. | : 16/541716 |
| DATED | : January 25, 2022 |
| INVENTOR(S) | : Rolfs et al. |

It is certified that error appears in the above-identified patent and that said Letters Patent is hereby corrected as shown below:

On the Title Page

(56) References Cited:

P 2, Other Publications, Anne-Katrin Giese cite:
Please correct "specific biomarkers"
To read -- specific biomarker -- and,
Correct "Orphanet Jounral"
To read -- Orphanet Journal --

P 2, Other Publications, Tomas Blom et al. cite:
Please correct "Transport in Sphingollpldoses"
To read -- Transport in Sphingolipidoses --

P 2, Other Publications, Rodriguez-Lafrassee cite:
Please correct "Sphingosylphosphorycholine"
To read -- Sphingosylphosphorylcholine --

In the Claims

Column 72, Claim 6, Line 59:
Please correct "MS/MS TOF-TOF"
To read -- MS/MS, TOF-TOF --

Signed and Sealed this
Twenty-eighth Day of June, 2022

Katherine Kelly Vidal
*Director of the United States Patent and Trademark Office*